US012371708B2

(12) United States Patent
Rohde et al.

(10) Patent No.: US 12,371,708 B2
(45) Date of Patent: Jul. 29, 2025

(54) PLANTS COMPRISING WHEAT G-TYPE CYTOPLASMIC MALE STERILITY RESTORER GENES, MOLECULAR MARKERS AND USES THEREOF

(71) Applicant: BASF SE, Ludwigshafen am Rhein (DE)

(72) Inventors: Antje Rohde, Ghent (BE); John Jacobs, Merelbeke (BE); Mark Davey, Ghent (BE)

(73) Assignee: BASF SE, Ludwigshafen am Rhein (DE)

( * ) Notice: Subject to any disclaimer, the term of this patent is extended or adjusted under 35 U.S.C. 154(b) by 448 days.

(21) Appl. No.: 17/200,258

(22) Filed: Mar. 12, 2021

(65) Prior Publication Data

US 2021/0269822 A1    Sep. 2, 2021

Related U.S. Application Data

(63) Continuation of application No. 16/318,535, filed as application No. PCT/EP2017/068162 on Jul. 18, 2017, now abandoned.

(30) Foreign Application Priority Data

Jul. 18, 2016   (EP) ..................................... 16180019

(51) Int. Cl.
| | | |
|---|---|---|
| C12N 15/82 | (2006.01) | |
| A01H 1/04 | (2006.01) | |
| C07K 14/415 | (2006.01) | |
| C12Q 1/68 | (2018.01) | |
| C12Q 1/6895 | (2018.01) | |

(52) U.S. Cl.
CPC ......... *C12N 15/8289* (2013.01); *A01H 1/045* (2021.01); *C07K 14/415* (2013.01); *C12N 15/8213* (2013.01); *C12N 15/8231* (2013.01); *C12Q 1/68* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,639,948 A | 6/1997 | Michiels et al. |
| 7,071,375 B2 | 7/2006 | Brown et al. |
| 9,012,729 B2 | 4/2015 | Gils |

FOREIGN PATENT DOCUMENTS

| | | | |
|---|---|---|---|
| WO | WO-2019086510 A1 * | 5/2019 | ............... A01H 1/02 |

OTHER PUBLICATIONS

Salamini et al, Genetics and Geography of Wild Cereal Domestication in the Near East, 2002, Nature Review Genetics 3: 429-441 (Year: 2002).*
Barkan et al, Pentatricopeptide Repeat Proteins in Plants 2014, Annual Review of Plant Biology 65: 415-442 (Year: 2014).*
Melonek et al, Evolutionary plasticity of restorer-of-fertility-like proteins in rice, 2016, Scientific Reports 6:35152 (Year: 2016).*
Melonek et al, The genetic basis of cytoplasmic male sterility and fertility restoration in wheat, 2021, Nature Communications, 12: 1036, pp. 1-14 (Year: 2021).*
Melonek et al, The genetic basis of cytoplasmic male sterility and fertility restoration in wheat, 2021, Nature Communications, 12: 1036, Supplementary Information (Year: 2021).*
Hedgcoth et al, A chimeric open reading frame associated with cytoplasmic male sterility in alloplasmic wheat ith Triticum timopheevi mitochondria is present in several *Triticum* and *Aegilops* species, barley, and rye, 2002, Current Genetics 41: 357-365 (Year: 2002).*
Kucera 1982, Euphytica: 31, pp. 895-900 (as cited in IDS filed by Applicant on Feb. 5, 2024). (Year: 1982).*
Zhang, et al., "Location of the fertility restorer gene for T-type CMS wheat by Microsatellite Marker", Acta Genetica Sinica, vol. 30, Issue 5, May 2003, pp. 459-464.
Zhou, et al., "SSR markers associated with fertility restoration genes against Triticum timopheevii cytoplasm in Triticum aestivum", Euphytica, vol. 141, Issue 1-2, Jan. 2005, pp. 33-40.
Toyoma, et al., "Fine Genetic Mapping of Nuclear Gene, Rf-1, that restores the BT-type cytoplasmic male sterility," Euphytica, vol. 129, 2003, pp. 241-247.
"*Triticum aestivum* L. subsp. *Aestivum*", PI 583676, U.S. National Plant Germplasm System, XP002770568, 1994, 1 page.
Ahmed, et al., "QTL analysis of fertility-restoration against cytoplasmic male sterility in wheat", Genes & Genetic Systems, vol. 76, Issue 1, 2001, pp. 33-38.
Akagi, et al., "Positional cloning of the rice Rf-1 gene, a restorer of BT-type cytoplasmic male sterility that encodes a mitochondria-targeting PPR protein", Theoretical and Applied Genetics, vol. 108, Issue 8, May 2004, pp. 1449-1457.
Bahl, et al., "Chromosomal Location of Male Fertility Restoring Genes in Six Lines of Common Wheat", Crop Science, vol. 13, Issue 3, 1973, pp. 317-320.
Barkan, et al., "A Combinatorial Amino Acid Code for RNA Recognition by Pentatricopeptide Repeat Proteins", PLOS Genetics, vol. 8, Issue 8, Aug. 2012, p. e1002910 (1-8).
Binder, et al., "P-class pentatricopeptide repeat proteins are required for efficient 5' end formation of plant mitochondrial transcripts", RNA Biology, vol. 10, Issue 9, 2013, pp. 1511-1519.
Bortesi, et al., "Patterns of CRISPR/Cas9 activity in plants, animals and microbes", Plant Biotechnology Journal, vol. 14, 2016, pp. 2203-2216.
Burstein, et al., "New CRISPR-Cas systems from uncultivated microbes", Nature, vol. 542, Feb. 9, 2017, pp. 237-241.

(Continued)

*Primary Examiner* — Brent T Page
*Assistant Examiner* — Aleksandar Radosavljevic
(74) *Attorney, Agent, or Firm* — ArentFox Schiff LLP

(57) ABSTRACT

Methods are described for selecting or producing a cereal plant comprising a functional restorer gene for wheat G-type cytoplasmic male sterility and nucleic acids for use therein.

22 Claims, 5 Drawing Sheets

Figure 1:
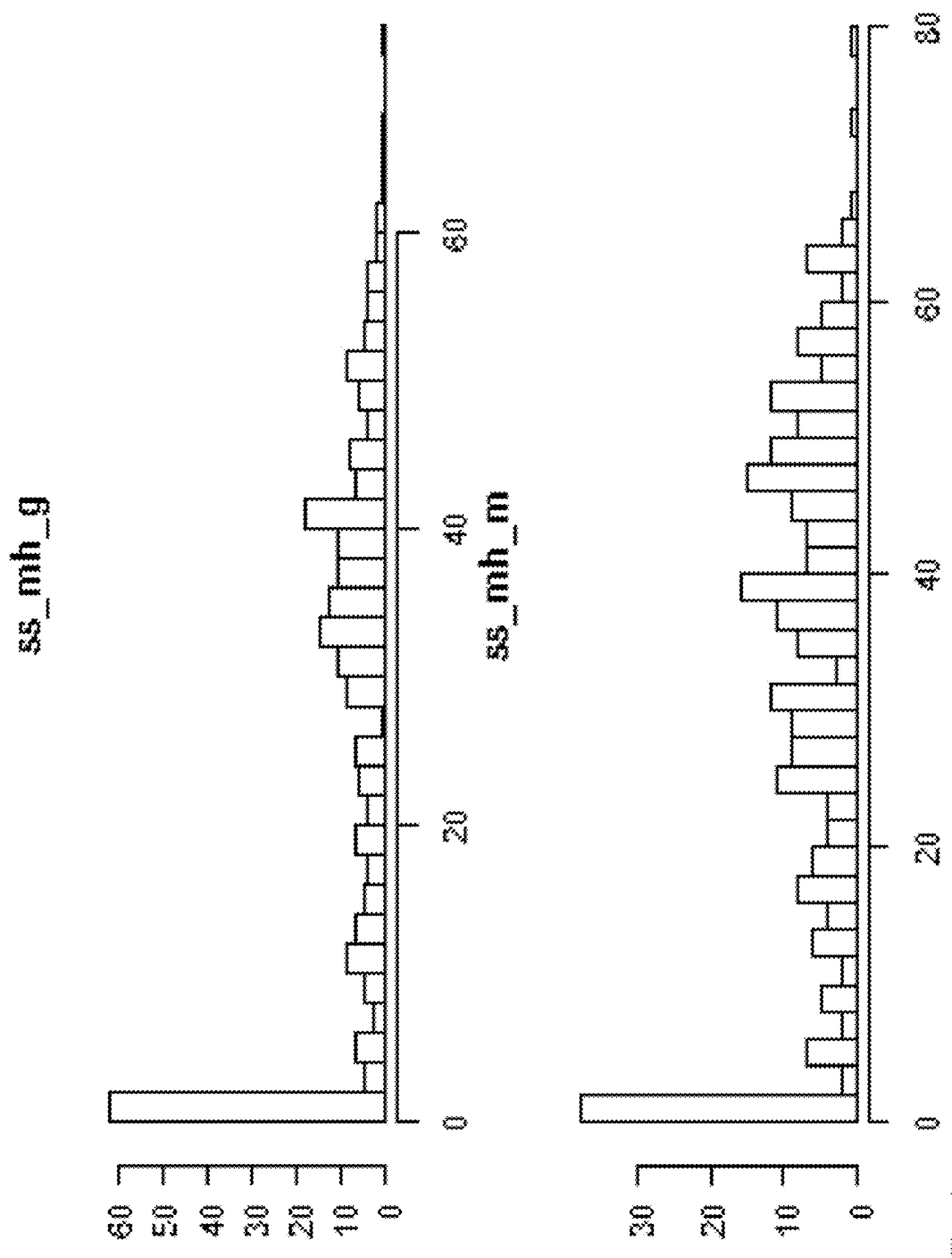

Specification includes a Sequence Listing.

(56) References Cited

OTHER PUBLICATIONS

Chen, et al., "Identification of miRNAs and their targets through high-throughput sequencing and degradome analysis in male and female Asparagus officinalis", BMC Plant Biology, vol. 16, Issue 80, 2016, 19 pages.
Chen, et al., "Male Sterility and Fertility Restoration in Crops", Annual Review of Plant Biology, vol. 65, Apr. 2014, pp. 579-606.
Dahan, et al., "The Rf and Rf-like PPR in higher plants, a fast-evolving subclass of PPR genes", RNA Biology, vol. 10, Issue 9, 2013, pp. 1469-1476.
Database PVPO—Certificate Status [Online], Database accession No. 7400045, XP002770567, Oct. 17, 1975, 16 pages.
Ding, et al.,"A long noncoding RNA regulates photoperiod-sensitive male sterility, an essential component of hybrid rice", Proceedings of the National Academy of Sciences of the United States of America, vol. 109, Issue 7, Feb. 14, 2012, pp. 2654-2659.
Du, et al., "Genetic Analyses of Male-Fertility Restoration in Wheat: III. Effects of Aneuploidy", Crop Science, vol. 31, Issue 2, 1991, pp. 319-322.
F. A. Lilienfeld, "H. Kihara: Genome-Analysis in Triticum and Aegilops. X: Concluding Review", Cytologia, vol. 16, Issue 2, 1951, pp. 101-123.
Fang, et al., "High-throughput sequencing and degradome analysis reveal altered expression of miRNAs and their targets in a male-sterile cybrid pummelo (*Citrus grandis*)", BMC Genomics, vol. 17, Issue 591, 2016, 15 pages.
Fujii, et al., "Selection patterns on restorer-like genes reveal a conflict between nuclear and mitochondrial genomes throughout angiosperm evolution", Proceedings of the National Academy of Sciences of the United States of America, vol. 108, Issue 4, Jan. 25, 2011, pp. 1723-1728.
G. C. M. Sage, "Nucleo-cytoplasmic relationships in wheat", Advances in Agronomy, vol. 28, 1976, pp. 267-300.
Gaborieau, et al., "The Propensity of Pentatricopeptide Repeat Genes to Evolve into Restorers of Cytoplasmic Male Sterility", Frontiers in Plant Science, vol. 7, Issue 1816, Dec. 2016, 10 pages.
Geyer, et al., "Distribution of the fertility-restoring gene Rf3 in common and spelt wheat determined by an informative SNP marker", Molecular Breeding, vol. 36, Issue 12, Dec. 2016, 11 pages.
Haley, et al., "A simple regression method for mapping quantitative trait loci in line crosses using flanking markers", Heredity, vol. 69, 1992, pp. 315-324.
Hedgcoth, et al., "A chimeric open reading frame associated with cytoplasmic male sterility in alloplasmic wheat with Triticum timopheevi mitochondria is present in several *Triticum* and *Aegilops* species, barley, and rye", Current Genetics, vol. 41, Issue 5, Aug. 2002, pp. 357-366.
International Search Report for PCT Patent Application No. PCT/EP2017/068162, Issued on Sep. 22, 2017, 4 pages.
Ishida, et al., "Chapter 15—Wheat (*Triticum aestivum* L.) Transformation Using Immature Embryos", Methods in Molecular Biology, vol. 1223, Sep. 13, 2014, pp. 189-198.
Kojima, et al., "High-resolution RFLP mapping of the fertility restoration (Rf3) gene against Triticum timopheevi cytoplasm located on chromosome 1 BS of common wheat", Genes & Genetic Systems, vol. 72, Issue 6, 1997, pp. 353-359.
Komor, et al., "Programmable editing of a target base in genomic DNA without double-stranded DNA cleavage", Nature, vol. 533, May 19, 2016, pp. 420-424.
Komori, et al., "Map-based cloning of a fertility restorer gene, Rf-1, in rice (*Oryza sativa* L.)", The Plant Journal, vol. 37, Issue 3, Feb. 2004, pp. 315-325.
Lander, et al., "Mapping mendelian factors underlying quantitative traits using RFLP linkage maps", Genetics, vol. 121, Issue 1, Jan. 1, 1989, pp. 185-199.
Ma, et al., "CRISPR/Cas9 Platforms for Genome Editing in Plants: Developments and Applications", Molecular Plant, vol. 9, Issue 7, Jul. 6, 2016, pp. 961-974.

Ma, et al., "Genetic Analysis of Fertility Restoration in Wheat Using Restriction Fragment Length Polymorphisms", Crop Science, vol. 35, Issue 4, Jul. 1995, pp. 1137-1143.
Ma, et al., "Incorporation of restoring gene of Aegilops umbellulata into wheat", Genome, vol. 34, Issue 5, 1991, pp. 727-732.
Melonek, et al., "Evolutionary plasticity of restorer-of-fertility-like proteins in rice", Scientific Reports, vol. 6, Issue 35152, 2016, 12 pages.
Mohan L. H. Kaul, "Male Sterility in Higher Plants", Monographs on Theoretical and Applied Genetics, vol. 10, Issue 1, 1988, 1016 pages.
Mukai, et al., "Basic studies on hybrid wheat breeding", Theoretical and Applied Genetics, vol. 54, Issue 4, Jul. 1979, pp. 153-160.
Murovec, et al., "New variants of CRISPR RNA-guided genome editing enzymes", Plant Biotechnology Journal, vol. 15, Issue 8, Aug. 2017, pp. 917-926.
Nakade, et al., "Cas9, Cpf1 and C2c1/2/3—What's next?", Bioengineered, vol. 8, Issue 3, 2017, pp. 265-273.
Osakabe, et al., "Genome Editing with Engineered Nucleases in Plants", Plant and Cell Physiology, vol. 56, Issue 3, Mar. 2015, pp. 389-400.
R.C. Jansen, "Controlling the type I and type II errors in mapping quantitative trait loci.", Genetics, vol. 138, Issue 3, Nov. 1, 1994, pp. 871-881.
Robertson, et al., "Monosomic Analysis of Fertility-Restoration in Common Wheat (*Triticum aestivum* L.)", Crop Science, vol. 7, Issue 5, 1967, pp. 493-495.
Sam Manna, "An overview of pentatricopeptide repeat proteins and their applications", Biochimie, vol. 113, Jun. 2015, pp. 93-99.
Schmitz-Linneweber, et al., "Pentatricopeptide repeat proteins: a socket set for organelle gene expression", Trends in Plant Science, vol. 13, Issue 12, Dec. 2008, pp. 663-670.
Sinha, et al., "Genetic analysis and molecular mapping of a new fertility restorer gene Rf8 for Triticum timopheevi cytoplasm in wheat (*Triticum aestivum* L.) using SSR markers", Genetica, vol. 141, Issue 10-12, Oct. 2013, pp. 431-441.
Song, et al., "Influence of nuclear background on transcription of a chimeric gene (orf256) and coxI in fertile and cytoplasmic male sterile wheats", Genome, vol. 37, Issue 2, 1994, pp. 203-209.
Tahir, et al., "Monosomic analysis of *Triticum spelta* var. duhamelianum, a fertility-restorer for *T. timopheevi* cytoplasm", The Japanese Journal of Genetics, vol. 44, Issue 1, Jan. 1969, pp. 1-9.
Tsunewaki, et al., "Plasmon analysis of *Triticum* (wheat) and Aegilops. 1. Production of alloplasmic common wheats and their fertilities", Genes & Genetic Systems, vol. 71, 1996, pp. 293-311.
Wei, et al., "Comparative expression profiling of miRNA during anther development in genetic male sterile and wild type cotton", BMC Plant Biology, vol. 13, Issue 66, 2013, 14 pages.
Wei, et al., "The miRNAs and their regulatory networks responsible for pollen abortion in Ogura-CMS Chinese cabbage revealed by high-throughput sequencing of miRNAs, degradomes, and transcriptomes", Frontiers in Plant Science, vol. 6, Issue 894, Oct. 2015, 15 pages.
Wurschum, et al., "Genetic architecture of male fertility restoration of Triticum timopheevii cytoplasm and fine-mapping of the major restorer locus Rf3 on chromosome 1B", Theoretical and Applied Genetics, vol. 130, Issue 1, Mar. 2017, pp. 1253-1266.
Xia, et al., "MicroRNA Superfamilies Descended from miR390 and Their Roles in Secondary Small Interfering RNA Biogenesis in Eudicots", The Plant Cell, vol. 25, May 2013, pp. 1555-1572.
Yagi, et al., "Elucidation of the RNA Recognition Code for Pentatricopeptide Repeat Proteins Involved in Organelle RNA Editing in Plants", PLOS One, vol. 8, Issue 3, Mar. 2013, p. e57286 (1-8).
Kučera L., "Monosomic analysis of fertility restoration in common wheat 'Prof. Marchal'", Euphytica 31:895-900, 1982.
Dec. 22, 2021 Response in European Application No. 17751032.8 (20 pages).

* cited by examiner

PLANTS COMPRISING WHEAT G-TYPE CYTOPLASMIC MALE STERILITY RESTORER GENES, MOLECULAR MARKERS AND USES THEREOF

CROSS-REFERENCE TO RELATED APPLICATIONS

This application is continuation of U.S. application Ser. No. 16/318,535, filed Jan. 17, 2019, which is a National Stage Entry of PCT/EP2017/068162, filed Jul. 18, 2017, which claims priority to EP Patent Application No. 16180019.8, filed on Jul. 18, 2016, the disclosures of which are hereby incorporated by reference in their entireties.

FIELD OF THE INVENTION

The present invention relates generally to the field of plant breeding and molecular biology and concerns a method for selecting or producing a cereal plant comprising a functional restorer gene for wheat G-type cytoplasmic male sterility, and nucleic acids for use therein.

BACKGROUND

Cytoplasmic male sterility (CMS) is a major trait of interest in cereals such as wheat in the context of commercial hybrid seed production (Kihara, 1951; Wilson and Ross, 1962; Lucken, 1987; Sage, 1976). The cytoplasms of *Triticum timopheevi* (G-type) and *Aegilops kotschyi* (K-type) are widely studied as inducers of male sterility in common wheat (*Triticum aestivum*), due to few deleterious effects (Kaul, 1988; Lucken, 1987; Mukai and Tsunewaki, 1979).

In hybrid seed production system using the G-type cytoplasm, fertility restoration is a critical problem. Most of the hexaploid wheats do not naturally contain fertility restoration genes (Ahmed et al. Genes Genet. Syst. 2001). In the complicated restoration system of *T. timopheevi*, eight Rf genes are reported to restore the fertility against *T. timopheevii* cytoplasm, and their chromosome locations have been determined, namely, Rf1 (1A), Rf2 (7D), Rf3 (1B), Rf4 (6B), Rf5 (6D), Rf6 (5D), Rf7 (7B) and Rf8 (Tahir & Tsunewaki, 1969; Yen et al., 1969; Bahl & Maan, 1973; Du et al., 1991; Sihna et al., 2013). Ma et al. (1991) transferred an Rf gene from *Aegilops umbellulata* to wheat, the gene being located on chromosomes 6AS and 6BS (from Zhou et al., 2005).

Ma and Sorrels (Crop Science 1995) reported the linkage of Rf3 to RFLP markers Xbcd249 and Xcdo442 on chromosome 1BS.

Kojima (Genes Genet Syst 1997) localized a fertility restorer gene from Chinese Spring termed Rf3 gene at a position 1.2 cM and 2.6 cM distant from RFLP markers Xcdo388 and Xabc156, respectively, although the authors were able to separate Rf3 from Xcdo388. It was estimated that that Rf3 could exist within a region of 500 Kbp of the adjacent RFLP markers.

Ahmed Talaat et al (Genes Genet. Syst., 2001) determined the close linkage of a major Rf QTL against G-type cytoplasm on chromosome 1B with RFLP marker XksuG9c, close to marker Xabc156 as reported by Kojima et al (supra).

Zhang et al., (Yi Chuan Xue Bao 2003) describe an Rf gene located on 1BS with a genetic distance of 5.1 cM to microsatellite marker Xgwm550.

Zhou et al (2005) describe Rf3 gene to be located either between SSR markers Xgwm582 and Xbarc207 or between Xbarc207 and Xgwm131 but very close to Xbarc207. Since the previously identified RFLP markers of Kojima, Ahmed and Ma & Sorrels were not mapped in their mapping population, a linkage map including these RFLP markers could not be constructed to better estimate the distance between Rf3 and the identified SSR markers.

Accordingly, there remains the need for more accurate markers to identify and track Rf loci in breeding, which are particularly useful for hybrid seed production, and for improved methods for fertility restoration in wheat *Thimopheevi* cytoplasm. The present invention provides a contribution over the art by disclosing the functional Rf gene on chromosome 1B and by providing markers that are more tightly linked to the causal gene.

FIGURE LEGENDS

FIG. 1: Seed set on the main head (ss_mh), as observed in two different locations (g, m). Number of plants (y-axis) per class of amount of seed (x-axis).

Figure 2:
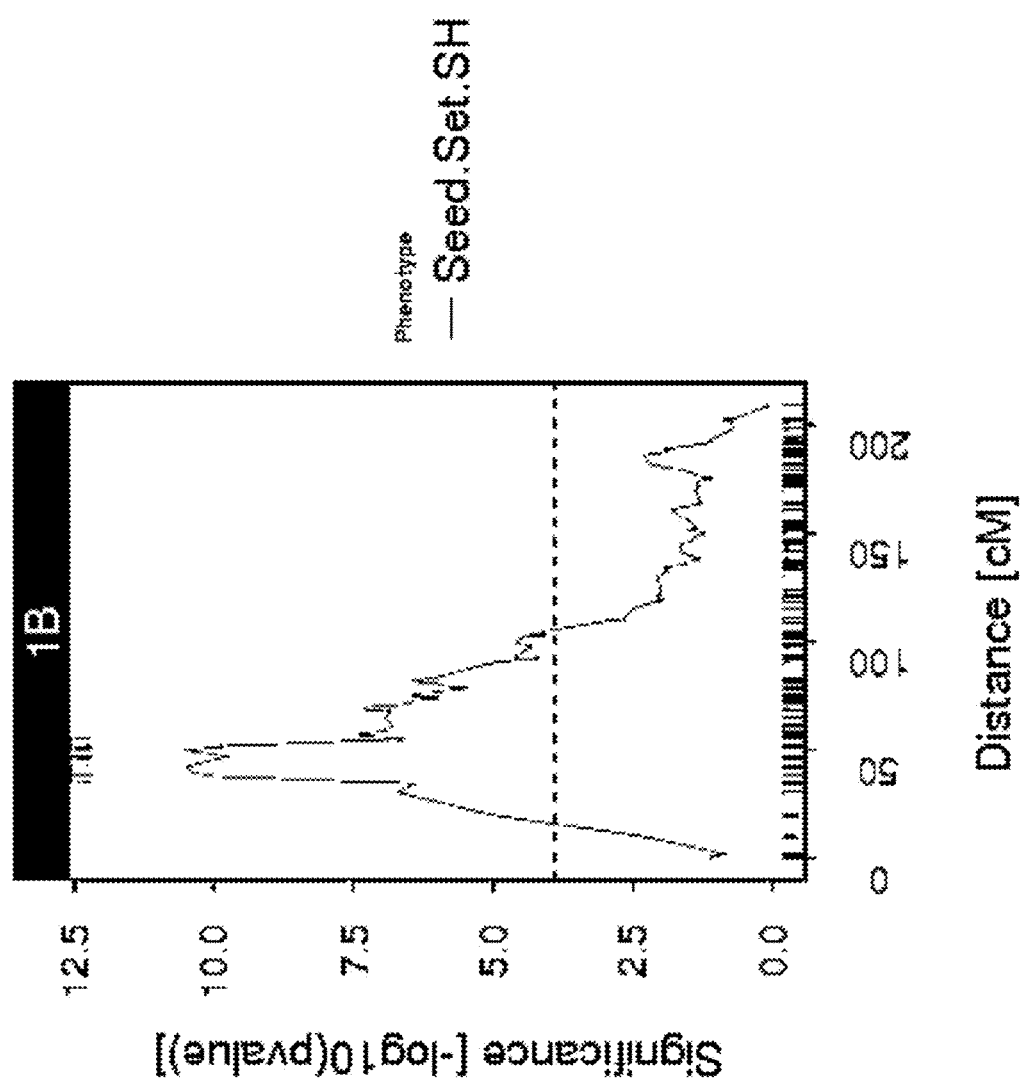

FIG. 2: Profile plot for significance of marker-trait associations along chromosome 1B in −log 10 (p) Indicative threshold=3.9.

Figure 3:
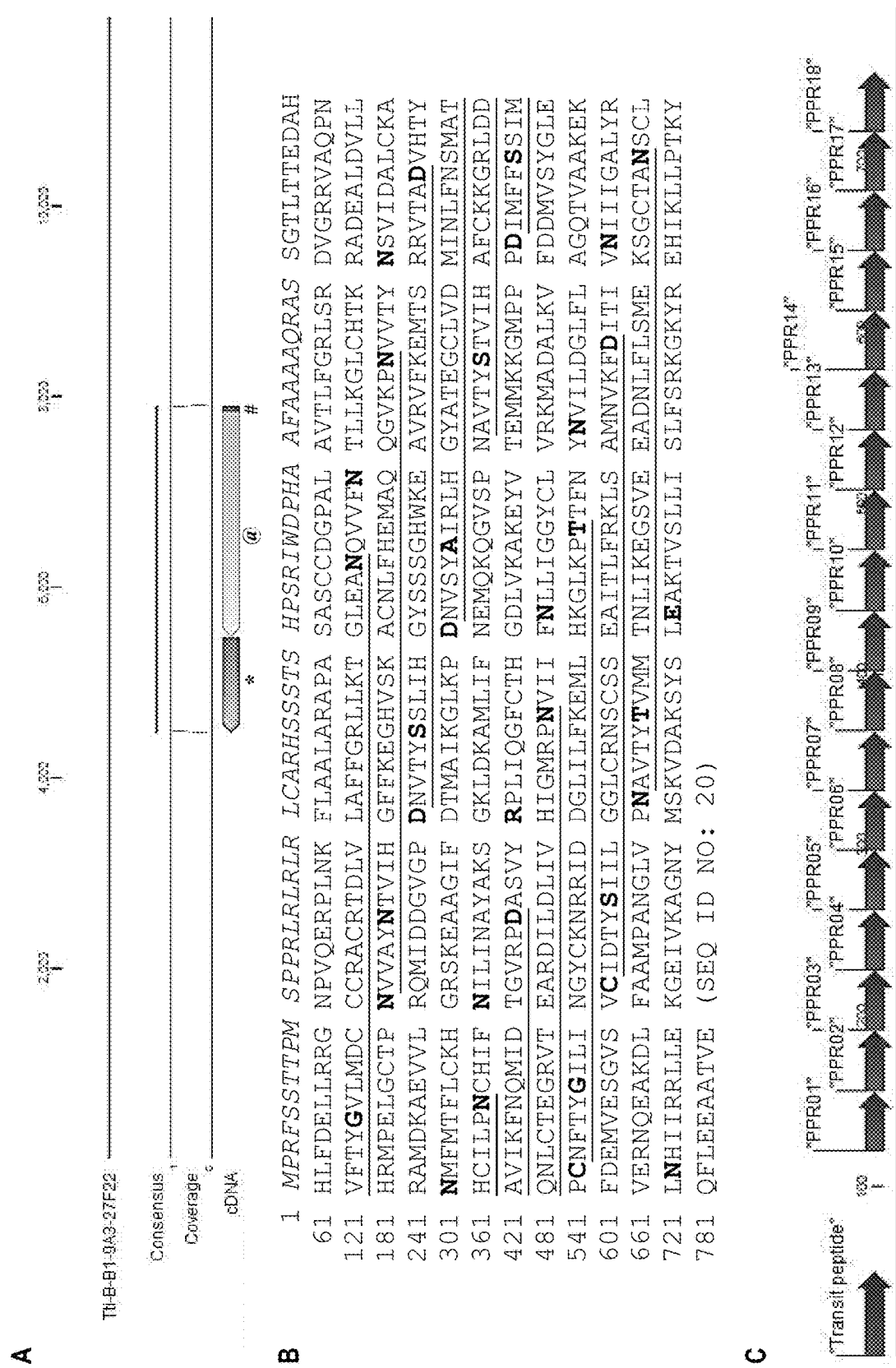

FIG. 3: (A)—Predicted gene structure for the identified PPR gene. @ indicates CDS, #5' UTR, and *3' UTR (B) amino acid sequence of identified PPR gene indicating the transit peptide (italic) and the PPR motifs (alternatingly underlined and not underlined) including the 5th and 35th amino acid implied in RNA recognition (bold). (C) Graphical representation of the structure of the PPR protein with transit peptide and PPR motifs.

Figure 4:
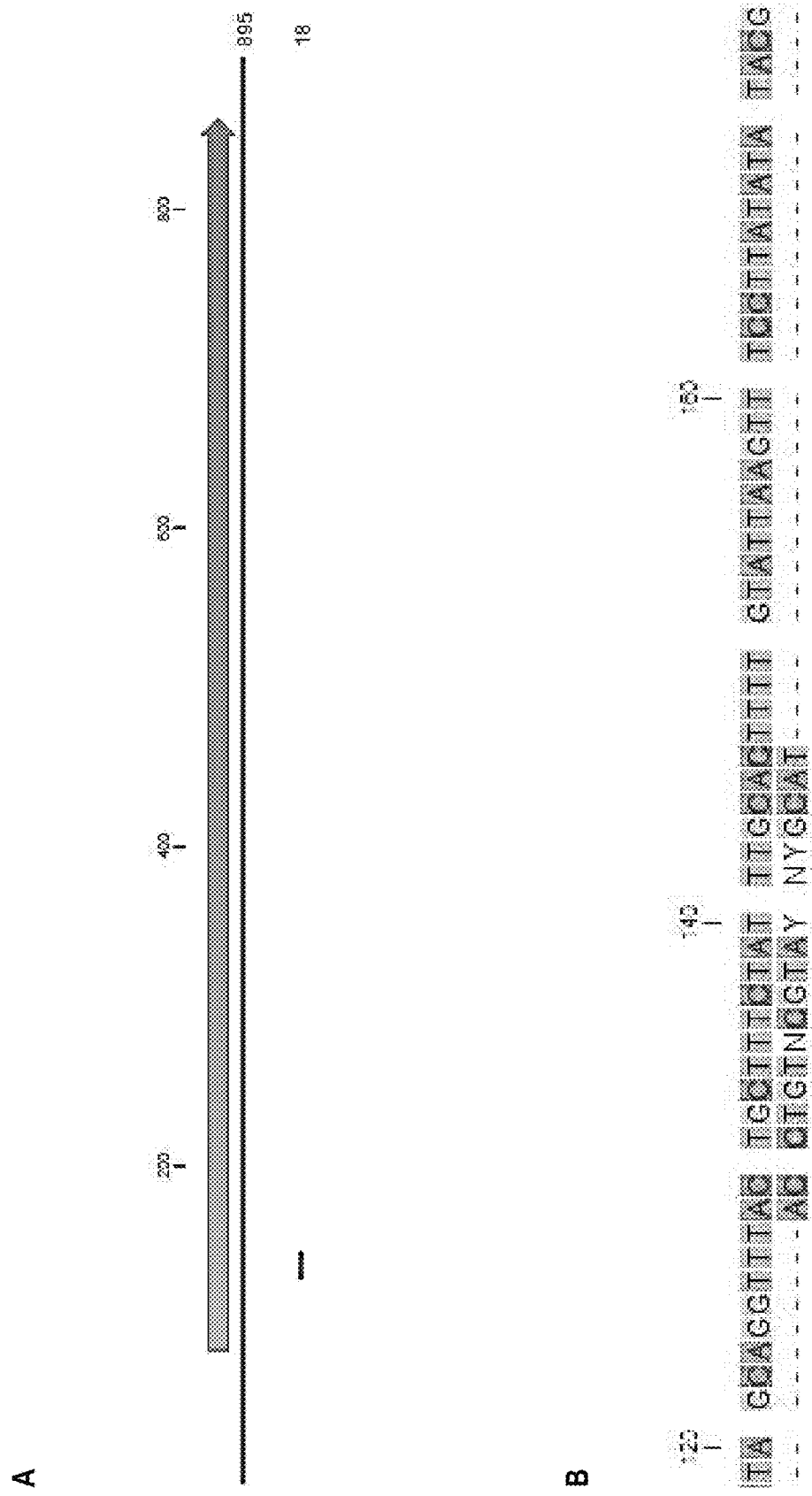

FIG. 4: (A) Overall alignment of the putative RNA recognition motif of the identified PPR protein with ORF256. (B) Close-up showing nucleotide alignment.

Figure 5:
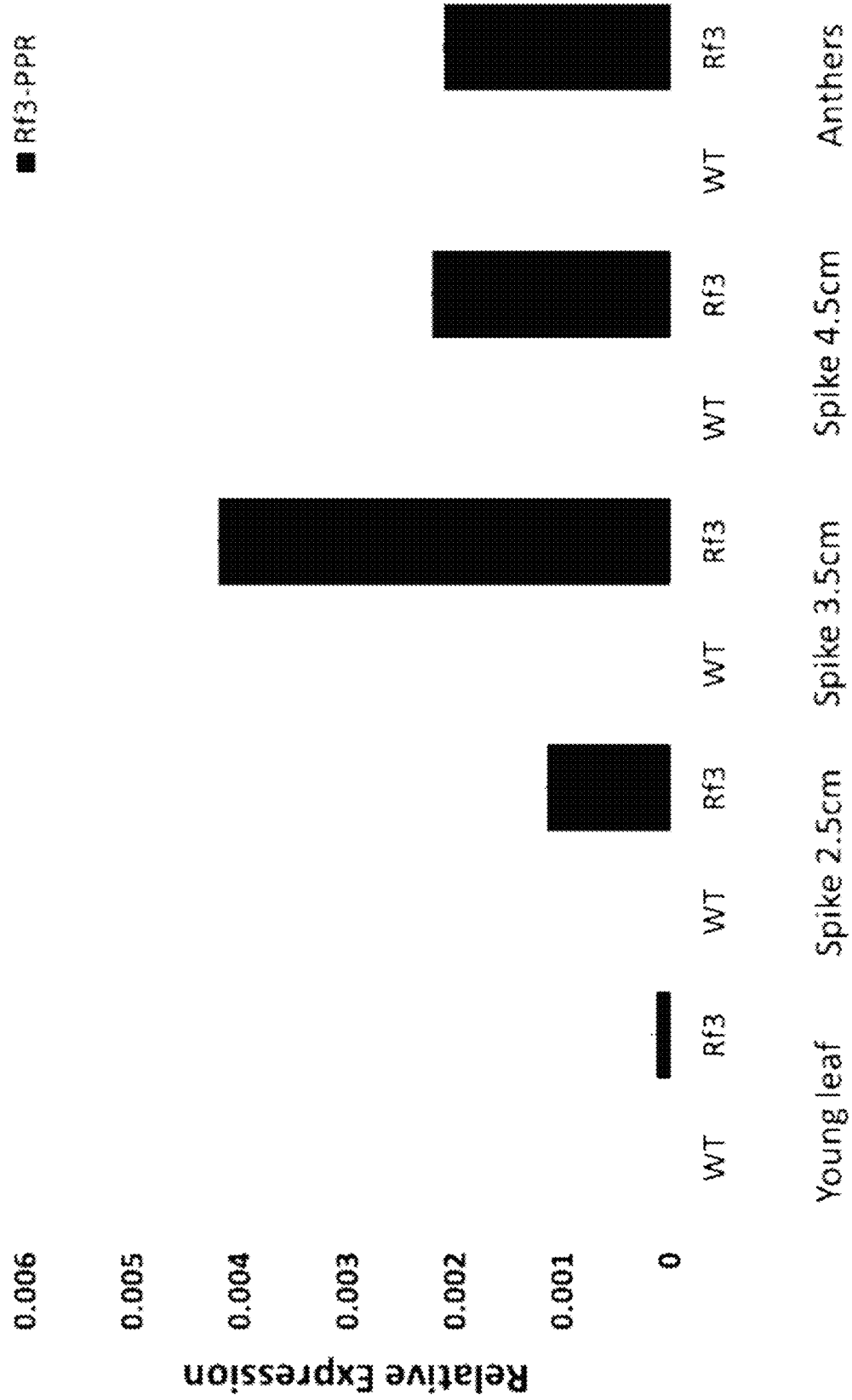

FIG. 5: Mean normalized expression levels of Rf3-PPR in tissues of Rf3 restorer and wild-type (non-restorer) F4 progeny of a cross between 'Resource-5' and a CMS line. Rf3-containing progeny were identified following KASP genotyping with fine-mapping markers and phenotyped to confirm restoration of fertility.

DETAILED DESCRIPTION

The present invention describes the identification of a functional restorer (Rf) locus and gene for wheat G-type cytoplasmic male sterility (i.e., *T. timopheevi* cytoplasm) located on chromosome 1B (short arm 1BS), as well as markers associated therewith. Said markers can be used in marker-assisted selection (MAS) of cereal plants, such as wheat, comprising said functional restorer genes located on chromosomes 1B. The identification of the genes and markers are therefore extremely useful in methods for hybrid seed production, as they can be used e.g. in a method for restoring fertility in progeny of a plant possessing G-type cytoplasmic male sterility, thereby producing fertile progeny plants from a G-type cytoplasmic male sterile parent plant. Likewise, the present disclosure also allows identifying plants lacking the desired allele, so that non-restorer plants can be identified and, e.g., eliminated from subsequent crosses.

One advantage of marker-assisted selection over field evaluations for fertility restoration is that MAS can be done at any time of year regardless of the growing season. Moreover, environmental effects are irrelevant to marker-assisted selection.

When a population is segregating for multiple loci affecting one or multiple traits, e.g., multiple loci involved in fertility restoration or multiple loci each involved in fertility restoration of different cytoplasmic male sterility (CMS)

systems or loci affecting distinct traits (for example fertility and disease resistance) the efficiency of MAS compared to phenotypic screening becomes even greater because all the loci can be processed in the lab together from a single sample of DNA. Any one or more of the markers and/or marker alleles, e.g., two or more, up to and including all of the established markers, can be assayed simultaneously.

Another use of MAS in plant breeding is to assist the recovery of the recurrent parent genotype by backcross breeding. Backcross breeding is the process of crossing a progeny back to one of its parents. Backcrossing is usually done for the purpose of introgressing one or a few loci from a donor parent into an otherwise desirable genetic background from the recurrent parent. The more cycles of backcrossing that are done, the greater the genetic contribution of the recurrent parent to the resulting variety. This is often necessary, because donor parent plants may be otherwise undesirable, i.e., due to low yield, low fecundity or the like. In contrast, varieties which are the result of intensive breeding programs may have excellent yield, fecundity or the like, merely being deficient in one desired trait such as fertility restoration. As a skilled worker understands, backcrossing can be done to select for or against a trait. For example, in the present invention, one can select a restorer gene for breeding a restorer line or one select against a restorer gene for breeding a maintainer (female pool).

The presently described Rf locus on chromosome 1B was mapped to a segment along the chromosome 1B, in an interval of about 15.8 cM, said interval being flanked by markers of SEQ ID NO 2 and SEQ ID NO 8.

Thus, in a first aspect, a method is provided for selecting a cereal plant comprising a functional restorer gene allele for wheat G-type cytoplasmic male sterility or for producing a cereal plant comprising a functional restorer gene allele for wheat G-type cytoplasmic male sterility, comprising the steps of:
  (a) Identifying at least one cereal plant comprising at least one marker allele linked to a functional restorer gene allele for wheat G-type cytoplasmic male sterility located on chromosome 1B; and
  (b) Selecting the plant comprising said at least one marker allele, wherein said plant comprises said functional restorer gene for wheat G-type cytoplasmic male sterility located on chromosome 1B
  wherein said at least one marker allele localises within an interval on chromosome 1B comprising and flanked by the markers of SEQ ID NO 2 and SEQ ID NO 8.

In a second aspect, a method is provided for restoring fertility in a progeny of a G-type cytoplasmic male sterile cereal plant OR for producing a fertile progeny plant from a G-type cytoplasmic male sterile cereal parent plant, comprising the steps of
  (a) Providing a population of progeny plants obtained from crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility located on chromosome 1B;
  (b) Identifying in said population a fertile progeny plant comprising at least one marker allele linked to said functional restorer gene allele for wheat G-type cytoplasmic male sterility, wherein said progeny plant comprises said functional restorer gene allele for wheat G-type cytoplasmic male sterility located on chromosome 1B; and optionally
  (c) Selecting said fertile progeny plant; and optionally
  (d) Propagating the fertile progeny plant,
  wherein said at least one marker allele localises within an interval on chromosome 1B comprising and flanked by the markers of SEQ ID NO 2 and SEQ ID NO 8.

Male sterility in connection with the present invention refers to the failure or partial failure of plants to produce functional pollen or male gametes. This can be due to natural or artificially introduced genetic predispositions or to human intervention on the plant in the field. Male fertile on the other hand relates to plants capable of producing normal functional pollen and male gametes. Male sterility/fertility can be reflected in seed set upon selfing, e.g. by bagging heads to induce self-fertilization. Likewise, fertility restoration can also be described in terms of seed set upon crossing a male sterile plant with a plant carrying a functional restorer gene, when compared to seed set resulting from crossing (or selfing) fully fertile plants.

A male parent or pollen parent, is a parent plant that provides the male gametes (pollen) for fertilization, while a female parent or seed parent is the plant that provides the female gametes for fertilization, said female plant being the one bearing the seeds.

Cytoplasmic male sterility or "CMS" refers to cytoplasmic-based and maternally-inherited male sterility. CMS is total or partial male sterility in plants as the result of specific nuclear and mitochondrial interactions and is maternally inherited via the cytoplasm. Male sterility is the failure of plants to produce functional anthers, pollen, or male gametes although CMS plants still produce viable female gametes. Cytoplasmic male sterility is used in agriculture to facilitate the production of hybrid seed.

"Wheat G-type cytoplasmic male sterility", as used herein refers to the cytoplasm of *Triticum timopheevi* that can confer male sterility when introduced into common wheat (i.e. *Triticum aestivum*), thereby resulting in a plant carrying common wheat nuclear genes but cytoplasm from *Triticum timopheevii* that is male sterile. The cytoplasm of *Triticum timopheevi* (G-type) as inducers of male sterility in common wheat have been extensively studied (Wilson and Ross, Genes Genet. Syst. 1962; Kaul, Male sterility in higher plants. Springer Verlag, Berlin. 1988; Lucken, Hybrid wheat. In Wheat and wheat improvement. Edited by E. G. Heyne. American Society of Agronomy, Madison, Wis, 1987; Mukai and Tsunewaki, Theor. Appl. Genet. 54, 1979; Tsunewaki, Jpn. Soc. Prom. Sci. 1980; Tsunewaki et al., Genes Genet. Syst. 71, 1996). The origin of the CMS phenotype conferred by *T. timopheevi* cytoplasm is with a novel chimeric gene termed orf256, which is upstream of cox1 sequences and is cotranscribed with an apparently normal cox1 gene. Antisera prepared against polypeptide sequences predicted from orf256 recognized a 7-kDa protein present in the CMS line but not in the parental or restored lines (Song and Hedgcoth, Genome 37(2), 1994; Hedgcoth et al., Curr. Genet. 41, 357-365, 2002).

As used herein "a functional restorer gene allele for wheat G-type cytoplasmic male sterility" or "a functional restorer locus for wheat G-type cytoplasmic male sterility" or a "restorer QTL for wheat G-type cytoplasmic male sterility" indicates an allele that has the capacity to restore fertility in the progeny of a cross with a G-type cytoplasmic male sterility ("CMS") line, i.e., a line carrying common wheat nuclear genes but cytoplasm from *Triticum timopheevii*. Restoration against G-type cytoplasm has e.g. been described by Robertson and Curtis (Crop Sci. 9, 1967), Yen et al. (Can. J. Genet. Cytol. 11, 1969), Bahl and Maan (Crop Sci. 13, 1973), Talaat et al. (Egypt. J. Genet. 2, 195-205, 1973) Zhang et al., (2003, supra) Ma and Sorrels (1995, supra), Kojima (1997, supra), Ahmed Talaat et al (2001, supra), Zhou et al (2005, supra). Such restorer genes or alleles are also referred to as Rf genes and Rf alleles.

The term "maintainer" refers to a plant that when crossed with the CMS plant does not restore fertility, and maintains sterility in the progeny. The maintainer is used to propagate the CMS line, and may also be referred to as a non-restorer line. Maintainer lines have the same nuclear genes as the sterile one (i.e. do not contain functional Rf genes), but differ in the composition of cytoplasmic factors that cause male sterility in plants i.e. maintainers have "fertile" cytoplasm. Therefore when a male sterile line is crossed with its maintainer progeny with the same male sterile genotype will be obtained.

The term "cereal" relates to members of the monocotyledonous family Poaceae which are cultivated for the edible components of their grain. These grains are composed of endosperm, germ and bran. Maize, wheat and rice together account for more than 80% of the worldwide grain production. Other members of the cereal family comprise rye, oats, barley, *triticale*, sorghum, wild rice, spelt, einkorn, emmer, durum wheat and kamut.

In one embodiment, a cereal plant according to the invention is a cereal plant that comprises at least a B genome or related genome, such as wheat (*Triticum aestivum*; ABD), spelt (*Triticum spelta*; ABD) durum (*T. turgidum*; AB), barley (*Hordeum vulgare*; H) and rye (*Secale cereale*; R). In a specific embodiment, the cereal plant according to the invention is wheat (*Triticum aestivum*; ABD).

A "molecular marker" or "marker" or "marker nucleic acid" or "genetic marker", as used herein, refers to a polymorphic locus, i.e. a polymorphic nucleotide (a so-called single nucleotide polymorphism or SNP) or a polymorphic DNA sequence at a specific locus. A marker refers to a measurable, genetic characteristic with a fixed position in the genome, which is normally inherited in a Mendelian fashion, and which can be used for mapping of a trait of interest or to identify certain individuals with a certain trait of interest. A marker thus refers to a gene or nucleotide sequence that can be used to identify plants having a particular allele, e.g., the presently described Rf alleles on chromosome 1B. A marker may be described as a variation at a given genomic locus. It may be a short DNA sequence, such as a sequence surrounding a single base-pair change (single nucleotide polymorphism, or "SNP"), or a long one, for example, a microsatellite/simple sequence repeat ("SSR"). A molecular marker may also include 'Indels' which refers to the insertion or the deletion of bases or a combination of both in the DNA of an organism, and which can be used as molecular markers.

The term "marker genotype" refers to the combination of marker alleles present at a polymorphic locus on each chromosome of the chromosome pair. The term "marker allele" refers to the version of the marker that is present in a particular plant at one of the chromosomes. Typically, a marker can exist as or can be said to have or to comprise two marker alleles. The term "haplotype", as used herein, refers to a specific combination of marker alleles as present within a certain plant or group of (related) plants. See also the below definitions of a SNP (marker) genotype and SNP (marker) allele.

A "marker context" or "marker context sequence", as used herein, refers to 50-150 bp upstream of a marker, such as a SNP marker, and/or 50-150 bp downstream of such a marker. The marker context of the herein described (SNP) markers is given in the sequence listing, flanking the SNP position. The upstream and downstream sequences of a (SNP) marker can also be referred to as (upstream and/or downstream) flanking sequences.

Identifying a cereal plant comprising at least one marker allele linked to a functional restorer gene allele for wheat G-type cytoplasmic male sterility located on chromosome 1B can be accomplished using a molecular marker assay that detects the presence of at least one such marker allele, e.g. the marker alleles described herein that are linked to the functional restorer gene allele for wheat G-type cytoplasmic male sterility located on chromosome 1B. This can involve obtaining or providing a biological sample, i.e. plant material, or providing genomic DNA of a plant, and analyzing the genomic DNA of the material for the presence of at least one of said marker alleles (or the marker genotype for at least one of such markers). In this method also other molecular marker tests described elsewhere herein can be used.

As will be well known to a person skilled in the art, markers and marker assays include for example Restriction Fragment Length Polymorphisms (RFLPs), Random Amplified Polymorphic DNA's (RAPDs), Amplified Fragment Length Polymorphism's (AFLPs), DAF, Sequence Characterized Amplified Regions (SCARs), microsatellite or Simple Sequence Repeat markers (SSRs), Sequence Characterized Amplified Regions (SCARs), single-nucleotide polymorphisms (SNPs), KBioscience Competitive Allele-Specific PCR (KASPar), as inter alia described in Jonah et al. (Global Journal of Science Frontier Research 11:5, 2011) and Lateef (Journal of Biosciences and Medicines, 2015, 3, 7-18).

As used herein, the term "single nucleotide polymorphism" (SNP) may refer to a DNA sequence variation occurring when a single nucleotide in the genome (or other shared sequence) differs between members of a species or paired chromosomes in an individual. [0057] Within a population, SNPs can be assigned a minor allele frequency the lowest allele frequency at a locus that is observed in a particular population. This is simply the lesser of the two allele frequencies for single-nucleotide polymorphisms. There are variations between various populations, so a SNP allele that is common in one geographical group or variety may be much rarer in another.

Single nucleotide polymorphisms may fall within coding sequences of genes, non-coding regions of genes, or in the intergenic regions between genes. SNPs within a coding sequence will not necessarily change the amino acid sequence of the protein that is produced, due to degeneracy of the genetic code. A SNP in which both forms lead to the same polypeptide sequence is termed "synonymous" (sometimes referred to a silent mutation). If a different polypeptide sequence is produced, they are termed "non-synonymous." A non-synonymous change may either be mis-sense or nonsense, where a mis-sense change results in a different amino acid and a nonsense change results in a premature stop codon. SNPs that are not in protein-coding regions may still have consequences for e.g. gene splicing, transcription factor binding, or the sequence of non-coding RNA (e.g. affecting transcript stability, translation). SNPs are usually biallelic and thus easily assayed in plants and animals.

A particularly useful assays for detection of SNP markers is for example KBioscience Competitive Allele-Specific PCR (KASP, see www.kpbioscience.co.uk), For developing the KASP-assay 70 base pairs upstream and 70 basepairs downstream of the SNP are selected and two allele-specific forward primers and one allele specific reverse primer is designed. See e.g. Allen et al. 2011, Plant Biotechnology J. 9, 1086-1099, especially p 1097-1098 for KASP assay method.

The terms "linked to" or "linkage", as used herein, refers to a measurable probability that genes or markers located on a given chromosome are being passed on together to individuals in the next generation. Thus, the term "linked" may refer to one or more genes or markers that are passed together with a gene with a probability greater than 0.5 (which is expected from independent assortment where markers/genes are located on different chromosomes). Because the proximity of two genes or markers on a chromosome is directly related to the probability that the genes or markers will be passed together to individuals in the next generation, the term "linked" may also refer herein to one or more genes or markers that are located within about 50 centimorgan (cM) or less of one another on the same chromosome. Genetic linkage is usually expressed in terms of cM. Centimorgan is a unit of recombinant frequency for measuring genetic linkage, defined as that distance between genes or markers for which one product of meiosis in 100 is recombinant, or in other words, the centimorgan is equal to a 1% chance that a marker at one genetic locus on a chromosome will be separated from a marker at a second locus due to crossing over in a single generation. It is often used to infer distance along a chromosome. The number of base-pairs to which cM correspond varies widely across the genome (different regions of a chromosome have different propensities towards crossover) and the species (i.e. the total size of the genome).

The presently described Rf locus on chromosome 1B was mapped to a segment at chromosome 1B, in an interval of about 15.8 cM, said interval being flanked by markers of SEQ ID NO 2 and SEQ ID NO 8. These and any marker located in between can be said to comprise an allele that is linked to functional restorer gene for wheat G-type cytoplasmic male sterility located on chromosome 1B Thus, in this respect, the term linked can be a separation of about 15.8 cM, or less such as about 12.5 cm, about 10 cM, 7.5 cM, about 6 cM, about 5 cM, about 4 cM, about 3 cM, about 2.5 cM, about 2 cM, or even less. Particular examples of markers comprising an allele linked to the functional restorer gene for wheat G-type cytoplasmic male sterility located on chromosome 1B are specified in table 1. The peak marker was the marker of SEQ ID NO. 6.

Further finemapping narrowed the 1B region to an interval of about 1.25 cM (from 6.8 to 8.05 cM), comprising the markers as represented by SEQ ID NO. 11, SEQ ID NO. 12, SEQ ID NO. 12 and SEQ ID NO. 14. These and any further marker located in said interval can be said to comprise an allele that is "tightly linked" to the functional restorer gene for wheat G-type cytoplasmic male sterility located on chromosome 1B. Thus, the term "tightly linked" as used herein can be a separation of about 1.25 cM, or even less, such as about about, 1.0 cM, about 0.95 cM, about 0.9 cM, about 0.85 cM, about 0.8 cM, about 0.75 cM, about 0.5 cM, about 0.4 cM, about 0.3 cM, about 0.25 cM, about 0.20 cM, about 0.15 cM, about 0.10 cM, or even less. Particular examples of markers comprising an allele tightly linked to the functional restorer gene for wheat G-type cytoplasmic male sterility located on chromosome 1B are given in table 2. The marker closest to the peak was SEQ ID NO. 13.

Thus, said at least one marker allele linked to said functional restorer gene allele located on chromosome 1B can be selected from any one of:
 a. a T at SEQ ID NO: 2;
 b. a C at SEQ ID NO: 3;
 c. a T at SEQ ID NO: 4;
 d. a T at SEQ ID NO: 5;
 e. an A at SEQ ID NO: 6;
 f. an A at SEQ ID NO: 7;
 g. a G at SEQ ID NO: 8;
 h. a C at SEQ ID NO: 11;
 i. an A at SEQ ID NO: 12,
 j. a T at SEQ ID NO: 13;
 k. a T at SEQ ID NO: 14,
or any combination thereof.

As used herein, "a T at SEQ ID NO: 2" or "a C at SEQ ID NO. 3" and the like, refers to a T or a C etc being present at a position corresponding to the position of the SNP in said SEQ ID NO, as e.g. indicated in table 1 or 2. This can for example be determined by alignment of the genomic sequence with said SEQ ID NO. Thus, "a T at SEQ ID NO: 2" means "a T at a position corresponding to position 51 of SEQ ID NO: 2", etc.

In a further embodiment, said at least one marker allele localises to an interval from 6.8 to 8.05 cM on chromosome 1B. Said 1.25 cM interval comprises the markers of SEQ ID NO. 11, SEQ ID NO. 12, SEQ ID NO. 13 and SEQ ID NO. 14 at the positions as indicated in table 2.

For example, said at least one marker allele linked to said functional restorer gene allele can be selected from any one of:
 a. a C at SEQ ID NO: 11;
 b. an A at SEQ ID NO: 12,
 c. a T at SEQ ID NO: 13;
 d. a T at SEQ ID NO: 14,
or any combination thereof.

In an even further embodiment, said at least one marker allele linked to said functional restorer gene for wheat G-type cytoplasmic male sterility located on chromosome 1B localises to an interval of 0.95 cM (from 7.1 to 8.05 cM) on chromosome 1B flanked by and comprising the marker pair of SEQ ID NO. 11 and SEQ ID NO. 14.

In a particular embodiment, said at least one marker allele linked to said functional restorer gene allele is a T at SEQ ID NO. 13.

The term "interval" refers to a continuous linear span of chromosomal DNA with termini defined by map position and/or markers. For example, the interval comprising and flanked by the marker pair of SEQ ID NO: 11 and SEQ ID NO: 14. comprises the specifically mentioned flanking markers and the markers located in between, e.g. SEQ ID NO: 12 and 13 as listed in table 2 below. The interval comprising and flanked by the marker pair of SEQ ID NO: 2 and SEQ ID NO: 8 comprises the markers of SEQ ID NO: 3 to 7 as well as the markers of SEQ ID NO: 11-14. Accordingly, a flanking marker as used herein, is a marker that defines one of the termini of an interval (and is included in that interval). It will be clear that any of such intervals may comprise further markers not specifically mentioned herein.

The position of the chromosomal segments identified, and the markers thereof, when expressed as recombination frequencies or map units, are provided herein as a matter of general information. The embodiments described herein were obtained using particular wheat populations. Accordingly, the positions of particular segments and markers as map units are expressed with reference to the used populations. It is expected that numbers given for particular segments and markers as map units may vary from cultivar to cultivar and are not part of the essential definition of the DNA segments and markers, which DNA segments and markers are otherwise described, for example, by nucleotide sequence.

A locus (plural loci), as used herein refers to a certain place or position on the genome, e.g. on a chromosome or chromosome arm, where for example a gene or genetic marker is found. A QTL (quantitative trait locus), as used herein, and refers to a position on the genome that corresponds to a measurable characteristic, i.e. a trait, such as the presently described Rf loci.

As used herein, the term "allele(s)", such as of a gene, means any of one or more alternative forms of a gene at a particular locus. In a diploid cell of an organism, alleles of a given gene are located at a specific location or locus (loci plural) on a chromosome. One allele is present on each chromosome of the pair of homologous chromosomes or possibly on homeologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In tetraploid species, two sets of diploid genomes exist, whereby the chromosomes of the two genomes are referred to as "homeologous chromosomes" (and similarly, the loci or genes of the two genomes are referred to as homeologous loci or genes). Likewise, hexaploid species have three sets of diploid genomes, etc. A diploid, tetraploid or hexaploid plant species may comprise a large number of different alleles at a particular locus. The ploidy levels of domesticated wheat species range from diploid (*Triticum monococcum*, 2n=14, AA), tetraploid (*T. turgidum*, 2n=28, AABB) to hexaploid (*T. aestivum*, 2n=42, AABBDD).

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

An allele of a particular gene or locus can have a particular penetrance, i.e. it can be dominant, partially dominant, co-dominant, partially recessive or recessive. A dominant allele is a variant of a particular locus or gene that when present in heterozygous form in an organism results in the same phenotype as when present in homozygous form. A recessive allele on the other hand is a variant of an allele that in heterozygous form is overruled by the dominant allele thus resulting in the phenotype conferred by the dominant allele, while only in homozygous form leads to the recessive phenotype. Partially dominant, co-dominant or partially recessive refers to the situation where the heterozygote displays a phenotype that is an intermediate between the phenotype of an organism homozygous for the one allele and an organism homozygous for the other allele of a particular locus or gene. This intermediate phenotype is a demonstration of partial or incomplete dominance or penetrance. When partial dominance occurs, a range of phenotypes is usually observed among the offspring. The same applies to partially recessive alleles.

Cytoplasmic male-sterililty is caused by one or more mutations in the mitochondrial genome (termed "sterile cytoplasm") and is inherited as a dominant, maternally transmitted trait. For cytoplasmic male sterility to be used in hybrid seed production, the seed parent must contain a sterile cytoplasm and the pollen parent must contain (nuclear) restorer genes (Rf genes) to restore the fertility of the hybrid plants grown from the hybrid seed. Accordingly, also such Rf genes preferably are at least partially dominant, most preferably dominant, in order to have sufficient restoring ability in offspring.

A chromosomal interval flanked by the above mentioned markers, are for example the markers as listed in Table 1-2 below between the specifically mentioned markers, or other markers that are not explicitly shown, but which are also flanked by the marker pairs mentioned. The skilled person can easily identify new markers in the genomic region or subgenomic region being flanked by any of the marker pairs listed above. Such markers need not to be SNP markers, but can be any type of genotypic or phenotypic marker mapped to that genomic or subgenomic region. Preferably such markers are genetically and physically linked to the presently described Rf loci as present in (and as derivable from) at least Accession number PI 583676 (USDA National Small Grains Collection), but preferably also as present in other cereals comprising the Rf 1B locus. In other words, the markers are preferably indicative of the presence of the Rf locus in a non-source specific manner.

In a further embodiment, at least two, three, four, or more marker alleles linked to said functional restorer gene for wheat G-type cytoplasmic male sterility located on chromosome 1B can be used, such as, at least two, three, four, or more marker nucleic acids selected from any one of SEQ IN NO. 2, SEQ ID NO. 3, SEQ ID NO. 4, SEQ ID NO. 5, SEQ ID NO. 6, SEQ ID NO. 7, SEQ ID NO. 8, SEQ ID NO. 11, SEQ ID NO. 12, SEQ ID NO. 13, SEQ ID NO. 14.

In a further embodiment, at least two, three, four, or more contiguous marker alleles linked to said functional restorer gene for wheat G-type cytoplasmic male sterility located on chromosome 1B may be used. A contiguous marker, as used herein is a nucleotide sequence located "upstream" or "downstream" of another marker, depending on whether the contiguous nucleotide sequence from the chromosome is on the 5' or the 3' side of the original marker, as conventionally understood, e.g. in the order as listed in table 1 or 2.

Integration of the fine map with partial genome sequences identified scaffold as represented by SEQ ID NO. 15 as harboring the functional restorer gene allele. Thus, in any of the herein described embodiments or aspects, the functional restorer gene allele for wheat G-type cytoplasmic male sterility located on chromosome 1B may localize to the genome scaffold as represented by SEQ ID NO. 15.

A "contig", as used herein refers to set of overlapping DNA segments that together represent a consensus region of DNA. In bottom-up sequencing projects, a contig refers to overlapping sequence data (reads); in top-down sequencing projects, contig refers to the overlapping clones that form a physical map of the genome that is used to guide sequencing and assembly. Contigs can thus refer both to overlapping DNA sequence and to overlapping physical segments (fragments) contained in clones depending on the context.

A "scaffold" as, used herein, refers to overlapping DNA contigs that together represent a consensus region of DNA.

In a further embodiment, said functional restorer gene allele is a functional allele of a gene encoding a pentatricopeptide repeat (PPR) protein (i.e. a PPR gene) localising within any of the above intervals or to said scaffold.

PPR proteins are classified based on their domain architecture. P-class PPR proteins possess the canonical 35 amino acid motif and normally lack additional domains. Members of this class have functions in most aspects of organelle gene expression. PLS-class PPR proteins have three different types of PPR motifs, which vary in length; P (35 amino acids), L (long, 35-36 amino acids) and S (short, ~31 amino acids), and members of this class are thought to mainly function in RNA editing. Subtypes of the PLS class are categorized based on the additional C-terminal domains they possess (reviewed by Manna et al., 2015, Biochimie 113, p 93-99, incorporated herein by reference).

Most fertility restoration (Rf) genes come from a small clade of genes encoding pentatricopeptide repeat (PPR) proteins (Fuji et al., 2011, PNAS 108(4), 1723-1728—herein incorporated by reference). PPR genes functioning as fertility restoration (Rf) genes are referred to in Fuji (supra) as Rf-PPR genes. Rf-PPR genes are usually present in clusters of similar Rf-PPR-like genes, which show a number of characteristic features compared with other PPR genes. They are comprised primarily of tandem arrays of 15-20 PPR motifs, each composed of 35 amino acids.

Most Rf PPR genes belong to the P-class PPR subfamily, although also PLS-class PPR Rf genes have been identified, and are characterized by the presence of tandem arrays of 15 to 20 PPR motifs each composed of 35 amino acid residues. High substitution rates observed for particular amino acids within otherwise very conserved PPR motifs, indicating diversifying selection, prompted the conclusion that these residues might be directly involved in binding to RNA targets. This has led to the development of a "PPR code" which allows the prediction of RNA targets of naturally occurring PPR proteins as well as the design of synthetic PPR proteins that can bind RNA molecules of interest, whereby sequence specificity is ensured by distinct patterns of hydrogen bonding between each RNA base and the amino acid side chains at positions 5 and 35 in the aligned PPR motif (Melonek et al., 2016, Nat Sci Report 6:35152, Barkan et al., 2012, PLoS Genet 8(8): e1002910, both incorporated herein by reference).

Accordingly, a functional allele of a PPR gene, as used herein, refers to an allele of a PPR gene that is a functional restorer gene allele for wheat G-type cytoplasmic male sterility as described herein, i.e. that when expressed in a (sexually compatible) cereal plant has the capacity to restore fertility in the progeny of a cross with a G-type cytoplasmic male sterile cereal plant. Such a functional allele of a PPR gene is also referred to as a PPR-Rf gene (or Rf-PPR gene), which in turn encodes a PPR-Rf (or Rf-PPR) protein.

In one embodiment, said functional restorer gene allele encodes a polypeptide, such as a PPR protein that has the capacity to (specifically) bind to the CMS ORF256 (SEQ ID NO. 23). Bind to or specifically bind to or (specifically) recognize, as used herein, means that according to the above described PPR code, the PPR protein contains a number of PPR motifs with specific residues at positions 5 and 35 and which are ordered in such a way so as to be able to bind to a target mRNA, in this case the ORF256 mRNA, in a sequence-specific or sequence-preferential manner.

For example, the functional restorer gene allele can encode a PPR protein containing PPR motifs with specific residues at the above indicated positions so as to recognize the target sequence AACTGTTTCTATTTGCAC of ORF256 (nt 129-146 of SEQ ID NO. 23). In one example, the predicted recognition sequence can be AUUUK-CASNCNYACGU (SEQ ID NO. 22).

In a further embodiment, said functional restorer gene allele is a functional allele of a PPR gene encoded by SEQ ID NO. 16, SEQ ID NO 18, SEQ ID NO. 19, SEQ ID NO 21, or a PPR gene encoding the polypeptide of SEQ ID NO. 17 or SEQ ID NO. 20. For example, said functional restorer gene allele can comprise or encode a sequence that is substantially identical to SEQ ID NO. 16, SEQ ID NO 17, SEQ ID NO 18, SEQ ID NO. 19, SEQ ID NO 20, SEQ ID NO. 21 as defined herein, such as at least 85%, 85.5%, 86%, 87%, 88%, 89%, 90%, 91%, 92%, 93%, 94%, 95%, 96%, 97%, 98%, 99% or 99.5% identical to SEQ ID NO. 16, SEQ ID NO 17, SEQ ID NO 18, SEQ ID NO. 19, SEQ ID NO 20, SEQ ID NO. 21.

In a further embodiment, said functional restorer gene allele is a functional restorer gene allele as present in (and as derivable from) at least Accession number PI 583676 (USDA National Small Grains Collection, also known as Dekalb 582M and registered as US PVP 7400045).

In an even further embodiment, said functional restorer gene allele comprises the nucleotide sequence of SEQ ID NO.16, SEQ ID NO 18, SEQ ID NO. 19, SEQ ID NO 21 or encodes the polypeptide of SEQ ID NO. 17 or SEQ ID NO.20.

It will be clear that when reference herein is made to a certain SNP genotype or SNP allele (or marker genotype or marker allele) in a specific genomic sequence (selected e.g. from SEQ ID NO: 1 to SEQ ID NO: 14, or fragments thereof), this encompasses also the SNP genotype or allele in variants of the genomic sequence, i.e. the SNP genotype or allele in a genomic sequence that are homologous, e.g. comprising at least 90%, 95%, 98%, 99% (substantial) sequence identity or more to the sequence referred to (selected e.g. from SEQ ID NO: 1 to SEQ ID NO: 14, or fragments thereof). Thus any reference herein to any one of SEQ ID NO: 1 to 14 (or fragments thereof) in one aspect also encompasses a variant of any one of SEQ ID NO: 1 to 14 (or fragments thereof), said variant (homologous sequence) comprising at least 85%, 90%, 95%, 98%, 99% sequence identity or more to said sequence (using e.g. the program 'Needle'), but comprising said SNP (marker) genotype or allele.

The SNP genotype refers to two nucleotides, and genomic sequences comprising one of these two nucleotides, one on each chromosome of the chromosome pair. So a plant having e.g. a AA genotype for SEQ ID NO. 6 has an identical nucleotide (A) on both chromosomes at the position corresponding to nucleotide 32 of SEQ ID NO. 6, while a plant having an AG genotype for SEQ ID NO. 6 has one chromosome with an A at the position corresponding to nucleotide 32 of SEQ ID NO. 6 and one chromosome with a G at said nucleotide position. Accordingly, a SNP allele refers to one of the two nucleotides of the SNP genotype as present on a chromosomes.

Based on the present disclosure, the skilled person can easily identify any further Rf specific marker or marker alleles as listed above. This can for example be done by sequencing genomic regions in-between any of the markers mentioned herein or by mapping new markers to a region in between any of the marker intervals or sub-intervals listed above. Preferably, but not necessarily, such markers are common markers, i.e. they are present on chromosome 1B of more than one Rf source.

The invention further describes a method for producing a cereal (e.g. wheat) plant comprising a functional restorer gene allele for wheat G-type cytoplasmic male sterility, comprising the steps of a. crossing a first cereal plant comprising a functional restorer gene for wheat G-type cytoplasmic male sterility located on chromosome 1B, with a second plant (wherein said first plant comprises at least one marker allele linked to a functional restorer gene allele for wheat G-type cytoplasmic male sterility located on chromosome 1B as described herein, and hence is identifiable using the methods described herein)

b. identifying (and optionally selecting) a progeny plant comprising a functional restorer gene allele for wheat G-type cytoplasmic male sterility located on chromosome 1B according to any of the methods described herein, by identifying a progeny plant comprising at least one marker allele linked to a functional restorer gene allele for wheat G-type cytoplasmic male sterility located on chromosome 1B as described herein (wherein said progeny plant comprises said functional restorer gene for wheat G-type cytoplasmic male sterility located on chromosome 1B).

Also provided is a method for producing a cereal plant comprising a functional restorer gene allele for wheat G-type cytoplasmic male sterility located on chromosome 1B, comprising the steps of
   a. crossing a first cereal plant homozygous for a functional restorer gene for wheat G-type cytoplasmic male sterility located on chromosome 1B with a second cereal plant (wherein said first cereal plant comprises at least one marker allele linked to a functional restorer gene allele for wheat G-type cytoplasmic male sterility located on chromosome 1B as described herein, preferably wherein said plant is homozygous for said at least one marker allele)
   b. obtaining a progeny plant, wherein said progeny plant comprises a functional restorer gene allele for wheat G-type cytoplasmic male sterility located on chromosome 1B (wherein said progeny plant comprises at least one marker allele linked to a functional restorer gene allele for wheat G-type cytoplasmic male sterility located on chromosome 1B as described herein, and hence is identifiable using the methods described herein).

Said second plant can be a plant not comprising a functional restorer gene for wheat G-type cytoplasmic male sterility located on chromosome 1B.

In an even further embodiment, the invention provides a method for producing F1 hybrid seeds or F1 hybrid plants, comprising the steps of:
   a. Providing a male cereal (e.g. wheat) parent plant comprising a functional restorer gene allele for wheat G-type cytoplasmic male sterility located on chromosome 1B;
   b. Crossing said male parent plant with a female cereal (e.g. wheat) parent plant, wherein the female parent plant is a G-type cytoplasmic male sterile cereal plant;
   c. Optionally collecting hybrid seeds from said cross.

The F1 hybrid seeds and plants preferably comprise at least one marker allele linked to a functional restorer gene allele for wheat G-type cytoplasmic male sterility located on chromosome 1B as described herein, and the F1 plants grown from the seeds are therefore fertile. Preferably, the male parent plant is thus homozygous for said a functional restorer gene allele for wheat G-type cytoplasmic male sterility located on chromosome 1B and hence is also homozygous for said at least one marker allele.

In the above method, the male parent plant used for crossing can be selected using any of the herein described methods for selecting a cereal plant comprising a functional restorer gene for wheat G-type cytoplasmic male sterility. Accordingly, the male parent plant comprises at least one marker allele linked to a functional restorer gene allele for wheat G-type cytoplasmic male sterility located on chromosome 1B, preferably in homozygous form.

The invention also provides cereal plants, such as wheat plants, obtained by any of the above methods, said cereal plant comprising at least one marker allele linked to the functional restorer gene allele for wheat G-type cytoplasmic male sterility located on chromosome 1B.

Said at least one marker allele linked to the functional restorer gene allele for wheat G-type cytoplasmic male sterility located on chromosome 1B may localize to the same chromosomal intervals or contigs and can be selected from the same groups as described above for the other embodiments and aspect.

Also described is a cereal plant, plant part, plant cell or seed comprising at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1B, wherein said at least one marker allele localises within an interval on chromosome 1B comprising and flanked by the markers of SEQ ID NO 2 and SEQ ID NO 8, preferably wherein said plant comprises at least one of (such as one, two, three, four five, six, seven, eight, nine, ten or all of):
   a. a T at SEQ ID NO: 2;
   b. a C at SEQ ID NO: 3;
   c. a T at SEQ ID NO: 4;
   d. a T at SEQ ID NO: 5;
   e. an A at SEQ ID NO: 6;
   f. an A at SEQ ID NO: 7;
   g. a G at SEQ ID NO: 8;
   h. a C at SEQ ID NO: 11;
   i. an A at SEQ ID NO: 12,
   j. a T at SEQ ID NO: 13;
   k. a T at SEQ ID NO: 14,
said plant not comprising any one or all of
   l. an A at SEQ ID NO: 1;
   m. a T at SEQ ID NO: 9.

Also described is cereal plant, plant part, plant cell or seed comprising at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1B, wherein said at least one marker allele localises within an interval on chromosome 1B comprising and flanked by the markers of SEQ ID NO 11 and SEQ ID NO 14, preferably wherein said plant comprises at least one of (such as one, two, three or all of):
   a. a C at SEQ ID NO: 11;
   b. an A at SEQ ID NO: 12,
   c. a T at SEQ ID NO: 13;
   d. a T at SEQ ID NO: 14,
   said plant not comprising any one or all of
   e. a T at SEQ ID NO: 2;
   f. an A at SEQ ID NO: 8.

Also described are a cereal plant, plant part, plant cell or seed comprising at least one functional restorer gene allele for wheat G-type cytoplasmic male sterility located on chromosome 1B, said plant comprising at least one marker allele linked to a functional restorer gene allele for wheat G-type cytoplasmic male sterility located on chromosome 1B wherein said at least one marker allele localises within an interval on chromosome 1B comprising and flanked by the markers of SEQ ID NO 11 and SEQ ID NO 14, preferably wherein said plant comprises at least one of (such as one, two, three or all of):
   a. a C at SEQ ID NO: 11;
   b. an A at SEQ ID NO: 12,
   c. a T at SEQ ID NO: 13;
   d. a T at SEQ ID NO: 14,
   said plant not comprising any one or all of e. a T at SEQ ID NO: 10;
f. a T at SEQ ID NO: 5.

In a further embodiment, any of the above plants plant part, plant cell or seeds comprises a T at SEQ ID NO. 13. In a further embodiment, said plant comprising a T at SEQ ID NO 13, does not comprise any one or all of: a C at SEQ ID NO: 11; an A at SEQ ID NO: 12; a T at SEQ ID NO: 14.

Also provided are plant parts, plant cells and seed from the cereal plants according to the invention comprising said at least one marker allele and said functional restorer gene allele. The plants, plant parts, plant cells and seeds of the invention may also be hybrid plants, plant parts, plant cells or seeds.

Also provided is a method to determine the presence or absence or zygosity status of a functional restorer gene allele for wheat G-type cytoplasmic male sterility located on chromosome 1B in a biological sample of a cereal plant, comprising providing genomic DNA from said biological sample, and analysing said DNA for the presence or absence or zygosity status of at least one marker allele linked to a functional restorer gene for wheat G-type cytoplasmic male sterility located on chromosome 1B a described herein. It will be clear that the presence can be determined using a marker allele linked to the functional restorer gene as described herein, whereas the absence can (additionally) be determined by detecting the presence of the other, non-restoring allele. The zygosity status, i.e. whether the plant is homozygous for the restorer allele, homozygous for the non-restorer allele or heterozygous (i.e. the Rf genotype), can be determined by detecting the presence or absence of a marker allele linked to the functional restorer gene and by detecting the presence of the other, non-restoring allele, but depending on the parental origin it can also be sufficient to determine the presence or absence of only one of the alleles to be able to deduce the complete genotype (zygosity status) of the plant.

Also provided is a method for the identification and/or selection of a cereal (e.g. wheat) plant comprising a functional restorer gene allele for wheat G-type cytoplasmic male sterility comprising the steps of
a. Identifying or detecting in said plant the presence of the nucleic acid or the polypeptide encoding a functional restorer gene for wheat G-type cytoplasmic male sterility as described herein
b. and optionally selecting said plant comprising said nucleic acid or polypeptide.

Likewise, identifying or detecting can involve obtaining a biological sample (e.g. protein) or genomic DNA and determining the presence of the nucleic acid or polypeptide according to methods well known in the art, such as hybridization, PCR, Rt-PCR, Southern blotting, Southern-by-sequencing, SNP detection methods (e.g. as described herein), western blotting, elisa etc, e.g. based on the sequences provided herein.

The invention also provides the use of at least one marker comprising an allele linked to the functional restorer gene for wheat G-type cytoplasmic male sterility located on chromosome 1B for the identification of at least one further marker comprising an allele linked to said functional restorer gene for wheat G-type cytoplasmic male sterility located on chromosome 1B. Such markers are also genetically linked or tightly linked to the restorer gene, and are also within the scope of the invention. Markers can be identified by any of a variety of genetic or physical mapping techniques. Methods of determining whether markers are genetically linked to a restore gene are known to those of skill in the art and include, for example, interval mapping (Lander and Botstein, (1989) Genetics 121:185), regression mapping (Haley and Knott, (1992) Heredity 69:315) or MQM mapping (Jansen, (1994) Genetics 138:871), rMQM mapping. In addition, such physical mapping techniques as chromosome walking, contig mapping and assembly, amplicon resequencing, transcriptome sequencing, targeted capture and sequencing, next generation sequencing and the like, can be employed to identify and isolate additional sequences useful as markers in the context of the present invention.

The invention further provides the use of at least one marker allele linked to a functional restorer gene for wheat G-type cytoplasmic male sterility located on chromosome 1B as described herein for the identification of a plant a comprising said functional restorer gene for wheat G-type cytoplasmic male sterility.

Also provided is the use of a plant obtained by any of the methods as described herein and comprising at least one marker allele linked to a functional restorer gene for wheat G-type cytoplasmic male sterility located on chromosome 1B as described herein, for restoring fertility in a progeny of a G-type cytoplasmic male sterile cereal plant, such as a wheat plant, or for producing a population of hybrid cereal plants, such as a wheat plants or for producing hybrid seed.

Further provided is a method for identifying a functional restorer gene allele for wheat G-type cytoplasmic male sterility located on chromosome 1B, comprising the steps of
a. Providing a population of F2 plants resulting from selfing of a population of F1 plants obtained by crossing a female cereal parent plant with a male cereal parent plant, wherein the female parent plant is a G-type cytoplasmic male sterile cereal plant, and wherein the male parent plant comprises a functional restorer gene allele for wheat G-type cytoplasmic male sterility located on chromosome 1B.
b. Classifying the fertility of a plurality of said F2 plants.
c. Determining the nucleotide sequence of at least part of the region of chromosome 1B comprising and flanked by the markers of SEQ ID NO 2 and SEQ ID NO 8 of genomic DNA isolated from each of said plurality of F2 plants.
d. Identifying the coding sequence within said region having the highest association to the phenotype of restored fertility, wherein the identified coding sequence is the functional restorer gene allele for wheat G-type cytoplasmic male sterility located on chromosome 1B.

In any of the above described methods or uses, the markers and marker alleles can localize to the same chromosomal intervals and can be selected from the same groups as described above for the other embodiments and aspect.

Also provided are any of the markers comprising an allele linked to the functional restorer gene for wheat G-type cytoplasmic male sterility located on chromosome 1B, as described herein.

Also provided herein is a chromosome fragment, which comprises a functional restorer gene for wheat G-type cytoplasmic male sterility located on chromosome 1B, as described throughout the specification. In one aspect the chromosome fragment is isolated from its natural environment. In another aspect it is in a plant cell, especially in a cereal cell, especially in a wheat cell. Also an isolated part of the chromosome fragment comprising the functional restorer gene for wheat G-type cytoplasmic male sterility located on chromosome 1B is provided herein. Such a chromosome fragment can for example be a contig or a scaffold, such as corresponding to SEQ ID NO. 16.

Further provided is a recombinant nucleic acid molecule, especially a recombinant DNA molecule, which comprises a functional restorer gene according to the invention. In one aspect the functional restorer gene is detectable by one or more of the molecular marker assays described herein. Also a DNA vector is provided comprising the recombinant DNA. The recombinant DNA molecule or DNA vector may be an isolated nucleic acid molecule. The DNA comprising the functional restorer gene may be in a microorganism, such as a bacterium (e.g. *Agrobacterium* or *E. coli*).

Thus, in one embodiment, the invention provides an (isolated) nucleic acid molecule encoding a functional restorer gene allele for wheat G-type cytoplasmic male sterility, wherein said functional restorer gene allele localises within an interval on chromosome 1B comprising and flanked by the markers of SEQ ID NO 2 and SEQ ID NO 8. Thus, the (isolated) nucleic acid molecule encodes or comprises a functional restorer gene allele for wheat G-type cytoplasmic male sterility that is derivable or derived from an interval on chromosome 1B comprising and flanked by the markers of SEQ ID NO 2 and SEQ ID NO 8. Said functional restorer gene allele can be identified and hence is identifiable using any of the markers and marker alleles linked to said functional restorer gene allele as described herein.

In a further embodiment, said functional restorer gene allele encoded by said (isolated) nucleic acid molecule localizes within an interval on chromosome 1B comprising and flanked by the markers of SEQ ID NO 11 and SEQ ID NO 14.

In a further embodiment, said functional restorer gene allele encoded by said (isolated) nucleic acid molecule localizes to the contig as represented by SEQ ID NO 15.

In a further embodiment, said functional restorer gene allele encoded by said (isolated) nucleic acid molecule can be a functional allele of a PPR gene localising within any of said intervals or to said contig.

In one embodiment, said (isolated) nucleic acid encoding said functional restorer gene allele encodes a(n) (isolated) polypeptide, such as a PPR protein, that has the capacity to (specifically) bind to the CMS ORF256 (SEQ ID NO. 22). Bind to or specifically bind to or (specifically) recognize, as used herein, means that according to the above described PPR code, the PPR protein contains a number of PPR motifs with specific residues at positions 5 and 35 and which are ordered in such as way so as to be able to bind to a target mRNA, in this case the ORF256 mRNA, in a sequence-specific or sequence-preferential manner.

For example, the functional restorer gene allele can encode a(n) (isolated) PPR protein containing PPR motifs with specific residues at the above indicated positions so as to recognize the target sequence AACTGTTTCTAT-TTGCAC of ORF256 (nt 129-146 of SEQ ID NO. 23). In one example, the predicted recognition sequence can be AUUUKCASNCNYACGU (SEQ ID NO. 21).

The functional restorer gene allele can also encode a PPR protein which when expressed is targeted to the mitochondrion. This can e.g. be accomplished by the presence of a (plant-functional) mitochondrial targeting sequence or mitochondrial signal peptide, or mitochondrial transit peptide. A mitochondrial targeting signal is a 10-70 amino acid long peptide that directs a newly synthesized protein to the mitochondria, typically found at the N-terminus. Mitochondrial transit peptides are rich in positively charged amino acids but usually lack negative charges. They have the potential to form amphipathic a-helices in nonaqueous environments, such as membranes. Mitochondrial targeting signals can contain additional signals that subsequently target the protein to different regions of the mitochondria, such as the mitochondrial matrix. Like signal peptides, mitochondrial targeting signals are cleaved once targeting is complete. Mitochondrial Transit peptides are e.g. described in Shewry and Gutteridge (1992, Plant Protein Engineering, 143-146, and references therein), Sjoling and Glaser (Trends Plant Sci Volume 3, Issue 4, 1 Apr. 1998, Pages 136-140), Pfanner (2000, Current Biol, Volume 10, Issue 11), Huang et al (2009, Plant Phys 150(3): 1272-1285), Chen et al. (1996, PNAS, Vol. 93, pp. 11763-11768), Fuji et al. (Plant J 2016). In one example, such a sequence can be aa 1-50 of SEQ ID NO. 20).

In a further embodiment, said functional restorer gene allele is a functional allele of a PPR gene encoded by SEQ ID NO. 16, SEQ ID NO 18, SEQ ID NO. 19, SEQ ID NO 21, or a PPR gene encoding the polypeptide of SEQ ID NO. 17 or SEQ ID NO. 20. For example, said functional restorer gene allele can comprise or encode a sequence that is substantially identical to SEQ ID NO. 16, SEQ ID NO 17, SEQ ID NO 18, SEQ ID NO. 19, SEQ ID NO. 20, SEQ ID NO 21 as defined herein, such as at least 85%, 85.5%, 86%, 87%, 88%, 89%, 90%, 91%, 92%, 93%, 94%, 95%, 96%, 97%, 98%, 99% or 99.5% identical to SEQ ID NO. 16, SEQ ID NO 17, SEQ ID NO 18, SEQ ID NO. 19, SEQ ID NO 20, SEQ ID NO. 21.

In an even further embodiment, said functional restorer gene allele comprises the nucleotide sequence of SEQ ID NO.16, SEQ ID NO 18, SEQ ID NO. 19, SEQ ID NO 21 or encodes the polypeptide of SEQ ID NO. 17 or SEQ ID NO.20.

In a further embodiment, said functional restorer gene allele encoded by said (isolated) nucleic acid molecule is obtainable from USDA accession number PI 583676.

Also provided is a(n) (isolated) polypeptide encoded by the nucleic acid molecule as described above (said polypeptide encoding a functional restorer protein for wheat G-type cytoplasmic male sterility).

The functional restorer gene allele may also be cloned and a chimeric gene may be made, e.g. by operably linking a plant expressible promoter to the functional restorer gene allele and optionally a 3' end region involved in transcription termination and polyadenylation functional in plants. Such a chimeric gene may be introduced into a plant cell, and the plant cell may be regenerated into a whole plant to produce a transgenic plant. In one aspect the transgenic plant is a cereal plant, such as a wheat plant, according to any method well known in the art.

Thus, in a particular embodiment a chimeric gene is provided comprising a(n) (isolated) nucleic acid molecule encoding the functional restorer gene allele as described above, operably linked to a heterologous plant-expressible promoter and optionally a 3' termination and polyadenylation region.

The use of such a (isolated or extracted) nucleic acid molecule and/or of such a chimeric gene and/or of such a chromosome fragment for generating plant cells and plants comprising a functional restorer gene allele is encompassed herein. In one aspect it may be used to generate transgenic cereal (e.g. wheat) cells, plants and plant parts or seeds comprising the functional restorer gene allele and the plant having the capacity to restore fertility against wheat G-type cytoplasmic male sterility as described above.

A host or host cell, such as a (cereal_plant cell or (cereal) plant or seed thereof, such as a wheat plant cell or plant or seed thereof, comprising the (isolated) nucleic acid molecule, (isolated) polypeptide, or the chimeric gene as described above is provided, wherein preferably said polypeptide, said nucleic acid, or said chimeric gene in each case is heterologous with respect to said plant cell or plant or seed. The host cell can e.g also be a bacterium, such as *E. coli* or *Agrobacterium* (*tumefaciens*).

Thus, also provided is a method for producing a cereal plant cell or plant or seed thereof, such as a wheat plant cell or plant or seed thereof, comprising a functional restorer gene for wheat G-type cytoplasmic male sterility, or for increasing restoration capacity for wheat G-type cytoplasmic male sterility ("CMS") in a cereal plant, such as a wheat plant, comprising the steps of providing said plant cell or plant with the (recombinant) chromosome fragment or the (isolated) nucleic acid molecule or the chimeric gene as described herein wherein said providing comprises transformation, crossing, backcrossing, genome editing or mutagenesis. Restoration capacity, as used herein, means the capacity of a plant to restore fertility in the progeny of a cross with a G-type cytoplasmic male sterility ("CMS") line. Preferably, said plant expresses or has increased expression of the polypeptide according to the invention. Preferably, said (increase in) expression is at least during (the early phases of) pollen development and meiosis, such as in anther or, more specifically, tapetum, or developing microspores (where said plant did not express or to a lesser extent expressed the polypeptide prior to the providing step).

Thus, also provided is a method for producing a cereal plant cell or plant or seed thereof, such as a wheat plant cell or plant or seed thereof, comprising a functional restorer gene for wheat G-type cytoplasmic male sterility, or for increasing restoration capacity for wheat G-type cytoplasmic male sterility ("CMS") in a cereal plant, such as a wheat plant, comprising the steps of increasing the expression of the (isolated) polypeptide as described herein in said plant cell or plant or seed. Preferably, said (increase in) expression is at least during (the early phases of) pollen development and meiosis, such as in anther or, more specifically, tapetum, or developing microspores. Prior to the providing step said plant did not express or to a lesser extent expressed the polypeptide and/or did not have or to a lesser extent had restoration capacity for wheat G-type cytoplasmic male sterility ("CMS")).

Increasing the expression can be done by providing the plant with the (recombinant) chromosome fragment or the (isolated) nucleic acid molecule or the chimeric gene as described herein, whereby the nucleic acid encoding the functional restorer gene allele is under the control of appropriate regulatory elements such as a promoter driving expression in the desired tissues/cells, but also by providing the plant with transcription factors that e.g. (specifically) recognise the promoter region and promote transcription, such as TALeffectors, dCas, dCpf1 etc coupled to transcriptional enhancers.

Further described is a method for converting a cereal plant, such as a wheat plant, not having the capacity to restore fertility in the progeny of a cross with a G-type cytoplasmic male sterility ("CMS") line (a non-restorer plant) into a plant having the capacity to restore fertility in the progeny of a cross with a G-type cytoplasmic male sterility ("CMS") line (a restorer plant), comprising the steps of modifying the genome of said plant to comprise the (isolated) nucleic acid molecule or the chimeric gene encoding a functional restorer gene allele for wheat G-type cytoplasmic male sterility as described herein wherein said modifying comprises transformation, crossing, backcrossing, genome editing or mutagenesis. Preferably, said plant expresses the polypeptide according to the invention, particularly at least during (the early phases of) pollen development and meiosis, such as in anther or, more specifically, tapetum, or developing microspores. Prior to said modification said plant did not express or to a lesser extent expressed the polypeptide and/or did not have or to a lesser extent had restoration capacity for wheat G-type cytoplasmic male sterility ("CMS")).

Thus, also provided is a method for converting a non-restoring cereal plant, such as a wheat plant, into a restoring plant for wheat G-type cytoplasmic male sterility ("CMS"), or for increasing restoration capacity for wheat G-type cytoplasmic male sterility ("CMS") in a cereal plant, such as a wheat plant, comprising the steps of modifying the genome of said plant to increase the expression of a polypeptide according to the invention in said plant. Preferably, said (increase in) expression is at least during (the early phases of) pollen development and meiosis such as in anther or, more specifically, tapetum, or developing microspores. Prior to said modification said plant did not express or to a lesser extent expressed the polypeptide and/or did not have or to a lesser extent had restoration capacity for wheat G-type cytoplasmic male sterility ("CMS")).

Modifying the genome to increase expression of the polypeptide can for example be done by modifying the native promoter to include regulatory elements that increase transcription, such as certain enhancer element, but also by inactivating or removing certain negative regulatory elements, such as repressor elements or target sites for miRNAs or lncRNAs. The Rf3 5/upstream region including the promoter is included in SEQ ID NO 21, e.g. as represented by nt 7907-11981 or fragments thereof.

Also described is a plant cell or plant, preferably a cereal plant cell or cereal plant or seed thereof, such as a wheat plant cell or plant or seed thereof, produced according to any of the above methods, preferably wherein said plant has an increased restoration capacity for wheat G-type cytoplasmic male sterility ("CMS") compared to said plant prior to the providing step or the modification step. Use of such a plant obtained according to the above methods to restore fertility in the progeny of a cross with a G-type cytoplasmic male sterility ("CMS") plant or to produce hybrid plants or hybrid seed is also described. Such a plant cell, plant or seed can be a hybrid plant cell, plant or seed.

Genome editing, as used herein, refers to the targeted modification of genomic DNA using sequence-specific enzymes (such as endonuclease, nickases, base conversion enzymes) and/or donor nucleic acids (e.g. dsDNA, oligo's) to introduce desired changes in the DNA. Sequence-specific nucleases that can be programmed to recognize specific DNA sequences include meganucleases (MGNs), zinc-finger nucleases (ZFNs), TAL-effector nucleases (TALENs) and RNA-guided or DNA-guided nucleases such as Cas9, Cpf1, CasX, CasY, C2c1, C2c3, certain argonout systems (see e.g. Osakabe and Osakabe, Plant Cell Physiol. 2015 March; 56(3):389-400; Ma et al., Mol Plant. 2016 Jul. 6; 9(7):961-74; Bortesie et al., Plant Biotech J, 2016, 14; Murovec et al., Plant Biotechnol J. 2017 Apr. 1; Nakade et al., Bioengineered 8-3, 2017; Burstein et al., Nature 542, 37-241; Komor et al., Nature 533, 420-424, 2016; all incorporated herein by reference). Donor nucleic acids can be used as a template for repair of the DNA break induced by a sequence specific nuclease, but can also be used as such for gene targeting (without DNA break induction) to introduce a desired change into the genomic DNA.

Accordingly, using these technologies, plants lacking a functional restorer gene for wheat G-type cytoplasmic male sterility (non-restoring plants) can be converted to restoring plants by making the desired changes to existing PPR genes or alternatively to introduce one or more complete sequences encoding functional PPR Rf proteins, e.g. as described herein, at a specific genomic location.

Mutagenesis as used herein, refers to e.g. EMS mutagenesis or radiation induced mutagenesis and the like.

Thus, transgenic cereal cells, e.g. transgenic wheat cells, comprising in their genome a recombinant chromosome fragment as described or an (isolated) nucleic acid molecule as described or a chimeric gene as described comprising a functional restorer gene allele as described are also an embodiment of the invention. In one aspect the DNA molecule comprising Rf allele is stably integrated into the cereal (e.g. wheat) genome.

Thus, cereal plants, plant parts, plant cells, or seeds thereof, especially wheat, comprising a chromosome fragment or a nucleic acid molecule according to the invention or a polypeptide according to the invention or a chimeric gene according to the invention encoding a functional restorer gene according to the invention, are provided, said plant having the capacity to restore fertility against wheat G-type cytoplasmic male sterility are provided herein. In one embodiment, the chromosome fragment, nucleic acid molecule, polypeptide or chimeric gene is heterologous to the plant, such as transgenic cereal plants or transgenic wheat plants. This also includes plant cells or cell cultures comprising such a chromosome fragment or nucleic acid molecule, polypeptide or chimeric gene, independent whether introduced by transgenic methods or by breeding methods. The cells are e.g. in vitro and are regenerable into plants comprising the chromosome fragment or chimeric gene of the invention. Said plants, plant parts, plant cells and seeds may also be hybrid plants, plant parts, plant cells or seeds.

Such plants may also be used as male parent plant in a method for producing F1 hybrid seeds or F1 hybrid plants, as described above.

A plant-expressible promoter as used herein can be any promoter that drives sufficient expression at least during (early) pollen development and meiosis, such as in anther or, more specifically, tapetum, or developing microspores. This can for example be a constitutive promoter, an inducible promoter, but also a pollen-, anther- or, more specifically tapetum- or microspore-specific/preferential promoter.

A constitutive promoter is a promoter capable of directing high levels of expression in most cell types (in a spatio-temporal independent manner). Examples of plant expressible constitutive promoters include promoters of bacterial origin, such as the octopine synthase (OCS) and nopaline synthase (NOS) promoters from *Agrobacterium*, but also promoters of viral origin, such as that of the cauliflower mosaic virus (CaMV) 35S transcript (Hapster et al., 1988, Mol. Gen. Genet. 212: 182-190) or 19S RNAs genes (Odell et al., 1985, Nature. 6; 313(6005):810-2; U.S. Pat. No. 5,352,605; WO 84/02913; Benfey et al., 1989, EMBO J. 8:2195-2202), the enhanced 2×35S promoter (Kay at al., 1987, Science 236:1299-1302; Datla et al. (1993), Plant Sci 94:139-149) promoters of the cassava vein mosaic virus (CsVMV; WO 97/48819, U.S. Pat. No. 7,053,205), 2×CsVMV (WO2004/053135) the circovirus (AU 689 311) promoter, the sugarcane bacilliform badnavirus (ScBV) promoter (Samac et al., 2004, Transgenic Res. 13(4):349-61), the figwort mosaic virus (FMV) promoter (Sanger et al., 1990, Plant Mol Biol. 14(3):433-43), the subterranean clover virus promoter No 4 or No 7 (WO 96/06932) and the enhanced 35S promoter as described in U.S. Pat. Nos. 5,164,316, 5,196,525, 5,322,938, 5,359,142 and 5,424,200.

Among the promoters of plant origin, mention will be made of the promoters of the plant ribulose-biscarboxylase/oxygenase (Rubisco) small subunit promoter (U.S. Pat. No. 4,962,028; WO99/25842) from *Zea mays* and sunflower, the promoter of the *Arabidopsis thaliana* histone H4 gene (Chabouté et al., 1987), the ubiquitin promoters (Holtorf et al., 1995, Plant Mol. Biol. 29:637-649, U.S. Pat. No. 5,510,474) of Maize, Rice and sugarcane, the Rice actin 1 promoter (Act-1, U.S. Pat. No. 5,641,876), the histone promoters as described in EP 0 507 698 A1, the Maize alcohol dehydrogenase 1 promoter (Adh-1) (from world wide web at patentlens.net/daisy/promoters/242.html)). Also the small subunit promoter from *Chrysanthemum* may be used if that use is combined with the use of the respective terminator (Outchkourov et al., Planta, 216: 1003-1012, 2003).

Pollen/microspore-active promoters include e.g. a maize pollen specific promoter (see, e.g., Guerrero (1990) Mol. Gen. Genet. 224:161 168), PTA29, PTA26 and PTAI 3 (e.g., see U.S. Pat. No. 5,792,929) and as described in e.g. Baerson et al. (1994 Plant Mol. Biol. 26: 1947-1959), the NMT19 microspore-specific promoter as e.g. described in WO97/30166. Further anther/pollen-specific or anther/pollen-active promoters are described in e.g. Khurana et al., 2012 (Critical Reviews in Plant Sciences, 31: 359-390), WO2005100575, WO 2008037436. Other suitable promoters are e.g the barley vrn1 promoter, such as described in Alonso-Peral et al. (2001, PLoS One. 2011; 6 (12):e29456).

It will be clear that the herein identified nucleic acids and polypeptides encoding functional restorer genes can be used to identify further functional restorer genes for wheat G-type cytoplasmic male sterility. Thus, the invention also provides the use of the (isolated) nucleic acids or polypeptides as disclosed herein, such as SEQ ID NO. 16 or 17, to identify one or more further functional restorer genes for wheat G-type cytoplasmic male sterility.

Further, homologous or substantially identical functional restorer genes can be identified using methods known in the art. Homologous nucleotide sequence may be identified and isolated by hybridization under stringent or high stringent conditions using as probes a nucleic acid comprising e.g. the nucleotide sequence of SEQ ID NO: 16 or part thereof, as described above. Other sequences encoding functional restorer genes may also be obtained by DNA amplification using oligonucleotides specific for genes encoding functional restorer genes as primers, such as but not limited to oligonucleotides comprising or consisting of about 20 to about 50 consecutive nucleotides from SEQ ID NO: 16 or its complement. Homologous or substantially identical functional restorer genes can be identified in silico using Basic Local Alignment Search Tool (BLAST) homology search with the nucleotide or amino acid sequences as provided herein.

Functionality of restorer genes or alleles thereof, such as identified as above, can be validated for example by providing, e.g. by transformation or crossing, such a restorer gene under control of a plant-expressible promoter in a cereal (wheat) plant that does not have the capacity to restore fertility of offspring of a G-type cytoplasmic male sterile wheat plant, crossing the thus generated cereal plant with a G-type cytoplasmic male sterile wheat plant and evaluating seed set in the progeny. Alternatively, a restorer line can be transformed with an RNAi construct or gene-edited with e.g. CRISPR-Cas technology or any other sequence specific nuclease so to generate a loss of function that renders the plant non-restoring. Similarly, other means for mutating the restorer gene (e.g. EMS, g-radiation) can be used to evaluate the effect of a loss of function mutation on restoring ability.

In any of the herein described embodiments and aspects the plant may comprise or may be selected to comprise or may be provided with a further functional restorer gene for wheat G-type cytoplasmic male sterility (located on or obtainable from the same or another chromosome), such as Rf1 (1A), Rf2 (7D), Rf4 (6B), Rf5 (6D), Rf6 (5D), Rf7 (7B), Rf8, 6AS or 6BS (Tahir & Tsunewaki, 1969; Yen et al., 1969; Bahl & Maan, 1973; Du et al., 1991; Sihna et al., 2013; Ma et al., 1991; Zhou et al., 2005).

Any of the herein described methods, markers and marker alleles, nucleic acids, polypeptides, chimeric genes, plants etc may also be used to restore fertility against S$^v$-type cytoplasm, as e.g. described in Ahmed et al 2001 (supra).

As used herein a "chimeric gene" refers to a nucleic acid construct which is not normally found in a plant species. A chimeric nucleic acid construct can be DNA or RNA. "Chimeric DNA construct" and "chimeric gene" are used interchangeably to denote a gene in which the promoter or one or more other regulatory regions, such as the a transcription termination and polyadenylation region of the gene are not associated in nature with part or all of the transcribed DNA region, or a gene which is present in a locus in the plant genome in which it does not occur naturally or present in a plant in which it does not naturally occur. In other words, the gene and the operably-linked regulatory region or the gene and the genomic locus or the gene and the plant are heterologous with respect to each other, i.e. they do not naturally occur together.

A first nucleotide sequence is "operably linked" with a second nucleic acid sequence when the first nucleic acid sequence is in a functional relationship with the second nucleic acid sequence. For example, a promoter is operably linked to a coding sequence if the promoter affects the transcription or expression of the coding sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

"Backcrossing" refers to a breeding method by which a (single) trait, such as fertility restoration (Rf), can be transferred from one genetic background (a "donor") into another genetic background (also referred to as "recurrent parent"), e.g. a plant not comprising such an Rf gene or locus. An offspring of a cross (e.g. an F1 plant obtained by crossing an Rf containing with an Rf lacking plant; or an F2 plant or F3 plant, etc., obtained from selfing the F1) is "backcrossed" to the parent. After repeated backcrossing (BC1, BC2, etc.) and optionally selfings (BC1S1, BC2S1, etc.), the trait of the one genetic background is incorporated into the other genetic background.

"Marker assisted selection" or "MAS" is a process of using the presence of molecular markers, which are genetically linked to a particular locus or to a particular chromosome region (e.g. introgression fragment), to select plants for the presence of the specific locus or region (introgression fragment). For example, a molecular marker genetically and physically linked to an Rf locus, can be used to detect and/or select plants comprising the Rf locus. The closer the genetic linkage of the molecular marker to the locus, the less likely it is that the marker is dissociated from the locus through meiotic recombination.

"LOD-score" (logarithm (base 10) of odds) refers to a statistical test often used for linkage analysis in animal and plant populations. The LOD score compares the likelihood of obtaining the test data if the two loci (molecular markers loci and/or a phenotypic trait locus) are indeed linked, to the likelihood of observing the same data purely by chance. Positive LOD scores favor the presence of linkage and a LOD score greater than 3.0 is considered evidence for linkage. A LOD score of +3 indicates 1000 to 1 odds that the linkage being observed did not occur by chance.

A "biological sample" can be a plant or part of a plant such as a plant tissue or a plant cell.

"Providing genomic DNA" as used herein refers to providing a sample comprising genomic DNA from the plant. The sample can refer to a tissue sample which has been obtained from said plant, such as, for example, a leaf sample, comprising genomic DNA from said plant. The sample can further refer to genomic DNA which is obtained from a tissue sample, such as genomic DNA which has been obtained from a tissue, such as a leaf sample. Providing genomic DNA can include, but does not need to include, purification of genomic DNA from the tissue sample. Providing genomic DNA thus also includes obtaining tissue material from a plant or larger piece of tissue and preparing a crude extract or lysate therefrom.

"Isolated DNA" as used herein refers to DNA not occurring in its natural genomic context, irrespective of its length and sequence. Isolated DNA can, for example, refer to DNA which is physically separated from the genomic context, such as a fragment of genomic DNA. Isolated DNA can also be an artificially produced DNA, such as a chemically synthesized DNA, or such as DNA produced via amplification reactions, such as polymerase chain reaction (PCR) well-known in the art. Isolated DNA can further refer to DNA present in a context of DNA in which it does not occur naturally. For example, isolated DNA can refer to a piece of DNA present in a plasmid. Further, the isolated DNA can refer to a piece of DNA present in another chromosomal context than the context in which it occurs naturally, such as for example at another position in the genome than the natural position, in the genome of another species than the species in which it occurs naturally, or in an artificial chromosome.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the restoring capacity), such as seed obtained by selfing or crossing, e.g. hybrid seed (obtained by crossing two inbred parental lines), hybrid plants and plant parts derived there from are encompassed herein, unless otherwise indicated.

In some embodiments, the plant cells of the invention may be non-propagating cells.

The obtained plants according to the invention can be used in a conventional breeding scheme to produce more plants with the same characteristics or to introduce the characteristic of the presence of the restorer gene according to the invention in other varieties of the same or related plant species, or in hybrid plants. The obtained plants can further be used for creating propagating material. Plants according to the invention can further be used to produce gametes, seeds, flour, embryos, either zygotic or somatic, progeny or hybrids of plants obtained by methods of the invention. Seeds obtained from the plants according to the invention are also encompassed by the invention.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

Transformation, as used herein, means introducing a nucleotide sequence into a plant in a manner to cause stable or transient expression of the sequence. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

As used herein, the term "homologous" or "substantially identical" may refer to nucleotide sequences that are more than 85% identical. For example, a substantially identical nucleotide sequence may be 85.5%; 86%; 87%; 88%; 89%; 90%; 91%; 92%; 93%; 94%; 95%; 96%; 97%; 98%; 99% or 99.5% identical to the reference sequence. A probe may also be a nucleic acid molecule that is "specifically hybridizable" or "specifically complementary" to an exact copy of the marker to be detected ("DNA target"). "Specifically hybridizable" or "specifically complementary" are terms that indicate a sufficient degree of complementarity such that stable and specific binding occurs between the nucleic acid molecule and the DNA target. A nucleic acid molecule need not be 100% complementary to its target sequence to be specifically hybridizable. A nucleic acid molecule is specifically hybridizable when there is a sufficient degree of complementarity to avoid non-specific binding of the nucleic acid to non-target sequences under conditions where specific binding is desired, for example, under stringent hybridization conditions, preferably highly stringent conditions.

"Stringent hybridization conditions" can be used to identify nucleotide sequences, which are homologous or substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100nt) are for example those which include at least one wash in 0.2× SSC at 63° C. for 20 min, or equivalent conditions.

"High stringency conditions" can be provided, for example, by hybridization at 65° C. in an aqueous solution containing 6× SSC (20× SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denatured carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1× SSC, 0.1% SDS.

"Moderate stringency conditions" refers to conditions equivalent to hybridization in the above described solution but at about 60-62° C. Moderate stringency washing may be done at the hybridization temperature in 1× SSC, 0.1% SDS.

"Low stringency" refers to conditions equivalent to hybridization in the above described solution at about 50-52° C. Low stringency washing may be done at the hybridization temperature in 2× SSC, 0.1% SDS. See also Sambrook et al. (1989) and Sambrook and Russell (2001).

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. world wide web at ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62. It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a nucleic acid which is functionally or structurally defined, may comprise additional DNA regions etc.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

The sequence listing contained in the file named "BCS16-2008-WO1_ST25, which is 83 kilobytes (size as measured in Microsoft Windows®), contains 26 sequences SEQ ID NO: 1 through SEQ ID NO: 26, is filed herewith by electronic submission and is incorporated by reference herein.

The invention will be further described with reference to the examples described herein; however, it is to be understood that the invention is not limited to such examples.

Sequences

SEQ ID NO. 1—SEQ ID NO. 14: marker sequences (see table 1 and 2)
SEQ ID NO. 15: Contig containing Rf3-PPR
SEQ ID NO. 16: Coding sequence Rf3-PPR
SEQ ID NO. 17 Amino acid sequence Rf3-PPR
SEQ ID NO. 18: manually annotated mRNA Rf-PPR3
  Nt 1-64: 5' UTR
  Nt 65-2437: CDS
  Nt 2438-3438: 3' UTR
SEQ ID NO. 19: manually annotated coding sequence Rf3-PPR
SEQ ID NO. 20: manually annotated amino acid sequence Rf3-PPR
SEQ ID NO. 21: Genome sequence Rf3-PPR
  Nt 4468-5470:3'UTR (complement)
  Nt 5471-7843: CDS (complement)
  Nt 7844-7907: 5'UTR (complement)
SEQ ID NO. 22: predicted RNA target
SEQ ID NO. 23: ORF256
  Nt 84-857: CDS
SEQ ID NO. 24 Fw primer
SEQ ID NO. 25: Rev primer
SEQ ID NO. 26: Probe

EXAMPLES

Example 1: Plant Materials and Genetic Mapping

A male sterile line carrying *Triticum timopheevii* CMS, CMS005, and a male sterile restorer line responding to *Triticum timopheevii* CMS (*T. timopheevii*/2* lowin//2* Quivira, Accession number PI 583676, USDA National Small Grains Collection;, also known as Dekalb 582M and registered as US PVP 7400045, available via the National Plant Germplasm System https://npgsweb.ars-grin.gov/gringlobal/accessiondetail.aspx?id=1478647), were used as parents to generate F1 progeny. The F1 progeny was selfed to generate an F2 population. The F2 population, consisting of 281 individuals, was used for identification of the markers linked to the restorer locus. A genetic map with total of 2080 SNP markers was established and covered all chromosomes of the wheat genome. The chromosome 1B is described by 150 SNP markers.

Example 2: Fertility Classification and Coarse Mapping

The 276 plants in this F2 population were phenotypically classified according to seed set on the main, bagged head. Plants without seeds under the bag were classified as sterile. Plants with seed set were classified as fertile. FIG. 1 details the number of F2s per amount of seeds set on a single head for 2 different locations. 41 and 45 F2 plants in the 2 locations, were classified as sterile. Fully sterile F2 plants were noticed in the 2 locations.

Using a genetic map of 2080 SNP, QTL analysis was carried out using Haley-Knott regression to test the effect of variation in seed set across all markers. Significant marker-trait associations are distinguished by −log-transformed p-values higher than 3. Such, an interval of significantly associated markers was delineated, including left and right flanking markers (SEQ ID NO. 2 and SEQ ID NO. 8). The marker with the highest significance and biggest effect on restoration is the peak marker of SEQ ID NO. 6 (as indicated by X in Table 1 below). An interval of significantly associated markers was delineated using the following criteria: significance threshold at 2.5, significance drop at 1.5 and significance drop between peaks at 2. This delimited the interval to 15.8 cM for 1B by the left and right flanking markers (FIG. 2).

TABLE 1

Markers in the interval with significance of marker-trait association and effect size on restoration (in number of seeds above average seed set in the entire population) on 1B.

| SEQ ID NO | Rf donor allele | SNP position in SEQ ID NO | Chromo- some Position (cM) | Signifi- cance (−log10(p)) | Signifi- cance interval | mean seed set | additive effect on seed set | domi- nance effect on seed set | pheno- typic variance explained |
|---|---|---|---|---|---|---|---|---|---|
| 1 | A | 51 | 35.206 | 7.51 |   | 31.68 | 10.05 | 1.02 | 0.13 |
| 2 | T | 51 | 35.753 | 8.2 | x | 31.4 | 10.51 | 1.32 | 0.14 |
| 3 | C | 51 | 38.165 | 10.49 | x | 31.26 | 11.8 | 1.85 | 0.18 |
| 4 | T | 51 | 38.37 | 10.51 | x | 31.26 | 11.8 | 1.83 | 0.18 |
| 5 | T | 51 | 42.221 | 10.41 | x | 30.65 | 11.78 | 2.56 | 0.18 |
| 6 | A | 32 | 46.302 | 10.67 | x | 31.51 | 12.06 | 1.53 | 0.18 |
| 7 | A | 51 | 46.911 | 10.5 | X | 31.52 | 11.97 | 1.51 | 0.18 |
| 8 | G | 51 | 51.588 | 9.05 | x | 30.85 | 10.85 | 2.44 | 0.15 |
| 9 | T | 51 | 51.772 | 9.05 |   | 30.85 | 10.85 | 2.44 | 0.15 |

The mapping positions were confirmed when using seed set on a secondary head in both locations and when using phenotypic data of F3 progeny of this populations the next year in two locations.

Example 3: Fine-Mapping of Rf Region in 1B

For further fine-mapping, 40 F2 individuals that were heterozygous in the QTL region were selected based on phenotype and genotype. A total of 2560 individual F3 plants were grown in the field at 2 locations. For each plant, seed set on the main head under a bag was measured. Additional SNP assays were developed to increase the marker density in the QTL interval. A total of 374 additional SNP markers were using in mapping the 1B region. Table 2 provides exemplary SNP markers that were mapped in the region.

Marker-trait association using genetic maps of the chromosome 1B, established on F2 and F3 genotyping data, were determined using R-QTL. A total of 1094 individuals with genotype and phenotype data were processed per location. The Rf locus could be further delimited to a region of about 1.25 cM 1B (from 6.8 to 8.05 cM along chromosome 1B).

TABLE 2

Exemplary markers in the fine-mapped region on 1B.

| SEQ ID NO | Rf donor allele | SNP position | finemap map position (cM) | significant marker interval I | peak marker |
|---|---|---|---|---|---|
| 10 | T | 51 | 6.1 | | |
| 11 | C | 51 | 7.1 | x | |
| 12 | A | 51 | 7.3 | x | |
| 13 | T | 51 | 7.35 | x | v |
| 14 | T | 108 | 8.05 | x | |
| 5 | T | 51 | 8.1 | | |

Significant markers (highlighted with x) are examples of markers that are in the QTL support interval (LOD threshold >3; drop of 2 LODs from highest marker). The marker closest to the peak is marked with (v). Other markers residing outside the significant interval are indicated by 'left flanking region' (above) and 'right flanking region (below).

Example 4: Integration of the Fine Map with Partial Genome Sequence and Candidate Gene Identification Sequence of fine-mapped markers was used for Blasts to contigs and scaffolds of genome sequence of Chinese Spring. Stringent BLAST and parsing criteria were applied to position the SNPs in the partial genome sequence, such as >98% sequence identity, alignment length of >158 bp, hit in 1B sequence, and additional criteria for non-aligning overhang. Scaffolds were ordered to the fine map (and additional genetic maps). Next, the Rf clade of pentatricopeptide repeat protein sequences from maize, Sorghum, rice and Brachypodium were collected, using a gene family analysis of Fujii et al. (PNAS, 2011, supra, see Table S1). A total of 43 protein sequences were used for BLASTs and identified one locus in the fine-mapped interval.

The scaffold containing the PPR gene is given as SEQ ID NO. 15.

The thus identified PPR gene is represented by SEQ ID NO. 16 (nt-coding sequence) and 17 (aa).

Manual annotation resulted in the mRNA sequence of SEQ ID NO. 18, with the coding sequence of SEQ ID NO. 19 encoding the amino acid sequence of SEQ ID NO. 20.

Example 5—Further Fine-Mapping of Rf Region in 1B (F4) and in Silico Analysis A set of SNP markers that were used for fine-mapping of the Rf3 locus were aligned to appropriate reference genome(s) to define a physical region representing the Rf3 QTL region on the reference genome. This QTL region was used to identify potential candidate genes and to develop additional markers for BAC-library screening (see below). Structural annotation of the Rf3 QTL region using ab initio gene annotation programs an in-house annotation pipeline, as well as by alignment of wheat EST sequences, wheat FL-cDNA sequences, wheat gene models and known restorer genes from orthologous species available from public databases. Functional annotation of genes in the QTL region was carried out using Blast2GO and PLAZA software programs as well as consultation of published literature. These candidate genes were then prioritized on the basis of their predicted functionality and their homology to known Rf genes (Chen and Liu, 2014; Dahan and Mireau, 2013).

Mapping fine-mapping genetic markers to the 'Chinese Spring' reference genome defined a region of ~1.3 Mb on chromosome 1B that represented the Rf3 QTL region. In the 'Chinese Spring' reference, this region contained the identified pentacotripeptide (PPR) gene. PPR proteins are a large family of proteins that are characterized by possession of the canonical, degenerate 35-amino acid repeat motifs and that have been identified in other crops as being involved in restoration of fertility. This is mainly through mechanisms involving modification of the processing and/or transcription of cytotoxic mitochondrial transcripts (Dahan and Mireau, 2013; Gaborieau et al., 2016) (Chen and Liu, 2014; Schmitzlinneweber and Small, 2008). Restoration of fertility-type PPRs (Rf-PPRs) are members of the P-class of PPR proteins that typically bind single-stranded RNA in a sequence-specific fashion (Barkan et al., 2012; Binder et al., 2013; Chen and Liu, 2014; Gaborieau et al., 2016; Schmitzlinneweber and Small, 2008). Comparison of the sequences of the PPR gene sequences present in the Rf3 QTL region showed that they clustered with known P-class Rf-PPR orthologues from other crop species (data not shown).

Example 6—BAC Libraries of Restorer Line

In parallel with the in silico analysis (see above), a BAC library was constructed for the above described wheat restorer line (hereafter referred to as 'Resource-5'), by digesting high-molecular weight 'Resource-5' gDNA with a restriction enzyme, and transforming the resultant fragments (mean insert size ~80-130 Kb), into *E. coli*. The fine-mapping SNP marker sequences, or markers developed from the Rf3 QTL region on the reference genome, were then used to design PCR primers to screen the pooled BAC clones. Once PCR-positive BAC pools had been identified, BACs from the pool were individualized and screened again with the same marker. Individual, PCR-positive BACs were then subjected to BAC-end sequencing to confirm integrity and the presence of the screening marker sequences. Finally verified positive BACs were deep sequenced using PacBio technology and reads assembled to generate a consensus sequence for the BAC insert. Sequenced, positive BACs were then aligned either by de novo assembly, or by assembly to the reference genome or tiled using the screening markers to generate a new 'Resource-5' reference sequence for the Rf3 QTL region. The 'Resource-5' Rf3 QTL reference sequence was then structurally and functionally annotated to identify any structural changes and/or differences in gene content and/or polymorphisms in the candidate gene captured within the region relative to the (non-restorer) reference genome.

The 'Resource-5' BAC library was screened multiple times using PCR markers developed from fine-mapping markers, reference genomes or isolated BAC sequences. Fourteen individualized and sequenced BACs were then tiled to create a contiguous sequence of ~650 Kb and one additional sequence of 121 Kb separated by a gap of ~75 Kb relative to the 'Chinese Spring' reference genome. These contigs represent the unique 'Resource-5' genome sequence for the Rf3 QTL region and were found to capture the Rf-PPR candidate gene initially identified.

As shown in FIG. 3A, the gene structure for Rf3-PPR is relatively simple consisting of a single exon and with no introns. This relatively simple gene structure appears to be typical for Rf-PPRs.

Comparison of one of the 'Resource-5' Rf3-PPR candidate gene to the 'Chinese Spring' orthologue indicated that the sequence is highly conserved and that there are no SNPs present either in the CDS or +/−3 Kb up and downstream of the CDS. This suggests that the restorer phenotype is not linked to structural differences in the Rf-PPR protein.

SEQ ID NO. 21 represents the genomic DNA sequence of the Rf3-PPR gene

Example 7—Annotation of the PPR Amino Acid Sequence

Known Rf-PPRs are members of the P-class of PPR proteins, and contain up to ~30 PPR motifs per protein, with each motif comprising 35 amino acids (Gaborieau et al., 2016). Structurally PPR proteins consist of 2 α-helices that form a hairpin and a super-groove, and it is this super groove that interacts with an RNA molecule. The amino acid composition of the individual PPR motifs determines RNA which nucleotide is recognized, and the number of PPR motifs determines the length of the RNA sequence on the target transcript. Here the Rf3-PPRcandidate was annotated to identify PPR motifs and other sequence features and the results summarized in FIGS. 3B and C.

Rf3-PPR consists of 790 amino acids and contains 18 consecutive 35 amino-acid PPR motifs, and a predicted transit peptide that targets the protein to the mitochondria (SEQ ID NO. 20). This is very similar to the structure of the Rf-1A gene cloned from rice, which is 791 amino acids long and contains 16 PPR repeats (Akagi et al., 2004; Komori et al., 2004).

Each PPR motif consists of 2 antiparallel helices that form a hairpin structure that interacts with a single stranded RNA molecule. Studies have demonstrated the existence of a recognition code linking the identity of specific amino acids within the repeats and the target RNA sequence of the PPR protein studied (Barkan et al., 2012; Yagi et al., 2013). In particular the identity of the 5th and the 35th amino acids of each motif have been shown to be particularly important and in the context of CMS, specificity is essential to specifically target the CMS-conferring transcript. On the basis of the identity of the amino acids at positions 5 and 35 in the Rf-PPR motif the predicted target transcript sequence for Rf3-PPR can be determined. Following the PPR code (Melonek et al., 2016, supra), the predicted RNA target sequence is thus 5'-ACCUGUNCGUAYNYGCAU-3' (SEQ ID NO. 22, see also Table 3 below).

As shown in FIG. 4, alignment of the predicted target sequence of Rf3-PPR to the chimeric mitochondrial ORF-256 transcript (SEQ ID NO. 23), which has been proposed to be responsible for the CMS phenotype (Hedgcoth et al., 2002) indicates that there is a potential interaction site at positions 129-146 (sequence ACTGCTTTCTATTTGCAC).

The results here indicate that Rf3-PPR potentially binds the chimeric ORF256 transcript responsible for the CMS phenotype rand where it is thought to act by reducing the steady-state level of the deleterious ORF256 either by decreasing the stability of the corresponding RNA or by reducing translation (Binder et al., 2013).

TABLE 3

PPR motifs and base recognition-See also FIG. 3.

| PPR motif | Aa positions (SEQ ID NO. 20) | Position 5 and 35 | Base recognition |
|---|---|---|---|
| 1 | 121-155 | GN | A |
| 2 | 156-191 | NN | C |
| 3 | 192-226 | NN | C |
| 4 | 227-261 | ND | U |
| 5 | 262-296 | SD | G |
| 6 | 297-331 | ND | U |
| 7 | 332-336 | AN | ? |
| 8 | 367-401 | NN | C |
| 9 | 402-436 | SD | G |
| 10 | 437-472 | RD | U |
| 11 | 473-507 | SN | A |
| 12 | 508-542 | NC | C/U |
| 13 | 543-577 | GT | ? |
| 14 | 578-612 | NC | C/U |
| 15 | 613-647 | SD | G |
| 16 | 648-682 | NN | C |
| 17 | 683-717 | TN | A |
| 18 | 718-752 | NE | U |

Example 8—Expression Analysis mRNA

Total RNA was isolated from ~70-100 mgfw tissue using the Sigma Spectrum Plant Total RNA Kit (Sigma-Aldrich), and any gDNA contamination removed using the Qiagen RNase-Fee DNase Set (Cat. No. 79254). DNA concentration and integrity were determined with an Agilent Expert Bio-Analyser. Tissue was sampled at four developmental stages (young leaf, spike 2.5-3.5, spike 3.5-4.5, spike 4.5-5.5 cm and anthers), using individuals from an F4-population of progeny derived from 'Resource-5'. These progeny were genotyped using fine-mapping markers, phenotyped for fertility traits, and classified as either non-restoring (-/-), or heterozygous for Rf3 (Rf3/-). Three individual biological replicates were prepared per tissue type per genotype.

qRT-PCR Analyses mRNA from each of the tissue/Rf3 genotypes was converted into cDNA using the EcoMix dry kit from Clonetech. Gene-specific probes were designed to quantify gene expression levels using the TaqMan assay as summarized in table 4. Probe specificity and efficiency were tested and optimised and expression analyses carried out on cDNA samples generated as above.

TABLE 4

TagMan primer and probe sequences used for gene expression analyses.

| Gene i.d. | Name | Type | Target Region | Sequence 5' --> 3' | SEQ ID NO. |
|---|---|---|---|---|---|
| Rf3-PPR | Fw2 | Primer | 1648..1671 | TGATGGTGTTGGACCTGATAATGT | 24 |
| | Rev2 | Primer | complement(1696..1717) | CCAGTGGCCTGAAGAGGAATAT | 25 |
| | P2 | Probe | 1673..1693 | ACGTATAGTAGCCTCATCCAT | 26 |

Gene expression was examined in individual plants selected from f4 fine-mapping progeny segregating for the Rf3 locus, in four different tissues. Young leaf, developing spike 2.5-3.5 cm, developing spike 3.5-4.5 cm, developing spike 4.5-5.5 cm and anthers. Since it is expected that the cytoplasmic male sterile phenotype is due to the production of non-viable pollen, Rf genes must at least be expressed during the period of pollen development and meiosis. It is also expected that Rf gene expression will be highest in the early stages of pollen development.

As shown in FIG. 5, it is clear that mean expression of the PPR gene, is exclusively associated with the presence of the Rf3 locus, and is also highest at the 3.5-4.5 cm stage of spike development.

The Resource-5 Rf3-PPR candidate does not possess any SNPs or polymorphisms relative to the non-restorer Chinese Spring reference, within a 12 Kb region centered around the CDS. However it is situated at/or near the QTL peak for the restoration phenotype and expression is exactly correlated with the presence of an active Rf3 locus. The Rf3-PPR does however have multiple predicted miRNA binding sites in the region 160-270 bp 5' to the ATG start and is well documented that PPRs in particular are subject to regulation by sRNAs/miRNAs (Xia et al., 2013). E.g. in rice, expression of a lncRNA that produces 21nt sRNA, is required for pollen development under long-day conditions, and a single SNP that alters the secondary lncRNA structure, leads to increased methylation of the promoter region of this lncRNA, reducing transcription and resulting on premature programmed cell death in developing anthers (Ding et al., 2012). Similarly Ding et al demonstrated that a single polymorphism in the rice sRNA osa-smR5864m, is a common cause for pollen sterility in *japonica* and *indica* lines (Ding et al., 2012). Wei et al also identified miRNAs responsible for pollen abortion in Chinese cabbage (Wei et al., 2015) and altered miRNA expression has been associated with male sterility in pumello (Fang et al., 2016) asparagus (Chen et al., 2016) cotton (Wei et al., 2013). Therefore expression could be driven by a trans-acting miRNA/sRNA impacting transcript stability or transcription.

Example 9 Candidate Gene Validation

By Mutagenesis

A mutagenized population of the restore line is constructed. Based on sequencing, mutant plants with an inactivating mutation in the Rf candidate PPR gene are identified. The homozygous mutant plants and their wildtype segregants are screened for fertility restoration capacity. The plants that have a mutated PPR gene no longer has restoring ability, confirming that the identified candidate PPR gene is a functional Rf gene.

By Overexpression

The coding sequence of the candidate PPR-Rf gene is cloned under the control of a constitutive UBIQUITIN promoter (e.g. pUbiZm from maize), or under the control of a constitutive cauliflower mosaic virus promoter (p 35S), or under the control of a vernalisation-related barley promoter (pvrn1) (or under control of its native promoter), in a T-DNA expression vector comprising a selectable marker, such as the bar gene. The resulting vector is transformed into a wheat line having no restoration capacity such as the transformable variety Fielder (or Chinese spring) according to methods well known in the art for wheat transformation (see e.g. Ishida et al Methods Mol Biol. 2015; 1223:189-98). The copy number of the transgene in the transgenic plant is determined by real time PCR on the selectable marker gene. The transformed plants comprising the candidate PPR-Rf gene cassette, preferably in single copy, are transferred to the greenhouse. Expression of the transgene in leaf tissue and in young developing spikes is tested by qRT-PCR. Transgenic TO plants expressing the candidate PPR-Rf gene are crossed as male parents to a G-type cytoplasmic male sterile ("CMS") wheat line. F1 progeny of the crosses contain the G-type cytoplasm and show partial or complete restoration of male fertility due to the presence of the candidate PPR Rf gene.

The level of restoration in F1 progeny is tested using four different assays. In the first assay the mitochondrial ORF256 protein is quantified on Western blot using polyclonal antibodies raised against synthetic ORF256 protein. Expression of a functional candidate PPR Rf gene leads to reduced accumulation of the ORF256 protein. In the second assay pollen accumulation and pollen viability is quantified using the AmphaZ30 device. Expression of a functional candidate PPR Rf gene leads to higher numbers of viable pollen. In the third assay the integrity of anther tissues is inspected microscopically. Expression of a functional candidate PPR-Rf gene leads to better preservation of functional tapetum layer. In the fourth assay seed set per ear from self-pollination is quantified. Expression of a functional candidate PPR-Rf gene leads to higher number of grains per ear. In all tests the F1 progeny from crosses of non-transgenic Fielder plants to the same G-type cytoplasmic male sterile ("CMS") wheat line serves as a control.

By Targeted Knock-Out

Guide RNAs for CRISPR-mediated gene editing targeting the mRNA coding sequence, preferably the protein coding sequence of the candidate PPR Rf gene, or the immediately upstream promoter sequence of the candidate PPR Rf gene are designed by using e.g. the CAS-finder tool. Preferably four unique or near-unique guide RNAs are designed per target gene. The guide RNAs are tested for targeting efficiency by PEG-mediated transient co-delivery of the gRNA expression vector with an expression vector for the respective nuclease, e.g. Cas9 or Cpf1, under control of appropriate promoters, to protoplasts of a wheat restorer line containing the candidate PPR-Rf gene of interest, preferably the line designated as *T. timopheevii*/2* lowin//2* Quivira, USDA Accession number PI 583676. Genomic DNA is extracted from the protoplasts after delivery of the guide RNA and nuclease vectors. After PCR amplification, integrity of the targeted candidate PPR Rf gene sequence is assessed by sequencing.

The one or two most efficient guide RNAs are used for stable gene editing in same wheat restorer line also containing the G-type CMS cytoplasm. For this purpose, the selected guide RNA expression vector, together with a nuclease expression module and a selectable marker gene, are introduced into embryos isolated from the before mentioned wheat restorer line using e.g. particle gun bombardment. Transgenic plants showing resistance to the selection agent are regenerated using methods known to those skilled in the art. Transgenic TO plants containing gene targeting events, preferably small deletions likely resulting in a non-functional target candidate Rf PPR gene are identified by PCR amplification and sequencing.

Transgenic TO plants containing the G-type CMS cytoplasm and likely to contain a functional knock-out of the candidate PPR-Rf gene, preferably in homozygous state, but alternatively in heterozygous state, are crossed as female parents to a spring wheat line with normal cytoplasm and without PPR-Rf genes. The F1 progeny of the crosses contains the G-type "CMS" cytoplasm and 50% (in case of heterozygous TO) or 100% (in case of homozygous TO) of the F1 progeny will lack a functional version of the target Rf PPR gene. The F1 plants lacking a functional target Rf PPR gene are identified using genomic PCR assays. The F1 plants show partial or complete loss of male fertility due to the knock-out of the candidate PPR Rf gene.

The level of male fertility in the F1 progeny lacking a functional version of the candidate Rf PPR gene is tested using four different assays. In the first assay the mitochondrial ORF256 protein is quantified on Western blot using polyclonal antibodies raised against synthetic ORF256 protein. The knock-out of a functional candidate PPR Rf gene leads to increased accumulation of the ORF256 protein. In the second assay pollen accumulation and pollen viability is quantified using the AmphaZ30 device. The knock-out of a functional candidate PPR Rf gene leads to lower numbers of viable pollen. In the third assay the integrity of anther tissues is inspected microscopically. The knock-out of a functional candidate PPR Rf gene leads to early deterioration of the tapetum layer. In the fourth assay seed set per ear from self-pollination is quantified. The knock-out of a functional candidate PPR Rf gene leads to reduced number of grains per ear. In all tests the F1 progeny from crosses of non-edited Rf plants to the same spring wheat line serve as a control.

REFERENCES

Akagi, H., Nakamura, A., Yokozeki-Misono, Y., Inagaki, A., Takahashi, H., Mori, K., and Fujimura, T. (2004). Positional cloning of the rice Rf-1 gene, a restorer of BT-type cytoplasmic male sterility that encodes a mitochondria-targeting PPR protein. Theor. Appl. Genet. 108, 1449-1457.

Barkan, A., Rojas, M., Fujii, S., Yap, A., Chong, Y. S., Bond, C. S., and Small, I. (2012). A Combinatorial Amino Acid Code for RNA Recognition by Pentatricopeptide Repeat Proteins. PLoS Genet. 8, e1002910.

Binder, S., Stoll, K., and Stoll, B. (2013). P-class pentatricopeptide repeat proteins are required for efficient 5' end formation of plant mitochondrial transcripts. RNA Biol. 10, 1511-1519.

Chen, L., and Liu, Y.-G. (2014). Male Sterility and Fertility Restoration in Crops. Annu. Rev. Plant Biol. 65, 579-606.

Chen, J., Zheng, Y., Qin, L., Wang, Y., Chen, L., He, Y., Fei, Z., and Lu, G. (2016). Identification of miRNAs and their targets through high-throughput sequencing and degradome analysis in male and female *Asparagus officinalis*. BMC Plant Biol. 16, 80.

Dahan, J., and Mireau, H. (2013). The Rf and Rf-like PPR in higher plants, a fast-evolving subclass of PPR genes. RNA Biol. 10, 1469-1476.

Ding, J., Lu, Q., Ouyang, Y., Mao, H., Zhang, P., Yao, J., Xu, C., Li, X., Xiao, J., and Zhang, Q. (2012). A long noncoding RNA regulates photoperiod-sensitive male sterility, an essential component of hybrid rice. Proc. Natl. Acad. Sci. 109, 2654-2659.

Fang, Y.-N., Zheng, B.-B., Wang, L., Yang, W., Wu, X.-M., Xu, Q., and Guo, W.-W. (2016). High-throughput sequencing and degradome analysis reveal altered expression of miRNAs and their targets in a male-sterile cybrid pummelo (*Citrus grandis*). BMC Genomics 17, 591.

Gaborieau, L., Brown, G. G., and Mireau, H. (2016). The Propensity of Pentatricopeptide Repeat Genes to Evolve into Restorers of Cytoplasmic Male Sterility. Front. Plant Sci. 7.

Hedgcoth, C., El-Shehawi, A. M., Wei, P., Clarkson, M., and Tamalis, D. (2002). A chimeric open reading frame associated with cytoplasmic male sterility in alloplasmic wheat with *Triticum timopheevi* mitochondria is present in several *Triticum* and *Aegilops* species, barley, and rye. Curr. Genet. 41, 357-366.

Komori, T., Ohta, S., Murai, N., Takakura, Y., Kuraya, Y., Suzuki, S., Hiei, Y., Imaseki, H., and Nitta, N. (2004). Map-based cloning of a fertility restorer gene, Rf-1, in rice (*Oryza sativa* L.). Plant J. 37, 315-325.

Schmitzlinneweber, C., and Small, I. (2008). Pentatricopeptide repeat proteins: a socket set for organelle gene expression. Trends Plant Sci. 13, 663-670.

Wei, M., Wei, H., Wu, M., Song, M., Zhang, J., Yu, J., Fan, S., and Yu, S. (2013). Comparative expression profiling of miRNA during anther development in genetic male sterile and wild type cotton. BMC Plant Biol. 13, 66.

Wei, X., Zhang, X., Yao, Q., Yuan, Y., Li, X., Wei, F., Zhao, Y., Zhang, Q., Wang, Z., Jiang, W., et al. (2015). The miRNAs and their regulatory networks responsible for pollen abortion in Ogura-CMS Chinese cabbage revealed by high-throughput sequencing of miRNAs, degradomes, and transcriptomes. Front. Plant Sci. 6.

Xia, R., Meyers, B. C., Liu, Z., Beers, E. P., Ye, S., and Liu, Z. (2013). MicroRNA Superfamilies Descended from miR390 and Their Roles in Secondary Small Interfering RNA Biogenesis in Eudicots. Plant Cell Online 25, 1555-1572.

Yagi, Y., Hayashi, S., Kobayashi, K., Hirayama, T., and Nakamura, T. (2013). Elucidation of the RNA Recognition Code for Pentatricopeptide Repeat Proteins Involved in Organelle RNA Editing in Plants. PLoS ONE 8, e57286.

The invention claimed is:

1. A nucleic acid molecule of a gene allele comprising a coding sequence operably-linked to a regulatory region wherein said regulatory region does not naturally occur with said coding sequence, or wherein said gene allele has been modified by transformation, genome editing or mutation, or wherein said gene allele has a native promoter that has been modified to include regulatory elements that increase transcription compared to the native gene, or to inactivate or remove negative regulatory elements, and wherein said coding sequence is
   a. a nucleic acid comprising a nucleotide sequence having at least 95% sequence identity to SEQ ID NO: 19, SEQ ID NO: 18, SEQ ID NO: 16, SEQ ID NO: 21; or
   b. a nucleic acid encoding a polypeptide having at least 95% sequence identity to SEQ ID NO: 20 or SEQ ID NO: 17.

2. The nucleic acid of claim 1, wherein said gene allele is:
   a. a nucleic acid comprising a nucleotide sequence having at least 97% sequence identity to SEQ ID NO: 19, SEQ ID NO: 18, SEQ ID NO: 16, SEQ ID NO: 21; or
   b. a nucleic acid encoding a polypeptide having at least 97% sequence identity to SEQ ID NO: 20 or SEQ ID NO: 17.

3. The nucleic acid of claim 2, wherein said gene allele encodes a pentatricopeptide repeat ("PPR") protein comprising an amino acid sequence having at least 98% sequence identity to SEQ ID NO: 20 or SEQ ID NO: 17.

4. The nucleic acid of claim 1, wherein said gene allele comprises the nucleotide sequence of SEQ ID NO: 19, SEQ ID NO: 18, SEQ ID NO: 16, SEQ ID NO: 21 or wherein said functional restorer gene allele encodes the polypeptide of SEQ ID NO: 20 or SEQ ID NO: 17.

5. A chimeric gene comprising the following operably linked elements:
   a. a plant-expressible promoter;
   b. a nucleic acid comprising a nucleotide sequence encoding a polypeptide having at least 97% sequence identity to SEQ ID NO: 20 or SEQ ID NO: 17; and optionally
   c. a transcription termination and polyadenylation region functional in plant cells,
   wherein at least one of said operably linked elements does not naturally occur together with respect to at least one other element.

6. The chimeric gene of claim 5, wherein said promoter is capable of directing expression of the operably linked nucleic acid at least in anther or tapetum, or developing microspores.

7. A cereal plant cell or cereal plant or seed thereof, comprising the nucleic acid molecule of claim 1, wherein said cereal plant cell, plant or seed is wheat, spelt, durum, or *triticale*.

8. The plant cell, plant or seed of claim 7, wherein the polypeptide encoded by said nucleic acid is expressed at least in anther or tapetum, or developing microspore.

9. The plant cell, plant or seed of claim 7, which is a hybrid plant cell, plant or seed.

10. A method for producing a cereal plant cell or plant or seed thereof, comprising providing said plant cell or plant with the nucleic acid molecule of claim 1, wherein said providing comprises transformation, crossing, backcrossing, genome editing or mutagenesis, and wherein said cereal plant cell or plant or seed is wheat, spelt, durum, or *triticale*.

11. A method for producing a cereal plant cell or plant or seed thereof, comprising increasing the expression of a polypeptide encoded by the nucleic acid molecule of claim 1 in said plant cell or plant or seed, and wherein said cereal plant cell or plant or seed is wheat, spelt, durum, or *triticale*.

12. The method of claim 10, comprising modifying the genome of said plant to comprise said nucleic acid molecule.

13. The method of claim 11, comprising modifying the genome of said plant to increase the expression of a polypeptide encoded by the said nucleic acid molecule in said plant.

14. A method for producing a cereal plant or seed, comprising the steps of
   a. crossing a first cereal plant, homozygous for the nucleic acid molecule of claim 1, with a second cereal plant; and
   b. obtaining a progeny plant, wherein said progeny plant comprises said nucleic acid molecule, and optionally:
   c. obtaining seed comprising said nucleic acid molecule from said progeny plant, wherein said cereal plant or seed is wheat, spelt, durum, or *triticale*.

15. The plant cell, plant or seed of claim 7, wherein the genome of said plant cell, plant or seed has been modified to increase the expression of said polypeptide in said cell, plant or seed, and wherein said increased expression is in comparison to said plant before the genome of said plant was modified.

16. The plant cell, plant or seed of claim 15, wherein said increased expression is obtained by modifying the native promoter to include regulatory elements that increase transcription, or by inactivating or removing negative regulatory elements.

17. A cereal plant cell or cereal plant or seed thereof, comprising the chimeric gene of claim 5, wherein said cereal plant cell, plant or seed is wheat, spelt, durum, or *triticale*.

18. The plant cell, plant or seed of claim 17, wherein the polypeptide encoded by said chimeric gene is expressed at least in anther or tapetum, or developing microspore.

19. The plant cell, plant or seed of claim 17, which is a hybrid plant cell, plant or seed.

20. A method for producing a cereal plant cell or plant or seed thereof comprising the chimeric gene of claim 5, comprising providing said plant cell or plant with the chimeric gene of claim 5, wherein said providing comprises transformation, crossing, backcrossing, genome editing or mutagenesis.

21. A chimeric gene comprising the following operably linked elements:
   a. a plant-expressible promoter;
   b. a nucleic acid comprising a nucleotide sequence encoding a polypeptide having at least 98% sequence identity to SEQ ID NO: 20 or SEQ ID NO: 17; and optionally
   c. a transcription termination and polyadenylation region functional in plant cells, wherein at least one of said operably linked elements does not naturally occur together with respect to at least one other element.

22. A cereal plant cell or cereal plant or seed thereof, comprising the chimeric gene of claim 21, wherein said cereal plant cell, plant or seed is wheat, spelt, durum, or *triticale*.

\* \* \* \* \*

SEQUENCE LISTING

<160> NUMBER OF SEQ ID NOS: 28

<210> SEQ ID NO 1
<211> LENGTH: 101
<212> TYPE: DNA
<213> ORGANISM: Triticum aestivum

<400> SEQUENCE: 1
acctttatcg tctcttggta ctgtgatatt gagactggta agtaaggttc rgttggtgct    60
taatcaccat aggccatagc atgggccctg tcctagtgta a                       101

<210> SEQ ID NO 2
<211> LENGTH: 101
<212> TYPE: DNA
<213> ORGANISM: Triticum aestivum

<400> SEQUENCE: 2
cggcacaacc caagcaaacc acccaatgca cgtgccttca gctcctctgg yacgctcttc    60
aagaggctct ctgcttcttc cagaaggcca acactcccat a                       101

<210> SEQ ID NO 3
<211> LENGTH: 101
<212> TYPE: DNA
<213> ORGANISM: Triticum aestivum

<400> SEQUENCE: 3
tacatgatgg tgttatgtat caaccaacat tacagtgcgc ttgtcgactc mtggtcfttt    60 ctgactgtca atctcatgag agaattggct cgagaatttc g                       101

<210> SEQ ID NO 4
<211> LENGTH: 101
<212> TYPE: DNA
<213> ORGANISM: Triticum aestivum

<400> SEQUENCE: 4
tccatctttt tgttgagatt tactgaagaa cagccgtggc aaggcgctcc ygtgcaaaaa    60
ttcgtgctct cgtttgcctc accagcccct gttctgtttg t                       101

<210> SEQ ID NO 5
<211> LENGTH: 101
<212> TYPE: DNA
<213> ORGANISM: Triticum aestivum

<400> SEQUENCE: 5
tccttcagac atcgaacaca tcatcataca tgtcggcgtc ccagtccgcg ycgtcgatat    60
aatcctccat gtcatcaaac tcggcatcct cgtcgtcgtc g                       101

<210> SEQ ID NO 6
<211> LENGTH: 250
<212> TYPE: DNA
<213> ORGANISM: Triticum aestivum

<400> SEQUENCE: 6
accaggtgcc gcttgaaggc agatcagaag argttatgac tccttcatgt acatcttggc    60
cgcgtcttgt tttaggcacc ggcggcagca gcagcaggga gtctcttaga accattgttg   120
tgcaaaactg gccttgccgt ctcctcttcc tttttcaat ggagaagctg ccgcaggtgc    180
ttgtggatta catttcatat gatactcact cccaccagcg caagttgtct ggaggttttt   240
gaagtcaacg                                                          250

<210> SEQ ID NO 7
<211> LENGTH: 101
<212> TYPE: DNA
<213> ORGANISM: Triticum aestivum

<400> SEQUENCE: 7
ggcagagccg gtcgacggag aggagcgcca ttcgacgcgt cttccgcaat rtgtttgcct      60
gcttcggccg cggccattcg gcgagctccc acgcttcgtc c                         101

<210> SEQ ID NO 8
<211> LENGTH: 93
<212> TYPE: DNA
<213> ORGANISM: Triticum aestivum

<400> SEQUENCE: 8
ttccggcagg tcttaaccaa ttccaatttt cattatccaa gcatagcact kaatcttgca      60
tttratcata agcttgttga ctggctaata ctr                                  93

<210> SEQ ID NO 9
<211> LENGTH: 101
<212> TYPE: DNA
<213> ORGANISM: Triticum aestivum

<400> SEQUENCE: 9
ctgaaggaaa gggatccatg ggtaatacac cgtgtacatt ctaggggtc rtgtgacagc       60 agaatcaact taattttga cgagcaacca aataccgact g                          101

<210> SEQ ID NO 10
<211> LENGTH: 101
<212> TYPE: DNA
<213> ORGANISM: Triticum aestivum

<400> SEQUENCE: 10
tccatctttt tgttgagatt tactgaagaa cagccgtggc aaggcgctcc ygtgcaaaaa      60
ttcgtgctct cgtttgcctc accagcccct gttctgtttg t                         101

<210> SEQ ID NO 11
<211> LENGTH: 101
<212> TYPE: DNA
<213> ORGANISM: Triticum aestivum

<400> SEQUENCE: 11
tcatgtggct tgccatgttc cagaacatgc tgaacaacat agttaccata ytgatcttga      60
gccagcaagc aaacagactg gagaatctca tccatcatta t                         101

<210> SEQ ID NO 12
<211> LENGTH: 101
<212> TYPE: DNA
<213> ORGANISM: Triticum aestivum

<400> SEQUENCE: 12
ccaattatca acctcctgac tgtgagggaa acaaagggaa tagatagatt rctccagtac      60
acatcacgag gttctggagc ccattcagtc agccaaaggg t                         101

<210> SEQ ID NO 13
<211> LENGTH: 101
<212> TYPE: DNA
<213> ORGANISM: Triticum aestivum

<400> SEQUENCE: 13

```
atgaagcccg ggttcgatcc tagcaagggt ggacggccgg agttttactt ygaggaaggg      60
tctgatcctg agcaggtgga ttggataggc caaaagaacc a                         101
```

<210> SEQ ID NO 14
<211> LENGTH: 293
<212> TYPE: DNA
<213> ORGANISM: Triticum aestivum

<400> SEQUENCE: 14

```
ttggctggta gcactgactg gtcaaacctc tatatatagc ttatccaatg gaatacatat      60
tgtccgacgt ctctcttgtc aaaagtatta gtggaacatt tgctcgawgc ctttactaga     120
cccgtccaaa tgtctggtag tacacacatg aaatggaagt ggtgtcgggt aaacataaac     180
tggaagtaaa taaatttaac gtctctcttc tccttttcgc tttcgcattg tctcttttca     240
tcaacaatga cccgcgaaga taatcatcgg gcacatcctt tggttcctcc tga            293
```

<210> SEQ ID NO 15
<211> LENGTH: 22463
<212> TYPE: DNA
<213> ORGANISM: Triticum aestivum
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (15617)..(15617)
<223> OTHER INFORMATION: n is a, c, g, or t
<220> FEATURE:
<221> NAME/KEY: misc_feature
<222> LOCATION: (16309)..(16369)
<223> OTHER INFORMATION: n is a, c, g, or t

<400> SEQUENCE: 15

```
gtagggtccg cacgcttaac gttacgatga cagttttatt atgagtttat aagttttgat      60
gtaccgaagt ttgttcggag tcccggatgt gatcacggac atgacgagga gtctcgaaat     120
ggtcgagaca taaagattga tatattggaa gcctatgttt ggacatcgga aaggttccgg     180
gtgaaatcag gattttacca gaacaccggg gggttaccgg aaccctccaa ggggttaatg     240
ggccttagtg ggccatgagg gagaagagga gggccggcca gggcaggcca cgcgccccct     300
cccccctagt ccgaatagga caaggaaggg gggggggcg gcgccccct tcctctttc       360 ccctccccc tttccttctc caccaaggca agaggggga gtcctactcc cggtgggagt      420
aggactcctc caggcgcacc ccaagggggac cggctgcacc tccccttccc tcctttatat     480 acggggggcag gggggcaccc cataacacac aagttgatct acagatcgtt ccttagccgt    540
gtgcggtgcc cccctccacc atattccacc tcggtcatat tgtcgcggag tttaggcgaa     600
gccctgcgcc ggtagaacat catcatcgtc accacgccgt cgtgctgacg gaactcatcc     660
ccgaagcttt gctggatcgg agcccggggn agctttgctg gatcggagcc cggggatcgt     720
catcgagctg aacgtgtgct gaactcggag gtgccgtacg ttcggtgctt ggatcggtcg     780
gatcgtgaag acgtacgact acatcaaccg cgttgtcaga acgcttccgc ttacggtcta     840
cgagggtacg tggacgaaca ctctcccctc tcgttgctat gccatcacca tgatcttgcg     900
tgtgcgtagg aaatttttg aaattactac gttccccaac aaggttgtgc tcaggcggag     960
cttcatgccc gccaaccgca ggagatcgcc agacatggcc ggtgaacact gggtcccgat    1020
cgctgacgat cgaagagggg aaccccgtgga ggcggacgat accgtcgaag aaggcacggg    1080
```

```
ccacagatgc agcagtgtaa ggatgaccga gcgtgatgaa gtgagcatac ttggagaaat    1140
tagtacaagg ccttcagaaa ttcctccata attttgtaca ttttctgtta aaatttgtag    1200
atccacatgc gtaagtactg gacacgcttc ctcaagaaga agaatgacat agtctcctgt    1260
gatgacgctg aggccatcgc cgtattcaaa tccggcgtaa ccgacgtgtg atactctggg    1320
ggatttgatg ataacccccc cagttcatgt cactttgatc ataaccccccc ctttgtgtca    1380 ctgacatgtg gggtctggtc ccacatgtca gtgacacaaa ggggggggggg ggttatgatc    1440 aaagtgacgt gaactggggg ggttatcatc aattattccg tgatactctc cagggacttc    1500
ggatacttca agcccaggac catgccggcc ttgatggaga tgtggcgcgt agttcgcagt    1560
atatgtggga agacactctg gatctacaaa attttaatag aaaatgtatt catttgatag    1620
ccgcacacaa aaaaaggca aaatcatttg ccattttctc ttctgtaccg ctcatggttc    1680
aaaagagttt tcctgaattt tgtaaattca tagtgtattc ttgcacttcg atgtgagatc    1740 ccccccccccc ccccccctga aatttttgaa aactaataaa tgccttttgc atatactttt    1800
ttccaaataa aaggatggct tgagcttcag agccggattt ttttttttctc gtgcaatact    1860 taccaaattc ttgttcataa aatagtattc atagacatat atatacccaa atgtgcaacg    1920
tttcttgggg atctttccat gcatgtgtta cgcctgtttg ttcagagaaa gtatgattca    1980
gaccaaagag aaaccatttc tggagtgttt ctcgaagaat ggttctgcta aattagtact    2040
cctacaagaa tttcaggtcc aagatcttca ctgctaagtg agtaaatgaa aaattatgag    2100
gaaggaagaa gataaaagaa aaatactgaa catgggagaa aataaattgg acagtgaata    2160
taatgaaata accaggttct gcttctacaa cgcacagcta aaagaagaaa aaaagcacac    2220
caattgttct atagtaacaa aatgcaccaa ggaacagggg agaaaaccat ggcaaagctc    2280
actgaaatcc atcagactct gtctcaaaaa aaggtaatga gatgaatgaa ccgatctact    2340
ccctctgtct cataatgtaa gacgtttttt ggcactagtg tagtgttaaa aaacatctta    2400
tattatggga cggagggagt ataatttttag ggcacactat tgttggatag aatagataat    2460
aacaatgacc ctgtttcatt aacaaaatag taccacatat cagtttaata tatactgcct    2520
gcttactgtt catactacca aagccaaaaa gaatagagaa tttatcacct ctatcggacg    2580
gaatagagaa gttcaaaatg catcaaacat actatatcct tattatagtc ataccggcat    2640
gatatacaga gtattgaata acaaaggaac atgctgacag tcgatgaaat tatggacaga    2700
accatattac ctctgaacat tgatatgcca cagagtatgt ttaattcaac gtttaaaaat    2760
gccgaggccc ctgatattga tctggttaag ccaagttaca gggttaaact caacatggtg    2820
ctgaatcgat caaaacaaat aatttggagc ccggccctaa attaatcaat gccagcatat    2880
acaaaacact aacagtcaca gtcacagact gctacaacgt gatccatgta gccatacaag    2940
gcagaaggtc tagaagctgc acaaataata acacaattac ataagcatat gtgattcaca    3000
gatcacccta ttcatcaagt ggctggcata aacatagga gtattaccca tcaacagtca    3060
acaaaacacc tgtctagtac cctgttatga ttaactaacc tcaaactggc ttcggcaggg    3120
acaagctggt caagcacctg ttgctgctca gcgttttcaa attctttctc gaaccagaca    3180
aaagagacac gctcgctgat tactctgaaa cttttggtgta tctggtggct gagaaaacat    3240
ttgcaacagc tacgccgaga aattggttga ctccattccc tgtgaggcca agccatggat    3300
gctggcagca gaaagggac ttacacaggt gccactacat gcccggccgc ctgaatctct    3360
cccgtaggtg ttctactagc agacatacaa cttcaaaaca attgctggtc ctacagttga    3420
```

-continued

```
attgtactct ttgcgtcatc ctgatggctt gttctcaact gccttcctat ttacatatgg    3480
aaattgcact tgttgtacaa gcagataaac tcatggcaaa caataattca accttacctt    3540
ctgaggagtt aagttcagat atcatgtaaa accattcaac tgtagctcat tctccgcgaa    3600
actgatactt tgcggggagc aatcttatct gttctctgta tttcccttc cctgaaaaga     3660 gagagatcag cagcgaaaca gttttagctt caagtgagta gctctttgca tcaactttag    3720
acataaggag ggaggaaagt gaacctattc cttggctatt ttggttcacc acaaatctac    3780
tttccactga ttcatagtgc attcttacat gtacaagtga ggtttgttcg ggatgtttga    3840
ttataactta caactgtact ttctgaaaaa aaaagatcaa tgaatctccg aaagccggaa    3900
aaaatctgct cccagaatag accaatttat catttcaaag agtcccaaca ttcagagtac    3960
atccatatgc tgctacaggg tgtgctactc cattacagct gcgattgcaa gatctgaaat    4020
acagtcatac atattttgtg ctaggtactc cttcagttca gctatagtgc aaaactgaat    4080
ggaattatga gatgcaaata gtactatatg attagacaat tatgcccagg caccagccaa    4140
cttatggaat acaagaatgg gttctctttc agaaaaatag tactggtatg atttcaggtc    4200
caagactttc actggccact gccaaggatg tttaggacga tattgaattc cttctatagc    4260
ttacacctac atgacccagg aaaacagttt ataacattct tacgatcgcg aaaacacact    4320
agcgttcttt cgtacgtact acaaaccatg ttgctttaca aaaattcaaa aatcaaaacc    4380
cttatttcgg gaagaagaaa aagcatcata cgtataaaaa atgctaccaa aatatttact    4440
aaattctttt tcaaaaaata gtattcatgc atagacatat ctaccaaatg tgcaatgttt    4500 cttgggatc tttccatgca tgagtcacac ctgtttgttc agagacaata tgattcagac     4560
ccaagacaaa ccattttttgg agtgtttctc gaagaatggt tctactaaat tagtacaaga   4620
atttcaggtc caagacctgt actactcagt gagtaaatga aaaattacgc ggaaggaaca    4680
agataaaata aaatgctgaa cttctgagct ctcgtaagaa aataaattag acaatgaatt    4740
aatgaaataa acaggttttg ttgttctata acgtacagcc aaaagaaaaa aagcgcacac    4800
caattgttct atagtaacaa aatgtaccaa ggacgggcga agctcaccga atccatatg     4860 agatgaatga accgatctat aattttatgg aacactattg ctggataaaa tagataataa    4920
aaaggaccct gtttcactaa caaaatagta ccacatatca gtttattact gcctgctttc    4980
tgttcatact accaaagcca acaagaatag aaatttatca gctttatccc aagaaacaga    5040
gaagctcaaa atgcaccagc cgtatatcct tattatagtc ataccgccgt gatatacaga    5100
gtactaaata aaaaaggaac atgctgacag tcgatgaaaa ttacgggcag aaccatatta    5160
cctctggaca ttgatctgcg tcagtttgtg caacaacaga gagtattgat attgtgattc    5220
ctagagataa caccagcatg atctagttaa gccaagttac agggttaaac tcaacatggc    5280
gctgtatcga tcaaaacaga aaaattgcag accagccctc atattaaatg ccagcacata    5340
cagactacaa ctgcatccat aaaacatgta catggcaaag agagagcccc aaaaataact    5400
agacaagcat gtatgattca gacttctgca tgcttcacaa gtcaccctaa tcatcaatgc    5460
cagcatatac aaaacactaa cagttacaga ttgctacaac tagatccatg tagccatcta    5520
caaggcaaaa ggtctagaag ctgcacaaat aataacacaa ttacataagc atatgtgatt    5580
cagacttttg catgctgcct cttcacagat caccgtaatc atcaagagga tggcatataa    5640 catattcacac atcaacagtc aataaaacac ctctctagta ccctgttatg attaactaac    5700
ctcaaactgg ttccagctgg gacaagctca gctcttcaaa ttctttctcg aaccagacag    5760
aaggggcaca ctcgctgatt aatctgacca tgcgtatctg gccgctgaaa acaattgcat    5820
```

```
cttcaaggga gccacccaaa accgacggga attggttgac tcgattccgt gtgaggctaa    5880
gccatggatg gtggaagaag caaaggcgct tagacgccag ccactacatg ccccgcctga    5940
cagtctcctg tagttgtttg gctagcagac tgtccagctt caaaaaaaaa agtttgctgc    6000
tccttctgtt tgagttttga ttcagtgttg ttttggcagc cctagttctg ccttttttatt   6060 ggtggtgcaa ctgaattgta ctctttgcgt catcctgatg gcttgttcta aactgacttc    6120
ctatttacaa atagaaaatg catttcttgt acaagcagac ggacccatgg caagcgatgc    6180
aaattaaatt tcagatatca tgtaccaact attcaactgt ggctgcttct tccagaaact    6240
gatactttgt aggaagcaat ttgatgtgtt ctctatattt ccctttcctt gaaaacagag    6300
agatcagcag cgaaacagtt ttagcttcaa gtgagtagct ctttgcatca actttagaca    6360
tataatttcc agccttgact atctctcctt tttccagtaa ccttctgatg atatgattta    6420
acaggcaaga gttggcagta cagccgctct tctccatgga taagaaaaga ttgtcagctt    6480
cttccactga accttctttt ataagatttg tcatcattac ggtgtaggta acagcattag    6540
gaaccaagcc attggctggc atagcagcaa acaaatcctt agcctcttgg tttctctcga    6600
ccctgtataa ggcaccaata atgatattga caattgtaat atcaaatttc acattcattg    6660
cgcttaattt ccggaaaagg gtgatcgctt cgctactgca gctatttcta caaagtccac    6720
caagaattat agagtatgta tcaatgcaca cacttactcc agattcaacc atctcatcaa    6780
acttctcttt tgcagcaaca gtttgtccag ccagaaataa tccatccagt atgacgttat    6840
aattaaaagt tgtaggttta agtcccttgt gcagcatctc tttgaacaga ataagcccgt    6900
catcaatcct tctattttttg caatagccat taataagtat accatacgta aagttacaag    6960
gttctaaacc atatgacacc atatcatcaa atactttcaa tgcatctgcc atcttgcgga    7020
ctaggcagta tccaccgatc agcaaattaa atatgataac attaggcctc ataccaatgt    7080
gcactatcaa gtcaaggata tcccgtgctt ctgttaccct tccttctgtg cataggttct    7140
gcatgattga actgaagaac ataatatcag gaggaggcat acctttcttc atcatttcag    7200
taacatattc ctttgctttc accaaatcgc catgtgtaca aaaaccctgg attaggggac    7260
gataaacaga tgcgtccggt cgtactcctg tatcaatcat ctgattaaac tttatcacag    7320
catcatccaa cctacccttc ttgcaaaatg catgtattac ggttgaatat gtgactgcat    7380
ttggactcac tccttgtttc tgcatttcat tgaagataag catagcctta tcaagcttcc    7440
cagatttagc atatgcatta atcagtatgt tgaatatatg acagttaggt agaatgcagt    7500
gtgttgccat ggaattgaag agattgatca tgtcaactag gcatcctcg gtggcatacc     7560 catgaaggcg aatagcatat gaaacgttgt caggtttcag gcccttgata gccatggtat    7620
caaaaattcc tgcagcttct ttgcttcttc catgttgca aagaaaggtc ataaacatgt     7680
tgtaagtatg cacatctgct gtaaccctcc gacttgtcat ctctttgaat accctaactg    7740
cctccttcca gtggcctgaa gaggaatatc catggatgag gctactatac gtcacattat    7800
caggtccaac accatcatca atcatctgac gaaggaccac ctctgccttg tccatggctc    7860
tggccttgca cagcgcatca ataactgagt tatatgtcac cacattaggc ttaacgccct    7920
gctgcgccat ttcatggaac agattgcagg ccttgcttac atggccttcc ttaaagaagc    7980
catggataac ggtgttatac gccaccacat taggagtgca gcccagctca ggcatcctgt    8040
gaagcagcac gtccagagcc tcatccgccc gctttgtgtg gcaaaggccc ttgaggaggg    8100
tgttgaagac gacttggttt gcctccaggc ccgtcttgag gagacggcca agaaggcga    8160
```

-continued

```
gcaccagatc tgtgcggcaa gcgcggcagc agcagtccat gaggacgcca taggtgaaga    8220
catttggctg cgccacccgt cgtccgacgt ctcgggacaa acggccgaag agggtgactg    8280
ccagggcggg gccatcgcag caggatgcgg acgcgggcgc gcgggcgagg gcagccagaa    8340
atttattcaa gggacgctcc tggacaggat tgccccgccg cagcaattcg tcaaacaggt    8400
ggtgtgcgtc ctccgtagtg agcgtgccag agctcgcccg ctgtgccgcg gcggcgaagg    8460
cggcgtgggg atcccagatg cgtgagggat gagaggtgga ggaggagtgg cgggcgcaga    8520
gtcggaggcg gaggcggagg cggggtggcg acattggcgt ggtggaggag aagcggggca    8580
tggccggtgt gtaggtcgcg aactcaactg ggagcaggac gacggggctg tgcttttcca    8640
agttgtacca atgtgaatgt gctaggtggc aaccttcagt tatcttttt tttagggtag     8700 ttatcttact ccctccgttc ctaaataatt gtctctctag gatttcaac aaatgactac     8760 atacggaaca aaatgagtga atctacactc taaaacatgt ctacatacat ccgtatgttg    8820
tagtttattt gagatagcta gaaagacaat tatttaggaa cggagggagt attatctagt    8880
actccctccg ctcggaaata cttgtcaggg agattgatgt atctagatgt attcttgttc    8940
tagatgcatc cattttcatc aaattcttcg acaagtattt ccggacggag ggagtatgta    9000
gtactactac tactattact tacttttgc aggtaaaatt aaattatggt ctcatatggc     9060
tatattcata tcacataatt tatcagatta aatttat tagaccaaga atataaattt       9120
agttgtaagc cctagaaata tactaggaag ccatcaaatt atactagtat ttttaagtat    9180
tcccatagaa aaatgtattt ttaagcattt agttttta gcatctttat tttttgaaag      9240
agttaaatgc actcaaggtc ctaaaaaatt cgtcagggtg tcactttagt cttatttcgt    9300
ccaaaatgca cctttaggtc ctaattcttt agtaagtggt ttaccctagg tccttttct     9360 cacgagcgct cgttgacctg ctcgtgtggt gcgttgaccc atgccaaatc gacagaaggg    9420
ctgcgtaggt tgctcttct ttttacagaa accccttat aaacattatc ttctcattcc      9480
ccagtccctg gctttatttc ttccccaaat ctgctctctc tctcggcgcg cgcgtccct     9540 aaacctatcc atggccggaa cttcaagctc ctcggcaagg aaacaactaa gatgaggagc    9600
atggcaacat cctcagcacc gccgccggcg cggcgaagca agctccaact tcggcgggta    9660
tgttgccgct ggtggtgtgt ccttttgcc gtgtccgtat caccgttatg caaatcaaag     9720
taaatcaagg actacaacta ttgattatga caaagttatg acatattaga agagctacag    9780
gagaagatca tcgacaagat tagggttctt acggtaacat ggaggaggat tgctcactgg    9840
ccgtcataga agggggcatct tcacgggcac ccacacaaat tacctccaga tcacctccgg    9900
ttgcctctgt cgctcgcctc caatgtcgcc aaagtaccgt gaaagaggag agagggtgcc    9960
actaagaggg gggggggtct ctttgcgaag cttctcgcct ggcggttaga ccctctatcg    10020
atgtggcatg ggtcaatgcg gcacgtgtgc tggtcagcga gcgctcgtgg aaaaggacct    10080
cgggtgaacc aattaataaa gaattaggac ctaaaggtgc attttggaag aaataggact    10140
aaagtgacac cccgacgaaa cctttaggac ctccagtgca tttaactctt tttgaaacga    10200
ggtaaaagac ttgccatttt cactgattaa gaagaagaga gttgcccggt taattaaaac    10260
acgcccatcg aatagggcac tccagccgac ctggcactga caagatcaca cacatactgc    10320
tgacgagagg acaccgtcga ggctgcaatg tcatcgtcat cgcctctcca cgagcaggca    10380
actccgattt cctcgctgac gacccatcaa gaccctccg aacaaacggc acccgaggac     10440
ctcgacagcc aagccaaatg atcggccgca ggcgtcgagg accgacatct ccgatttgt     10500 tgatgagcat cacaggagaa agttgcaagc ctcacaccaa gctagtccag tgcaacctgc    10560
```

```
ggagagcatc gtccgccgaa accaccctca tggagtcatc attgccgcag ggccccgcc   10620 gcatgtagct tcaacttctc tgtcacagtg agaaacaagc acagacgcac ccaaagggga   10680
accgaaccgc cgatatcaga aggacaagcc gcgacccagc ttcgcgcatc accatcttcg   10740
tcaccgcacg agtcgcaacg ccaaccactc gtatcaccgg ttgagcacca gccaaccatg   10800
acaccatgca cgaccagccc aaaggtagca cgggaaagga taaccggtct tcaaagcaac   10860
gccccaaagg gggaaaacac cgtacggacg acatcgttgc ccgacctaga tgggcgaggt   10920
tttcgcctga agaaccagat tcgagattgt agtaggtcga agaactctac aacaacgcct   10980
tcaacaaggg aaacgacgcc cataggcgcc gccagcaccg gccggccata gccgggcaag   11040
cttgcgcttg gagcagactc aaccaacacc ctcacgcagc cgacacaagc tggcccgcgc   11100
aatcgctggc atgcacaccc ctgcgcagca accgcgccat cgcctcacaa ggcccacggc   11160
ccaccataga gcacacacac ccccttgctg ccagaggcaa ggtcaccggg atgaccgacc   11220
ctgagtaaga tgagagacga gctggatccg aatgaagaac cgccggatct ggcgcccct    11280 tgcagcagca ctacaacaac caccaagggc cggccagagc agtcgacctg cgcggagacg   11340
aatgaccaaa ggaaggaaag ggggggccgcc accccgccca tactcgccga gcaagagccg   11400
ccggaccgaa gcccaggagt tgccgacga caccaccgcg actgccaccc gctggagacg    11460
caacttcgga gaatcttcgt gccgtagccg ccgcgccgca ctgcgaggag gcgtgcctcc   11520
ctcaccatga gacccggacg ctgcagagag gccccgccgc cgtcgtccac cgcacaggct   11580
tagcccggcg gcctcctccg gcgacggcga ggtagggagg cggaggggc gcccgtgtct    11640 tcaaggagga tgtgtggggg atgggggggg gggggggggg ggggggggg ggggggggg    11700 gggggtatc tttttagcat ctaggtggtg aattttgtgc cgtgaaatcc cgcccatgtt    11760
gtcccaacta aaagttggaa gtctattact agtggtggcc gaggttctca acgccttccc   11820
ttcttcagat gtgcctaaca tgcgtaacat gaccaaatgg tgttttgtga tgcgaaccat   11880
gtcttctgat gtcgttcgtt gtgctccggg atcagatgct tttgggtaat caactcatgg   11940
acggggagaa tggcaagatg ccacacggga tgcctggaaa atgaactcgg catgatgact   12000
ttctcatgac aggatggtgt cacgttgatt accccgtcgc gtcgaaagcc aaatagtgct   12060
acgtcaaaat gggcagatag agatggtgaa tcaagccatt ggtggtgtca gtcctgattg   12120
accatttgga ttccgcgatg atgtttaagg cattttctca ctacaaaaat tcccccaaga   12180
tcagacatca tcatcacatc tcggtatcct cttacttaag tttgcttgga gctccatctt   12240
gggttgtggt gacccaagta ttaaattttg ttgttgggta taacactgga tctacaaaat   12300
tttcatagaa aatgcatgca tctgatagct gcacaaatta ttattttttg caaacataca   12360
gtgatccata atatctgcaa acagacccta atgtctgcta ttctagatca cgccattttc   12420
ttttctgtac cgctcatggt ccaaacgagt ttcttctgaa ttttgtgaac ttagtagatt   12480
tcttcttaca cttagggtgc gtttggaagc cgaagtattt ttgtggtttt ctggaatact   12540 gtggttttg aaaaaaactt tggtatttaa tactttgagt cgtttggata aaaaaaatac    12600
tgcagttcaa caaccatga tatctctaaa actgtggtat ttttgttgta tataaaaaag    12660
aggccctgac ctctttttt taaaaccgag aaagcgctgg ctgctggtct ctcttgtgtc   12720
caacttctgg ccatcaacga ctgtgatgca taaatcgata ggtagcccat cgatatgtcc   12780
ggctggaggc ggatgtactc gtacacgagc tgcaaacgtc gaccttcagt gcatgtgtta   12840
actacctcgg tctttgattg attacaagag ataactctac tgtagatctt agcatctagg   12900
```

```
agaacatgct catgcaaggc tgaatgcata cgatggctat tagtacaagc tgatccctga    12960
gtgtagctga atatgcatgc atgtaacagt cgatgcaaac caaagaaaac tgagaaaaac    13020
tgccacttgc caaacacctc gcagttttat caaaactgag aaaaactatg gtttttagaa    13080
actgaagtat ttattgacca tgtattgaaa tacttaggtt ttggaatacc atggttttga    13140
aaaaacgttg ttgagatgtg acatccccccc ccccctcctc caaagttttt gaaaaaaaaa    13200
ctaaaaataa tgatatttaa tatattttcc taaaataaaa ggatgaattg agctctggag    13260
ccaaaaaaat cttccgaaat atttaccaaa ttcttgttca caaagtagta ttcatggaca    13320
tatacagaac caaaatgtgt aatgtttctg ggggatcttt ccatgtatgt tattgttgca    13380
agcattcaac actaattgta attcactgta ttagtcgcgc cagtttattc agagcagaca    13440
aacatgtgca tggagctgcg gaaaccattt tttggagtgt ttctcaaaga acagtctgct    13500
tctgaaatta gtacaaaaaa ttcaggtcca agaccttcac ttctcagcga gtaatgaact    13560
attatgagga aaaggaaaag gctgaacttg agctctccta acatataaaa ataaaaaggc    13620
aatcaatata acaagataat gggattctgc ggttcagcat aaagaaagac tgttctgcat    13680
cagactccgc cccctggaaa aagaggtaag atgaatggac tgatctatga attaggacac    13740 acttttttgtt ggagaaatac acactactat agctggatcc atacaacctg ttaatatgca    13800
gtggcataac tgaatggaca gtgcctctga gttcttcaaa attgttccaa cttccttagg    13860
gagctggata cacgaagacc atattcatag tctgtctatt atgaatttaa catttctttt    13920 tcttttttcga ggaggtgatt atcagaacca agagcaaaat aaccccaatc ctaaatggta    13980
tgtattatcg cttgcctaaa agatgaaaac tagtgacgaa acctaaatca agatgagcat    14040
ggtataaatg gtaaaacggg agcaattcca agcatgtgcc cttggatggt gttgcagatg    14100
tagtagaaga ggtggagcac atgataccac ggcgcagagc tctgtcattg acgaggcagt    14160
tcaggttcat ggtggaggca caggtgtcca tgccctgcag caaaccgatg ctgttggaga    14220
gcacagccac cagtatatac taccgagcta cgacataacc agcccaaag aagcgtcgtg    14280 ttttcaactt cctctgcaaa aaagaggatg aagtcagagt agtaaatatg cacagaaatg    14340
taagcggttc tgacagacag ttgtgagata ggaccctgca aatgcaaagt agccacagta    14400
cagaaagatg tttaagcaac aagaccaaat ctcctagcct tcaacagtac agtacaaatt    14460
tttggagtga gacatttaac acttgactct ttaaaaaatt gtacgaaatc aacataatgc    14520
caaatgctgc agtccaacat gcatacagaa ttacatcagg ctcaaaggaa gcacaggacc    14580
tttacgttct gtctccgagg aacagaggaa aaacaaggta aagcttcgag ggccagattg    14640
ctaccgctgc tcaattggtt gaacggatca agcatggtta cctgatttcc ctttgacaaa    14700
atctttatga ccttcagagc atgatgaaac atagtcaatg gattcacctt ttcagcctta    14760
acagctttcg tggcccatca tagtgacatc ccagcttcac cttcaacctg aacacttgtg    14820
ttcattaaaa aacaatttgg tacacaacaa ctctgaattg gacatagtct cgcgagcaca    14880
gtagtacaat tttcagatag aacccgtgac aatgatgaag tccggcatct ccaagtgccc    14940
aaaaatttca tccttgatct gcaaaactat tttacagagt gcaggctttg ctgcccaccg    15000
agcaatacaa ggcaccatgc ttttcattg tcagaacggg atccaccatg ttgccagatt    15060
ttgtccccgt attgaactgt gtccccggtt ggggacgtca gaacgacgct agccccagg    15120 ccagccaaca ttttggagcc gttgaagtgc atgatccagt tggagtatgc gccgtactct    15180
ttagggagtt cggcttcagt ccattcggcg atgaagtcgg ccaaacctg cgacttaata    15240 gctcgccttg gcttgtaggt tatgtcgaac gggaggagct cgatggccca tttggcaatc    15300
```

```
cggcccgttg cgtcgcggtt gtttatacta tcattaaggg gtacttcgga tgccactgtt   15360
atggagcaat cttgaaagta gtgtcgcagc tttcgggatg ccatgaacac cgcgtatgct   15420
atcttttgat aatgcgggta ccgtgacttg catggagtta gtacagtgga cacgtagtac   15480
actggttttt ggaggggaa cttgtgtccg tccgcttctc gttcgacgac gagcaccgcg   15540
cttacaactt gatgggttgc cgcgatgtat aatagcattg gttcgcccgt gttgggcgcg   15600
gccaggaccg gatttgntac aacttgatgg gttgccgcga tgtataatag cattggttcg   15660
cccgtgttgg gcgcggccag gaccggattt gttgccagta tggcttttat ttcttcgagt   15720
ccggccgtgg cagcatccgt ccactcgaag tggtcggtgc gccgcaggag gcgatagagg   15780
ggtaatgcct tttctcctaa gcgggagata aagtggctta gagccgccac gcatcctgtt   15840 agttttgta tttgtttgag gtcctttggg gtattcaatt gtgacagagc tcggatcttg   15900
gctgggtttg cttcaattcc tctaccggat acgatgaagc ccaagagctt tccggctggt   15960
acgccgaaaa cgcattttc ctggttgagc ttaatgtcat atgttcggag attgtcgaac   16020
atgagcctta agtcgtctac tagagtatcg acatgttttg ttctgacgac cacgtcatct   16080
acgtatgctt caactgtttt gccgatctgg ttggccagac atgtctgaat catgcgctga   16140
tatgttgcgc cggcgttttt gagcccgaag gcatcgtgt tgaagcagaa tgggccgtat   16200
ggggtgatga atgccgttgc ggcttggtct gactctgcca tcttgatttg atggtagcca   16260
gagtatgcat cgaggaaaca caatgagtcg tgtcctgcgg tggcgtcgnn nnnnnnnnn   16320 nnnnnnnnn nnnnnnnnnn nnnnnnnnn nnnnnnnnn nnnnnnnnt tctttggtac   16380 catcaccagg tttgctagcc agtccggatg ttttatgtct ctgatgaatc cggcttccag   16440
cagttttgct agctcctctc ccatggcttg tctcttgggt tcggaaaaac gccgtagggt   16500 cttttgacg ggtttaaacc cttttatgat gttcaggctg tgctcggcca gcctgcgtgg   16560
gattcctggc atatccgagg ggtgccaggc gaaaatgtcc caattttctc gcaggaagtc   16620
tctgagtgcg gcgtctacat cgggtttaat tgtgccccga tggaggccgt ttttgtaggg   16680
tccgttggat ggacttggaa tttgactatt tcgtccgctg gtttaaaaga ggtggacttg   16740
gatctcttgt ctagtatcac atcgtccctg tccaccgtag agcgcaacgc cgttaatcct   16800
cggccgctag ggcctcagat aatgcctcca gggctagtgc ggctgtcagg accccgactc   16860
aatggcacac cgatctagca tgtaacacct catatcattt tgcggcctca cgcacggtgt   16920
tcccacgggt gtcgccttac caggcccggg accgtttgcg ccttttggct catgtatatg   16980
atagtgttgc tagcatccat atgacaagga gcccaggctg acatggctag tcgtgaaccc   17040
aaagtggcac taacttacag ggacaggcat acatgaccca tcaacgaacg tgtcggtcat   17100
cagcgagtga atccgggctg tagcaactgg gctagcagga ctccggtaaa ccggactgta   17160
gcaggctaac aggactccgg tagacaccgc gtgacatttc cccgaaggga cagacacagg   17220
aacgaagaag gacacatgcc ggccagccta agtgttccgg agcagtagca agctatcaag   17280
gctcagtgaa agcactagga gacatttcct ggtaagaaag gctaccaagg ataaacaact   17340
agatagtcag atcccacaca taccaagcat ttcaataata tacacacaat atgctcaata   17400
tgtgcaaata caacatggca tcacaacatg actctacaac tcaagtattt tattcaatag   17460
gctccgagga gcaagatatt acatatggaa ccacgtggaa ctactagcga gactgaagtc   17520
tctctgcaaa aaacataaat taagcaacgt gagtacaaat gtacccagca agacttacat   17580
cagaactaac tacatatgca tcagtatcaa caaagggtg gtggagttta actgcagaaa   17640
```

```
gccagatttg acacggtggc tatcctgaac tacgactgca agtaactctt ttgaggtggc    17700
gcacacgagt ccacatattc accatatcaa taccaccacta tggatccgct gccgtctccc   17760
tacgagaacg ccatccatag cactcacgct tatcttgcgt attttagagt atccactttc    17820
acttgtctat gaactgtaca ggcaacccag aagtccttta ccgcggacac ggctattcga    17880
atagatgata ttaaccctgt aggggtgtac ttattcacac acgctctcac cacttaccgc    17940
agtttacacg acatgtactc ggcaaccttc aagcggaagc ccatcgaggg tgtcggccac    18000
gacctgacta accacacaag tctctcgtcc aggtttatcg cttattcggg ttccatccgc    18060
atggagatcc ggccggggtg tcgctcacgg ccccaaacga tgtgagtagg gttcccaagc    18120
ccaccattcg ggtgccactt ggtacaccgt gccactgtgc ctagtctgtc ccaagcccac    18180
ctgtaccggg tgccacttgg tatactacta acactaccta caaacaccag aaactagttg    18240
caactcctgg acagagatca agttgattaa taagctgaga ggggccgagt taccggaacc    18300
caatgtgtgg tagtagctgt tcatggatca caaacacaga actcagttcc tgaggacggt    18360
ttcaatgaga caacccacca tgtactccta catggcctct caccgctacc tttaccaaat    18420
cttgttcaca cacttagctc acacacagta ggacatgttt acacacctcc gattcatccc    18480
cgatgaatca gacttgactc aactctaagc aatagcaggc atgacaaaca agcatgaatg    18540
agtaggcaca tcagggctca aacaactcct actcatgcta gtgggtttca tctatttact    18600
gtggcaatga caggttatgc agaggataaa tgggttcagc taccgcagca agtaacagat    18660
gaatcgttgt tgtcctaatg cagtaaaaga gagtaggagc gagagagtgg gattttatcg    18720
gaatgaacaa gggggttttg cttgcctggc acttctgaag ataatatagt ttcttcattg    18780
gtgtcattga actcatcgtc ggtatgtcgt ctattgggag ggaacaaaca ccgacaaaca    18840
aggaagaaac acaatcaatg caaattacaa tatgatgcat gatcatgaca tggcaatatg    18900
ctgtgatttg agctaatgca tctagcagta ggttaaatgg agttggtttg aatccaatat    18960
tcaaattcaa actccatatg tgaaggttta aatgccattt actgatttgt cctaaacaac    19020
agctctaagt tcttctaaca tgcatgcaaa tggtacagat ggatagatgg attttttcata   19080 tataatttat tagatttgga gctacggttg aatttctatg attttcagaa gttttgacca    19140
ttttctggaa tttcctaaaa agaataaatc cagaaaatga tttactgcgt cagcctaacg    19200
tcagaatgac attagcaggt caacggggca cggcccgggt caaacctgac ctgtggggcc    19260
cactagtcag tgactcagtt atctaattga gataattagt gctaaactag ccctaactaa    19320
gccgtcagca gtgcggggcc catgtgtcaa tggatcatct aattaactag ttaattaaca    19380
ctaactaacc taacactaat taaaaggggg cctgggccca cacgttagtg agagagaggg    19440
tcaaacccct gggcagacgg ggtcaaaccc cgccggtcaa agcggtcaac ccgccggcga    19500
ggacagatgc ggcggtgggc ttcggatttg gtccttcgtc gaccaaatcg acggcggaga    19560
taccctacgc gtagctgggg agctgccgca tccagtggtg caagcagttc ggtgcgggga    19620
ggccgggaac gtcggcgatc acgacaaccg cggtggccgg agttcggacc tcagcgagaa    19680
cggcgttgca gcgcacggca ggaacaacga gtgggtgcta tggactcctg acggtgtgct    19740
gagcatgttg cagtgctcga ttgcggtcaa ggctagctct ggccgcggcg gcgaggaacc    19800
acggcggcgg tgagttcacg gctccggtga ctcggcggc tagaggtgcg tacgggcatg    19860
gggagcaggg gagaagaagg tggagctcac aacggggtcg gtgatggtct cagcgagctc    19920
ggggaggcgg agacgcggc aaatcgatgg cggcgatcct tggtgccga ggaagggaac      19980 ggcggagcta gcggcatcta ggggcttccg gcgcctttcg tctgggtgag gatgaagagg    20040
```

```
ggggcgaggc ggagcttcct gggcgtcgg cgaggcgggg aggtggctgt ggccgtggcg    20100
aacggcgtcg gtggtgacgg tggcgctcga gcacgagttg cagagcgaga gggagagcag    20160 caggaaggg gatgagcatg ggagggagtc gagagggcc tgaggggtg cgtggcactg       20220 cggaagacat ccagggggga ggaggcagcc aggcagggag gaactggcct cctcggccgc    20280
gcgcgtgcga gcacgcagct gctcctactg gcaggaggaa gacgacagga gggagagcag    20340
tggtggtttg ggccagatgg ctgggccgcc agctgggccg gccaggtggg ctgcacgggt    20400
gaggccaggt actaactctc tctctctttt atttcagttt tctattttgt tattttgttc    20460
tgggctttat taaaaatgcc agggcatttc caaaaatcat gaaactaatc atggatactg    20520
tttagaataa aagcaacagt aaacatttta gtttatgatt atttgagcat ttaaaatatt    20580
taatagcatt taaatgccca aatgcaaata gagtatgatt taacccagag cccaaatatg    20640
tcatggaaaa atgtgcacca cctctggtta ttgcttctag catttccag aaaagatgaa     20700 cattttgaa agccatttgg attcacagaa aatattttta ggttgaacct atttgaattc     20760
catttggtac tagggtttgg acatccccat ttcaagtttc tttcaaagtt taaacatgat    20820
gcacacatga agggctagcc tactgcagac caggaccagg tatgtgacaa ctcaccccca    20880
ctaagcaaaa atctcgtccc gagattcaag cataggtaa gatgaagggg gaacgcaaac     20940
taacacaatc ttcacaatcc aggttgcact tcataggggc gttgattcga tcaccatctt    21000
tgactcgatg tcttcctctg agaactccaa ctaacaagac aagaagagga aaggaaaact    21060
ctagaagaat tgatcttctc gaagaccgaa caactcagga tcaactcatg ggatgagaca    21120
tagcagcatc ccccgagctg agacacgagg catacatcta gagggatgga gtggaacaga    21180
tgacgagggt tcactaggta gacaataatt ccacacttaa gaaggtggta acgattgtc     21240 aacgtagcga ggagttgagt tgccatgata ccataacggg gcaccttagg gaaggtgatt    21300
tgtagaaata tccccttaag tggcaaaaag aattacctt gatttagaga tcattgaaac     21360
tctttatacc agcctaaggc aattcttgag cgatcgtttg gagggggtcg gtagaatggc    21420
atgctttgat tagaatggat gatgtggatt accttgttga aaacaacaca agggatgact    21480
ttagtaactg aggagaagct caacagtaga gagtgagtcc actgtttgag aagttatagc    21540
ataaccgagg aagctgagag caaacccagt tagtgccgat gataacacct agcgcttgcg    21600
catgctctca agaacttgag catttccata ttcatcaagg ttttaccaac atctgtgtca    21660
aggatcctgg caacacaaca tactaccatg atggatagtg atggatgatg tatatgcata    21720
ggaagataac atcttctcag atttcacctt agcgaggcca aggaaacaaa atctggatga    21780
tcgaccgaga gacatttagc actccgcttc taatgttctc cttgatgtgc tagcgtaatc    21840
catagataat tatggtttga tatctagaac atcaagtaaa aggtcggact tcgggaacac    21900
aaaaatccat aaggaacaac tagggagtaa tcctacgaaa tccttatggg gaggtggcca    21960
acttcctcaa acaagatact acaataatag gtcttccggc tgggtgtgtt ggccatgaca    22020
tccactttac cggttatcga gggaccaaaa ttatagttct tgggaaaacg ttccaaccat    22080
catatctgcc tgagattcag atctggttgg tgtcagaata ttccagactc atcaagtcta    22140
gaaggaaaaa tgaaagcttg caacacaaat cgatgagatg tgttgcgaa attctcgggg     22200 aatgatctac agtagtaagc tccaaaacat gagctggttc tgctacacac atgtgaacat    22260
gttatcccag acaagcatga ccacatggta gtcttacaac aaaacactac cgagttctgg    22320
ttgggaacca tcatcgagga tatcggagtc ttgtgcatga tctagaatta acacaaccaa    22380
```

```
ttccttttcc ttgagcaaat caatcagtgg cttggggtgc tagggaatac atatgggatg    22440
aaggttgcaa gtctccaaac cac                                            22463

<210> SEQ ID NO 16
<211> LENGTH: 2346
<212> TYPE: DNA
<213> ORGANISM: Triticum aestivum
<220> FEATURE:
<221> NAME/KEY: CDS
<222> LOCATION: (1)..(2346)

<400> SEQUENCE: 16 atg tcg cca ccc cgc ctc cgc ctc cgc ctc cga ctc tgc gcc cgc cac     48
Met Ser Pro Pro Arg Leu Arg Leu Arg Leu Arg Leu Cys Ala Arg His
1               5                   10                  15 tcc tcc tcc acc tct cat ccc tca cgc atc tgg gat ccc cac gcc gcc     96
Ser Ser Ser Thr Ser His Pro Ser Arg Ile Trp Asp Pro His Ala Ala
            20                  25                  30 ttc gcc gcc gcg gca cag cgg gcg agc tct ggc acg ctc act acg gag    144
Phe Ala Ala Ala Ala Gln Arg Ala Ser Ser Gly Thr Leu Thr Thr Glu
        35                  40                  45 gac gca cac cac ctg ttt gac gaa ttg ctg cgg cgg ggc aat cct gtc    192
Asp Ala His His Leu Phe Asp Glu Leu Leu Arg Arg Gly Asn Pro Val
50                  55                  60 cag gag cgt ccc ttg aat aaa ttt ctg gct gcc ctc gcc cgc gcg ccc    240
Gln Glu Arg Pro Leu Asn Lys Phe Leu Ala Ala Leu Ala Arg Ala Pro
65                  70                  75                  80 gcg tcc gca tcc tgc tgc gat ggc ccc gcc ctg gca gtc acc ctc ttc    288
Ala Ser Ala Ser Cys Cys Asp Gly Pro Ala Leu Ala Val Thr Leu Phe
                85                  90                  95 ggc cgt ttg tcc cga gac gtc gga cga cgg gtg gcg cag cca aat gtc    336
Gly Arg Leu Ser Arg Asp Val Gly Arg Arg Val Ala Gln Pro Asn Val
            100                 105                 110 ttc acc tat ggc gtc ctc atg gac tgc tgc tgc cgc gct tgc cgc aca    384
Phe Thr Tyr Gly Val Leu Met Asp Cys Cys Cys Arg Ala Cys Arg Thr
        115                 120                 125 gat ctg gtg ctc gcc ttc ttt ggc cgt ctc ctc aag acg ggc ctg gag    432
Asp Leu Val Leu Ala Phe Phe Gly Arg Leu Leu Lys Thr Gly Leu Glu
130                 135                 140 gca aac caa gtc gtc ttc aac acc ctc ctc aag ggc ctt tgc cac aca    480
Ala Asn Gln Val Val Phe Asn Thr Leu Leu Lys Gly Leu Cys His Thr
145                 150                 155                 160 aag cgg gcg gat gag gct ctg gac gtg ctg ctt cac agg atg cct gag    528
Lys Arg Ala Asp Glu Ala Leu Asp Val Leu Leu His Arg Met Pro Glu
                165                 170                 175 ctg ggc tgc act cct aat gtg gtg gcg tat aac acc gtt atc cat ggc    576
Leu Gly Cys Thr Pro Asn Val Val Ala Tyr Asn Thr Val Ile His Gly
            180                 185                 190 ttc ttt aag gaa ggc cat gta agc aag gcc tgc aat ctg ttc cat gaa    624
Phe Phe Lys Glu Gly His Val Ser Lys Ala Cys Asn Leu Phe His Glu
        195                 200                 205 atg gcg cag cag ggc gtt aag cct aat gtg gtg aca tat aac tca gtt    672
Met Ala Gln Gln Gly Val Lys Pro Asn Val Val Thr Tyr Asn Ser Val
210                 215                 220 att gat gcg ctg tgc aag gcc aga gcc atg gac aag gca gag gtg gtc    720
Ile Asp Ala Leu Cys Lys Ala Arg Ala Met Asp Lys Ala Glu Val Val
225                 230                 235                 240 ctt cgt cag atg att gat gat ggt gtt gga cct gat aat gtg acg tat    768
Leu Arg Gln Met Ile Asp Asp Gly Val Gly Pro Asp Asn Val Thr Tyr
                245                 250                 255
```

-continued

| | | |
|---|---|---|
| agt agc ctc atc cat gga tat tcc tct tca ggc cac tgg aag gag gca<br>Ser Ser Leu Ile His Gly Tyr Ser Ser Ser Gly His Trp Lys Glu Ala<br>260                            265                       270 | 816 |
| gtt agg gta ttc aaa gag atg aca agt cgg agg gtt aca gca gat gtg<br>Val Arg Val Phe Lys Glu Met Thr Ser Arg Arg Val Thr Ala Asp Val<br>275                       280                       285 | 864 |
| cat act tac aac atg ttt atg acc ttt ctt tgc aaa cat gga aga agc<br>His Thr Tyr Asn Met Phe Met Thr Phe Leu Cys Lys His Gly Arg Ser<br>290                           295                      300 | 912 |
| aaa gaa gct gca gga att ttt gat acc atg gct atc aag ggc ctg aaa<br>Lys Glu Ala Ala Gly Ile Phe Asp Thr Met Ala Ile Lys Gly Leu Lys<br>305                         310                      315              320 | 960 |
| cct gac aac gtt tca tat gct att cgc ctt cat ggg tat gcc acc gaa<br>Pro Asp Asn Val Ser Tyr Ala Ile Arg Leu His Gly Tyr Ala Thr Glu<br>                   325                      330                      335 | 1008 |
| gga tgc cta gtt gac atg atc aat ctc ttc aat tcc atg gca aca cac<br>Gly Cys Leu Val Asp Met Ile Asn Leu Phe Asn Ser Met Ala Thr His<br>                   340                      345                      350 | 1056 |
| tgc att cta cct aac tgt cat ata ttc aac ata ctg att aat gca tat<br>Cys Ile Leu Pro Asn Cys His Ile Phe Asn Ile Leu Ile Asn Ala Tyr<br>          355                      360                      365 | 1104 |
| gct aaa tct ggg aag ctt gat aag gct atg ctt atc ttc aat gaa atg<br>Ala Lys Ser Gly Lys Leu Asp Lys Ala Met Leu Ile Phe Asn Glu Met<br>370                         375                      380 | 1152 |
| cag aaa caa gga gtg agt cca aat gca gtc aca tat tca acc gta ata<br>Gln Lys Gln Gly Val Ser Pro Asn Ala Val Thr Tyr Ser Thr Val Ile<br>385                         390                      395              400 | 1200 |
| cat gca ttt tgc aag aag ggt agg ttg gat gat gct gtg ata aag ttt<br>His Ala Phe Cys Lys Lys Gly Arg Leu Asp Asp Ala Val Ile Lys Phe<br>                   405                      410                      415 | 1248 |
| aat cag atg att gat aca gga gta cga ccg gac gca tct gtt tat cgt<br>Asn Gln Met Ile Asp Thr Gly Val Arg Pro Asp Ala Ser Val Tyr Arg<br>                   420                      425                      430 | 1296 |
| ccc cta atc cag ggt ttt tgt aca cat ggc gat ttg gtg aaa gca aag<br>Pro Leu Ile Gln Gly Phe Cys Thr His Gly Asp Leu Val Lys Ala Lys<br>                   435                      440                      445 | 1344 |
| gaa tat gtt act gaa atg atg aag aaa ggt atg cct cct cct gat att<br>Glu Tyr Val Thr Glu Met Met Lys Lys Gly Met Pro Pro Pro Asp Ile<br>450                         455                      460 | 1392 |
| atg ttc ttc agt tca atc atg cag aac cta tgc aca gaa gga agg gta<br>Met Phe Phe Ser Ser Ile Met Gln Asn Leu Cys Thr Glu Gly Arg Val<br>465                         470                      475              480 | 1440 |
| aca gaa gca cgg gat atc ctt gac ttg ata gtg cac att ggt atg agg<br>Thr Glu Ala Arg Asp Ile Leu Asp Leu Ile Val His Ile Gly Met Arg<br>                   485                      490                      495 | 1488 |
| cct aat gtt atc ata ttt aat ttg ctg atc ggt gga tac tgc cta gtc<br>Pro Asn Val Ile Ile Phe Asn Leu Leu Ile Gly Gly Tyr Cys Leu Val<br>                   500                      505                      510 | 1536 |
| cgc aag atg gca gat gca ttg aaa gta ttt gat gat atg gtg tca tat<br>Arg Lys Met Ala Asp Ala Leu Lys Val Phe Asp Asp Met Val Ser Tyr<br>                   515                      520                      525 | 1584 |
| ggt tta gaa cct tgt aac ttt acg tat ggt ata ctt att aat ggc tat<br>Gly Leu Glu Pro Cys Asn Phe Thr Tyr Gly Ile Leu Ile Asn Gly Tyr<br>530                         535                      540 | 1632 |
| tgc aaa aat aga agg att gat gac ggg ctt att ctg ttc aaa gag atg<br>Cys Lys Asn Arg Arg Ile Asp Asp Gly Leu Ile Leu Phe Lys Glu Met<br>545                         550                      555              560 | 1680 |
| ctg cac aag gga ctt aaa cct aca act ttt aat tat aac gtc ata ctg<br>Leu His Lys Gly Leu Lys Pro Thr Thr Phe Asn Tyr Asn Val Ile Leu<br>                   565                      570                      575 | 1728 |

|  |  |
|---|---|
| gat gga tta ttt ctg gct gga caa act gtt gct gca aaa gag aag ttt<br>Asp Gly Leu Phe Leu Ala Gly Gln Thr Val Ala Ala Lys Glu Lys Phe<br>        580                        585                      590 | 1776 |
| gat gag atg gtt gaa tct gga gta agt gtg tgc att gat aca tac tct<br>Asp Glu Met Val Glu Ser Gly Val Ser Val Cys Ile Asp Thr Tyr Ser<br>    595                        600                        605 | 1824 |
| ata att ctt ggt gga ctt tgt aga aat agc tgc agt agc gaa gcg atc<br>Ile Ile Leu Gly Gly Leu Cys Arg Asn Ser Cys Ser Ser Glu Ala Ile<br>        610                        615                        620 | 1872 |
| acc ctt ttc cgg aaa tta agc gca atg aat gtg aaa ttt gat att aca<br>Thr Leu Phe Arg Lys Leu Ser Ala Met Asn Val Lys Phe Asp Ile Thr<br>625                        630                        635                        640 | 1920 |
| att gtc aat atc att att ggt gcc tta tac agg gtc gag aga aac caa<br>Ile Val Asn Ile Ile Ile Gly Ala Leu Tyr Arg Val Glu Arg Asn Gln<br>                        645                        650                        655 | 1968 |
| gag gct aag gat ttg ttt gct gct atg cca gcc aat ggc ttg gtt cct<br>Glu Ala Lys Asp Leu Phe Ala Ala Met Pro Ala Asn Gly Leu Val Pro<br>        660                        665                        670 | 2016 |
| aat gct gtt acc tac acc gta atg atg aca aat ctt ata aaa gaa ggt<br>Asn Ala Val Thr Tyr Thr Val Met Met Thr Asn Leu Ile Lys Glu Gly<br>            675                        680                        685 | 2064 |
| tca gtg gaa gaa gct gac aat ctt ttc tta tcc atg gag aag agc ggc<br>Ser Val Glu Glu Ala Asp Asn Leu Phe Leu Ser Met Glu Lys Ser Gly<br>    690                        695                        700 | 2112 |
| tgt act gcc aac tct tgc ctg tta aat cat atc atc aga agg tta ctg<br>Cys Thr Ala Asn Ser Cys Leu Leu Asn His Ile Ile Arg Arg Leu Leu<br>705                        710                        715                        720 | 2160 |
| gaa aaa gga gag ata gtc aag gct gga aat tat atg tct aaa gtt gat<br>Glu Lys Gly Glu Ile Val Lys Ala Gly Asn Tyr Met Ser Lys Val Asp<br>                        725                        730                        735 | 2208 |
| gca aag agc tac tca ctt gaa gct aaa act gtt tcg ctg ctg atc tct<br>Ala Lys Ser Tyr Ser Leu Glu Ala Lys Thr Val Ser Leu Leu Ile Ser<br>        740                        745                        750 | 2256 |
| ctg ttt tca agg aaa ggg aaa tat aga gaa cac atc aaa ttg ctt cct<br>Leu Phe Ser Arg Lys Gly Lys Tyr Arg Glu His Ile Lys Leu Leu Pro<br>            755                        760                        765 | 2304 |
| aca aag tat cag ttt ctg gaa gaa gca gcc aca gtt gaa tag<br>Thr Lys Tyr Gln Phe Leu Glu Glu Ala Ala Thr Val Glu<br>770                        775                        780 | 2346 |

<210> SEQ ID NO 17
<211> LENGTH: 781
<212> TYPE: PRT
<213> ORGANISM: Triticum aestivum

<400> SEQUENCE: 17

Met Ser Pro Pro Arg Leu Arg Leu Arg Leu Cys Ala Arg His
1               5                      10                   15

Ser Ser Ser Thr Ser His Pro Ser Arg Ile Trp Asp Pro His Ala Ala
              20                      25                      30

Phe Ala Ala Ala Ala Gln Arg Ala Ser Ser Gly Thr Leu Thr Thr Glu
        35                      40                      45

Asp Ala His His Leu Phe Asp Glu Leu Leu Arg Arg Gly Asn Pro Val
    50                      55                      60

Gln Glu Arg Pro Leu Asn Lys Phe Leu Ala Ala Leu Ala Arg Ala Pro
65                      70                      75                      80

Ala Ser Ala Ser Cys Cys Asp Gly Pro Ala Leu Ala Val Thr Leu Phe
              85                      90                      95

-continued

Gly Arg Leu Ser Arg Asp Val Gly Arg Val Ala Gln Pro Asn Val
            100                 105                 110

Phe Thr Tyr Gly Val Leu Met Asp Cys Cys Arg Ala Cys Arg Thr
            115                 120                 125

Asp Leu Val Leu Ala Phe Phe Gly Arg Leu Leu Lys Thr Gly Leu Glu
130                 135                 140

Ala Asn Gln Val Val Phe Asn Thr Leu Leu Lys Gly Leu Cys His Thr
145                 150                 155                 160

Lys Arg Ala Asp Glu Ala Leu Asp Val Leu Leu His Arg Met Pro Glu
            165                 170                 175

Leu Gly Cys Thr Pro Asn Val Val Ala Tyr Asn Thr Val Ile His Gly
            180                 185                 190

Phe Phe Lys Glu Gly His Val Ser Lys Ala Cys Asn Leu Phe His Glu
            195                 200                 205

Met Ala Gln Gln Gly Val Lys Pro Asn Val Val Thr Tyr Asn Ser Val
            210                 215                 220

Ile Asp Ala Leu Cys Lys Ala Arg Ala Met Asp Lys Ala Glu Val Val
225                 230                 235                 240

Leu Arg Gln Met Ile Asp Asp Gly Val Gly Pro Asp Asn Val Thr Tyr
            245                 250                 255

Ser Ser Leu Ile His Gly Tyr Ser Ser Gly His Trp Lys Glu Ala
            260                 265                 270

Val Arg Val Phe Lys Glu Met Thr Ser Arg Arg Val Thr Ala Asp Val
            275                 280                 285

His Thr Tyr Asn Met Phe Met Thr Phe Leu Cys Lys His Gly Arg Ser
            290                 295                 300

Lys Glu Ala Ala Gly Ile Phe Asp Thr Met Ala Ile Lys Gly Leu Lys
305                 310                 315                 320

Pro Asp Asn Val Ser Tyr Ala Ile Arg Leu His Gly Tyr Ala Thr Glu
            325                 330                 335

Gly Cys Leu Val Asp Met Ile Asn Leu Phe Asn Ser Met Ala Thr His
            340                 345                 350

Cys Ile Leu Pro Asn Cys His Ile Phe Asn Ile Leu Ile Asn Ala Tyr
            355                 360                 365

Ala Lys Ser Gly Lys Leu Asp Lys Ala Met Leu Ile Phe Asn Glu Met
370                 375                 380

Gln Lys Gln Gly Val Ser Pro Asn Ala Val Thr Tyr Ser Thr Val Ile
385                 390                 395                 400

His Ala Phe Cys Lys Lys Gly Arg Leu Asp Asp Ala Val Ile Lys Phe
            405                 410                 415

Asn Gln Met Ile Asp Thr Gly Val Arg Pro Asp Ala Ser Val Tyr Arg
            420                 425                 430

Pro Leu Ile Gln Gly Phe Cys Thr His Gly Asp Leu Val Lys Ala Lys
            435                 440                 445

Glu Tyr Val Thr Glu Met Met Lys Lys Gly Met Pro Pro Asp Ile
450                 455                 460

Met Phe Phe Ser Ser Ile Met Gln Asn Leu Cys Thr Glu Gly Arg Val
465                 470                 475                 480

Thr Glu Ala Arg Asp Ile Leu Asp Leu Ile Val His Ile Gly Met Arg
            485                 490                 495

Pro Asn Val Ile Ile Phe Asn Leu Leu Ile Gly Gly Tyr Cys Leu Val
            500                 505                 510

Arg Lys Met Ala Asp Ala Leu Lys Val Phe Asp Asp Met Val Ser Tyr

```
        515                 520                 525
Gly Leu Glu Pro Cys Asn Phe Thr Tyr Gly Ile Leu Ile Asn Gly Tyr
    530                 535                 540

Cys Lys Asn Arg Arg Ile Asp Asp Gly Leu Ile Leu Phe Lys Glu Met
545                 550                 555                 560

Leu His Lys Gly Leu Lys Pro Thr Thr Phe Asn Tyr Asn Val Ile Leu
                565                 570                 575

Asp Gly Leu Phe Leu Ala Gly Gln Thr Val Ala Ala Lys Glu Lys Phe
            580                 585                 590

Asp Glu Met Val Glu Ser Gly Val Ser Val Cys Ile Asp Thr Tyr Ser
        595                 600                 605

Ile Ile Leu Gly Gly Leu Cys Arg Asn Ser Cys Ser Ser Glu Ala Ile
    610                 615                 620

Thr Leu Phe Arg Lys Leu Ser Ala Met Asn Val Lys Phe Asp Ile Thr
625                 630                 635                 640

Ile Val Asn Ile Ile Gly Ala Leu Tyr Arg Val Glu Arg Asn Gln
                645                 650                 655

Glu Ala Lys Asp Leu Phe Ala Ala Met Pro Ala Asn Gly Leu Val Pro
            660                 665                 670

Asn Ala Val Thr Tyr Thr Val Met Met Thr Asn Leu Ile Lys Glu Gly
        675                 680                 685

Ser Val Glu Glu Ala Asp Asn Leu Phe Leu Ser Met Glu Lys Ser Gly
    690                 695                 700

Cys Thr Ala Asn Ser Cys Leu Leu Asn His Ile Ile Arg Arg Leu Leu
705                 710                 715                 720

Glu Lys Gly Glu Ile Val Lys Ala Gly Asn Tyr Met Ser Lys Val Asp
                725                 730                 735

Ala Lys Ser Tyr Ser Leu Glu Ala Lys Thr Val Ser Leu Leu Ile Ser
            740                 745                 750

Leu Phe Ser Arg Lys Gly Lys Tyr Arg Glu His Ile Lys Leu Leu Pro
        755                 760                 765

Thr Lys Tyr Gln Phe Leu Glu Glu Ala Ala Thr Val Glu
    770                 775                 780

<210> SEQ ID NO 18
<211> LENGTH: 3438
<212> TYPE: DNA
<213> ORGANISM: Triticum aestivum

<400> SEQUENCE: 18
caacttggaa aagcacagcc ccgtcgtcct gctcccagtt gagttcgcga cctacacacc      60
ggccatgccc cgcttctcct ccaccacgcc aatgtcgcca cccgcctcc gcctccgcct     120 ccgactctgc gcccgccact cctcctccac ctctcatccc tcacgcatct gggatcccca     180
cgccgccttc gccgccgcgg cacagcgggc gagctctggc acgctcacta cggaggacgc     240
acaccacctg tttgacgaat tgctgcggcg gggcaatcct gtccaggagc gtcccttgaa     300
taaatttctg gctgccctcg cccgcgcgcc cgcgtccgca tcctgctgcg atggccccgc     360
cctggcagtc accctcttcg gccgtttgtc ccgagacgtc ggacgacggg tggcgcagcc     420
aaatgtcttc acctatggcg tcctcatgga ctgctgctgc gcgcttgcc gcacagatct     480 ggtgctcgcc ttctttggcc gtctcctcaa gacgggcctg gagcaaacc aagtcgtctt     540 caacaccctc tcaagggcc tttgccacac aaagcgggcg gatgaggctc tggacgtgct     600
gcttcacagg atgcctgagc tgggctgcac tcctaatgtg gtggcgtata acaccgttat     660
```

-continued

```
ccatggcttc tttaaggaag gccatgtaag caaggcctgc aatctgttcc atgaaatggc    720
gcagcagggc gttaagccta atgtggtgac atataactca gttattgatg cgctgtgcaa    780
ggccagagcc atggacaagg cagaggtggt ccttcgtcag atgattgatg atggtgttgg    840
acctgataat gtgacgtata gtagcctcat ccatggatat tcctcttcag gccactggaa    900
ggaggcagtt agggtattca aagagatgac aagtcggagg gttacagcag atgtgcatac    960
ttacaacatg tttatgacct ttcttttgcaa acatggaaga agcaaagaag ctgcaggaat   1020
ttttgatacc atggctatca agggcctgaa acctgacaac gtttcatatg ctattcgcct   1080
tcatgggtat gccaccgaag gatgcctagt tgacatgatc aatctcttca attccatggc   1140
aacacactgc attctaccta actgtcatat attcaacata ctgattaatg catatgctaa   1200
atctggaaag cttgataagg ctatgcttat cttcaatgaa atgcagaaac aaggagtgag   1260
tccaaatgca gtcacatatt caaccgtaat acatgcattt tgcaagaagg gtaggttgga   1320
tgatgctgtg ataaagttta atcagatgat tgatacagga gtacgaccgg acgcatctgt   1380
ttatcgtccc ctaatccagg gttttttgtac acatggcgat ttggtgaaag caaaggaata   1440
tgttactgaa atgatgaaga aaggtatgcc tcctcctgat attatgttct tcagttcaat   1500
catgcagaac ctatgcacag aaggaagggt aacagaagca cgggatatcc ttgacttgat   1560
agtgcacatt ggtatgaggc ctaatgttat catatttaat ttgctgatcg gtggatactg   1620
cctagtccgc aagatggcag atgcattgaa agtatttgat gatatggtgt catatggttt   1680
agaaccttgt aactttacgt atggtatact tattaatggc tattgcaaaa atagaaggat   1740
tgatgacggg cttattctgt tcaaagagat gctgcacaag ggacttaaac ctacaacttt   1800
taattataac gtcatactgg atggattatt tctggctgga caaactgttg ctgcaaaaga   1860
gaagtttgat gagatggttg aatctggagt aagtgtgtgc attgatacat actctataat   1920
tcttggtgga ctttgtagaa atagctgcag tagcgaagcg atcacccttt tccggaaatt   1980
aagcgcaatg aatgtgaaat tgatattac aattgtcaat atcattattg gtgccttata   2040
cagggtcgag agaaaccaag aggctaagga tttgtttgct gctatgccag ccaatggctt   2100
ggttcctaat gctgttacct acaccgtaat gatgacaaat cttataaaag aaggttcagt   2160
ggaagaagct gacaatcttt tcttatccat ggagaagagc ggctgtactg ccaactcttg   2220
cctgttaaat catatcatca gaaggttact ggaaaaagga gagatagtca aggctggaaa   2280
ttatatgtct aaagttgatg caaagagcta ctcacttgaa gctaaaactg tttcgctgct   2340
gatctctctg ttttcaagga aagggaaata tagagaacac atcaaattgc ttcctacaaa   2400
gtatcagttt ctggaagaag cagccacagt tgaatagttg gtacatgata tctgaaattt   2460
aatttgcatc gcttgccatg ggtccgtctg cttgtacaag aaatgcattt tctatttgta   2520
aataggaagt cagtttagaa caagccatca ggatgacgca aagagtacaa ttcagttgca   2580
ccaccaataa aaaggcagaa ctagggctgc aaaacaaca ctgaatcaaa actcaaacag    2640
aaggagcagc aaactttttt ttttgaagct ggacagtctg ctagccaaac aactacagga   2700
gactgtcagg cggggcatgt agtggctggc gtctaagcgc cttggcttct tccaccatcc   2760
atggcttagc ctcacacgga atcgagtcaa ccaattcccg tcggttttgg gtggctccct   2820
tgaagatgca attgttttca gcggccagat acgcatggtc agattaatca gcgagtgtgc   2880
cccttctgtc tggttcgaga aagaatttga agagctgagc ttgtcccagc tggaaccagt   2940
ttgaggttag ttaatcataa cagggtacta gagaggtgtt ttattgactg ttgatgtgta   3000
```

| | |
|---|---|
| atatgttata tgccatcctc ttgatgatta cggtgatctg tgaagaggca gcatgcaaaa | 3060 |
| gtctgaatca catatgctta tgtaattgtg ttattatttg tgcagcttct agaccttttg | 3120 |
| ccttgtagat ggctacatgg atctagttgt agcaatctgt aactgttagt gttttgtata | 3180 |
| tgctggcatt tgatgattagg gtgacttgtg aagcatgcag aagtctgaat catacatgct | 3240 |
| tgtctagtta tttttggggc tctctctttg ccatgtacat gttttatgga tgcagttgta | 3300 |
| gtctgtatgt gctggcattt aatatgaggg ctggtctgca attttctgt tttgatcgat | 3360 |
| acagcgccat gttgagttta accctgtaac ttggcttaac tagatcatgc tggtgttatc | 3420 |
| tctaggaatc acaatatc | 3438 |

<210> SEQ ID NO 19
<211> LENGTH: 2373
<212> TYPE: DNA
<213> ORGANISM: Triticum aestivum

<400> SEQUENCE: 19

| | |
|---|---|
| atgccccgct tctcctccac cacgccaatg tcgccacccc gcctccgcct ccgcctccga | 60 |
| ctctgcgccc gccactcctc ctccacctct catccctcac gcatctggga tccccacgcc | 120 |
| gccttcgccg ccgcggcaca gcgggcgagc tctggcacgc tcactacgga ggacgcacac | 180 |
| cacctgtttg acgaattgct gcggcggggc aatcctgtcc aggagcgtcc cttgaataaa | 240 |
| tttctggctg ccctcgcccg cgcgcccgcg tccgcatcct gctgcgatgg ccccgccctg | 300 |
| gcagtcaccc tcttcggccg tttgtcccga cgtcggac gacgggtggc gcagccaaat | 360 |
| gtcttcacct atgcgtcct catggactgc tgctgccgcg cttgccgcac agatctggtg | 420 |
| ctcgccttct ttggccgtct cctcaagacg ggcctggagg caaaccaagt cgtcttcaac | 480 |
| accctcctca agggcctttg ccacacaaag cgggcggatg aggctctgga cgtgctgctt | 540 |
| cacaggatgc ctgagctggg ctgcactcct aatgtggtgg cgtataacac cgttatccat | 600 |
| ggcttcttta aggaaggcca tgtaagcaag gcctgcaatc tgttccatga aatgcgcag | 660 |
| cagggcgtta agcctaatgt ggtgacatat aactcagtta ttgatgcgct gtgcaaggcc | 720 |
| agagccatgg acaaggcaga ggtggtcctt cgtcagatga ttgatgatgg tgttggacct | 780 |
| gataatgtga cgtatagtag cctcatccat ggatattcct cttcaggcca ctggaaggag | 840 |
| gcagttaggg tattcaaaga gatgacaagt cggagggtta cagcagatgt gcatacttac | 900 |
| aacatgttta tgacctttct ttgcaaacat ggaagaagca agaagctgc aggaattttt | 960 |
| gataccatgg ctatcaaggg cctgaaacct gacaacgttt catatgctat tcgccttcat | 1020 |
| gggtatgcca ccgaaggatg cctagttgac atgatcaatc tcttcaattc catggcaaca | 1080 |
| cactgcattc tacctaactg tcatatattc aacatactga ttaatgcata tgctaaatct | 1140 |
| gggaagcttg ataaggctat gcttatcttc aatgaaatgc agaaacaagg agtgagtcca | 1200 |
| aatgcagtca catattcaac cgtaatacat gcattttgca agaagggtag gttggatgat | 1260 |
| gctgtgataa agtttaatca gatgattgat acaggagtac gaccggacgc atctgtttat | 1320 |
| cgtcccctaa tccagggttt ttgtacacat ggcgatttgg tgaaagcaaa ggaatatgtt | 1380 |
| actgaaatga tgaagaaagg tatgcctcct cctgatatta tgttcttcag ttcaatcatg | 1440 |
| cagaacctat gcacagaagg aagggtaaca gaagcacggg atatccttga cttgatagtg | 1500 |
| cacattggta tgaggcctaa tgttatcata tttaatttgc tgatcggtgg atactgccta | 1560 |
| gtccgcaaga tggcagatgc attgaaagta tttgatgata tggtgtcata tggtttagaa | 1620 |
| ccttgtaact ttacgtatgg tatacttatt aatggctatt gcaaaaatag aaggattgat | 1680 |

```
gacgggctta ttctgttcaa agagatgctg cacaagggac ttaaacctac aactttaat     1740 tataacgtca tactggatgg attatttctg gctggacaaa ctgttgctgc aaaagagaag    1800
tttgatgaga tggttgaatc tggagtaagt gtgtgcattg atacatactc tataattctt   1860
ggtggacttt gtagaaatag ctgcagtagc gaagcgatca ccctttccg gaaattaagc    1920 gcaatgaatg tgaaatttga tattacaatt gtcaatatca ttattggtgc cttatacagg   1980
gtcgagagaa accaagaggc taaggatttg tttgctgcta tgccagccaa tggcttggtt   2040
cctaatgctg ttacctacac cgtaatgatg acaaatctta taaagaagg ttcagtggaa    2100 gaagctgaca tcttttctt atccatggag aagagcggct gtactgccaa ctcttgcctg    2160
ttaaatcata tcatcagaag gttactggaa aaggagaga tagtcaaggc tggaaattat    2220
atgtctaaag ttgatgcaaa gagctactca cttgaagcta aaactgttc gctgctgatc    2280 tctctgtttt caaggaaagg gaaatataga gaacacatca aattgcttcc tacaaagtat   2340
cagtttctgg aagaagcagc cacagttgaa tag                                 2373
```

```
<210> SEQ ID NO 20
<211> LENGTH: 790
<212> TYPE: PRT
<213> ORGANISM: Triticum aestivum

<400> SEQUENCE: 20

Met Pro Arg Phe Ser Ser Thr Thr Pro Met Ser Pro Pro Arg Leu Arg
1               5                   10                  15

Leu Arg Leu Arg Leu Cys Ala Arg His Ser Ser Thr Ser His Pro
            20                  25                  30

Ser Arg Ile Trp Asp Pro His Ala Ala Phe Ala Ala Ala Gln Arg
        35                  40                  45

Ala Ser Ser Gly Thr Leu Thr Thr Glu Asp Ala His His Leu Phe Asp
    50                  55                  60

Glu Leu Leu Arg Arg Gly Asn Pro Val Gln Glu Arg Pro Leu Asn Lys
65                  70                  75                  80

Phe Leu Ala Ala Leu Ala Arg Ala Pro Ala Ser Ala Ser Cys Cys Asp
                85                  90                  95

Gly Pro Ala Leu Ala Val Thr Leu Phe Gly Arg Leu Ser Arg Asp Val
            100                 105                 110

Gly Arg Arg Val Ala Gln Pro Asn Val Phe Thr Tyr Gly Val Leu Met
        115                 120                 125

Asp Cys Cys Cys Arg Ala Cys Arg Thr Asp Leu Val Leu Ala Phe Phe
    130                 135                 140

Gly Arg Leu Leu Lys Thr Gly Leu Glu Ala Asn Gln Val Val Phe Asn
145                 150                 155                 160

Thr Leu Leu Lys Gly Leu Cys His Thr Lys Arg Ala Asp Glu Ala Leu
                165                 170                 175

Asp Val Leu Leu His Arg Met Pro Glu Leu Gly Cys Thr Pro Asn Val
            180                 185                 190

Val Ala Tyr Asn Thr Val Ile His Gly Phe Phe Lys Glu Gly His Val
        195                 200                 205

Ser Lys Ala Cys Asn Leu Phe His Glu Met Ala Gln Gln Gly Val Lys
    210                 215                 220

Pro Asn Val Val Thr Tyr Asn Ser Val Ile Asp Ala Leu Cys Lys Ala
225                 230                 235                 240

Arg Ala Met Asp Lys Ala Glu Val Val Leu Arg Gln Met Ile Asp Asp
```

```
                245                 250                 255
Gly Val Gly Pro Asp Asn Val Thr Tyr Ser Ser Leu Ile His Gly Tyr
            260                 265                 270

Ser Ser Ser Gly His Trp Lys Glu Ala Val Arg Val Phe Lys Glu Met
            275                 280                 285

Thr Ser Arg Arg Val Thr Ala Asp Val His Thr Tyr Asn Met Phe Met
            290                 295                 300

Thr Phe Leu Cys Lys His Gly Arg Ser Lys Glu Ala Ala Gly Ile Phe
305                 310                 315                 320

Asp Thr Met Ala Ile Lys Gly Leu Lys Pro Asp Asn Val Ser Tyr Ala
                325                 330                 335

Ile Arg Leu His Gly Tyr Ala Thr Glu Gly Cys Leu Val Asp Met Ile
                340                 345                 350

Asn Leu Phe Asn Ser Met Ala Thr His Cys Ile Leu Pro Asn Cys His
                355                 360                 365

Ile Phe Asn Ile Leu Ile Asn Ala Tyr Ala Lys Ser Gly Lys Leu Asp
                370                 375                 380

Lys Ala Met Leu Ile Phe Asn Glu Met Gln Lys Gln Gly Val Ser Pro
385                 390                 395                 400

Asn Ala Val Thr Tyr Ser Thr Val Ile His Ala Phe Cys Lys Lys Gly
                405                 410                 415

Arg Leu Asp Asp Ala Val Ile Lys Phe Asn Gln Met Ile Asp Thr Gly
                420                 425                 430

Val Arg Pro Asp Ala Ser Val Tyr Arg Pro Leu Ile Gln Gly Phe Cys
                435                 440                 445

Thr His Gly Asp Leu Val Lys Ala Lys Glu Tyr Val Thr Glu Met Met
                450                 455                 460

Lys Lys Gly Met Pro Pro Asp Ile Met Phe Phe Ser Ser Ile Met
465                 470                 475                 480

Gln Asn Leu Cys Thr Glu Gly Arg Val Thr Glu Ala Arg Asp Ile Leu
                485                 490                 495

Asp Leu Ile Val His Ile Gly Met Arg Pro Asn Val Ile Ile Phe Asn
                500                 505                 510

Leu Leu Ile Gly Gly Tyr Cys Leu Val Arg Lys Met Ala Asp Ala Leu
                515                 520                 525

Lys Val Phe Asp Asp Met Val Ser Tyr Gly Leu Glu Pro Cys Asn Phe
                530                 535                 540

Thr Tyr Gly Ile Leu Ile Asn Gly Tyr Cys Lys Asn Arg Arg Ile Asp
545                 550                 555                 560

Asp Gly Leu Ile Leu Phe Lys Glu Met Leu His Lys Gly Leu Lys Pro
                565                 570                 575

Thr Thr Phe Asn Tyr Asn Val Ile Leu Asp Gly Leu Phe Leu Ala Gly
                580                 585                 590

Gln Thr Val Ala Ala Lys Glu Lys Phe Asp Glu Met Val Glu Ser Gly
                595                 600                 605

Val Ser Val Cys Ile Asp Thr Tyr Ser Ile Ile Leu Gly Gly Leu Cys
                610                 615                 620

Arg Asn Ser Cys Ser Ser Glu Ala Ile Thr Leu Phe Arg Lys Leu Ser
625                 630                 635                 640

Ala Met Asn Val Lys Phe Asp Ile Thr Ile Val Asn Ile Ile Ile Gly
                645                 650                 655

Ala Leu Tyr Arg Val Glu Arg Asn Gln Glu Ala Lys Asp Leu Phe Ala
                660                 665                 670
```

```
Ala Met Pro Ala Asn Gly Leu Val Pro Asn Ala Val Thr Tyr Thr Val
        675                 680                 685

Met Met Thr Asn Leu Ile Lys Glu Gly Ser Val Glu Glu Ala Asp Asn
        690                 695                 700

Leu Phe Leu Ser Met Glu Lys Ser Gly Cys Thr Ala Asn Ser Cys Leu
705                 710                 715                 720

Leu Asn His Ile Ile Arg Arg Leu Leu Glu Lys Gly Glu Ile Val Lys
                725                 730                 735

Ala Gly Asn Tyr Met Ser Lys Val Asp Ala Lys Ser Tyr Ser Leu Glu
            740                 745                 750

Ala Lys Thr Val Ser Leu Leu Ile Ser Leu Phe Ser Arg Lys Gly Lys
        755                 760                 765

Tyr Arg Glu His Ile Lys Leu Leu Pro Thr Lys Tyr Gln Phe Leu Glu
        770                 775                 780

Glu Ala Ala Thr Val Glu
785                 790

<210> SEQ ID NO 21
<211> LENGTH: 11981
<212> TYPE: DNA
<213> ORGANISM: Triticum aestivum

<400> SEQUENCE: 21
gccgtacgtt cggtgcttgg atcggtcgga tcgtgaagac gtacgactac atcaaccgcg      60
ttgtcagaac gcttccgctt acggtctacg agggtacgtg gacgaacact ctcccctctc     120
gttgctatgc catcaccatg atcttgcgtg tgcgtaggaa attttttgaa attactacgt     180
tccccaacaa ggttgtgctc aggcggagct tcatgcccgc caaccgcagg agatcgccag     240
acatggccgg tgaacactgg gtcccgatcg ctgacgatcg aagagggggaa cccgtggagg     300 cggacgatac cgtcgaagaa ggcacgggcc acagatgcag cagtgtaagg atgaccgagc     360
gtgatgaagt gagcatactt ggagaaatta gtacaaggcc ttcagaaatt cctccataat     420
tttgtacatt ttctgttaaa atttgtagat ccacatgcgt aagtactgga cacgcttcct     480
caagaagaag aatgacatag tctcctgtga tgacgctgag gccatcgccg tattcaaatc     540
cggcgtaacc gacgtgtgat actctggggg atttgatgat aaccccccag ttcatgtcac     600
tttgatcata accccccctt tgtgtcactg acatgtgggg tctggtccca catgtcagtg     660
acacaaaggg ggggggggt tatgatcaaa gtgacgtgaa ctggggggt tatcatcaat     720 tattccgtga tactctccag ggacttcgga tacttcaagc ccaggaccat gccggccttg     780
atggagatgt ggcgcgtagt tcgcagtata tgtgggaaga cactctggat ctacaaaatt     840
ttaatagaaa atgtattcat ttgatagccg cacacaaaaa aaaggcaaaa tcatttgcca     900
ttttctcttc tgtaccgctc atggttcaaa agagttttcc tgaattttgt aaattcatag     960
tgtattcttg cacttcgatg tgagatcccc cccccccccc cccccccccc cccccccct    1020 gaaattttg aaaactaata aatgcctttt gcatatactt ttttccaaat aaaaggatgg    1080
cttgagcttc agagccggat ttttttttttc tcgtgcaata cttaccaaat tcttgttcat    1140
aaaatagtat tcatagacat atatataccc aaatgtgcaa cgtttcttgg ggatctttcc    1200
atgcatgtgt tacgcctgtt tgttcagaga agtatgatt cagaccaaag agaaaccatt    1260
tctggagtgt ttctcgaaga atggttctgc taaattagta ctcctacaag aatttcaggt    1320
ccaagatctt cactgctaag tgagtaaatg aaaaattatg aggaaggaag aagataaaag    1380
```

```
aaaaatactg aacatgggag aaaataaatt ggacagtgaa tataatgaaa taaccaggtt    1440
ctgcttctac aacgcacagc taaaagaaga aaaaaagcac accaattgtt ctatagtaac    1500
aaaatgcacc aaggaacagg ggagaaaacc atggcaaagc tcactgaaat ccatcagact    1560
ctgtctcaaa aaaaggtaat gagatgaatg aaccgatcta ctccctctgt ctcataatgt    1620
aagacgtttt ttggcactag tgtagtgtta aaaaacatct tatattatgg gacggaggga    1680
gtataatttt agggcacact attgttggat agaatagata ataacaatga ccctgtttca    1740
ttaacaaaat agtaccacat atcagtttaa tatatactgc ctgcttactg ttcatactac    1800
caaagccaaa aagaatagag aatttatcac ctctatcgga cggaatagag aagttcaaaa    1860
tgcatcaaac atactatatc cttattatag tcataccggc atgatataca gagtattgaa    1920
taacaaagga acatgctgac agtcgatgaa attatggaca gaaccatatt acctctgaac    1980
attgatatgc cacagagtat gtttaattca acgtttaaaa atgccgaggc ccctgatatt    2040
gatctggtta agccaagtta cagggttaaa ctcaacatgg tgctgaatcg atcaaaacaa    2100
ataatttgga gcccggccct aaattaatca atgccagcat atacaaaaca ctaacagtca    2160
cagtcacaga ctgctacaac gtgatccatg tagccataca aggcagaagg tctagaagct    2220
gcacaaataa taacacaatt acataagcat atgtgattca cagatcaccc tattcatcaa    2280
gtggctggca tataacatag gagtattacc catcaacagt caacaaaaca cctgtctagt    2340
accctgttat gattaactaa cctcaaactg gcttcggcag ggacaagctg gtcaagcacc    2400
tgttgctgct cagcgttttc aaattctttc tcgaaccaga caaaagagac acgctcgctg    2460
attactctga actttggtg tatctggtgg ctgagaaaac atttgcaaca gctacgccga    2520
gaaattggtt gactccattc cctgtgaggc caagccatgg atgctggcag cagaaaaggg    2580
acttacacag gtgccactac atgcccggcc gcctgaatct ctcccgtagg tgttctacta    2640
gcagacatac aacttcaaaa caattgctgg tcctacagtt gaattgtact ctttgcgtca    2700
tcctgatggc ttgttctcaa ctgccttcct atttacatat ggaaattgca cttgttgtac    2760
aagcagataa actcatggca aacaataatt caaccttacc ttctgaggag ttaagttcag    2820
atatcatgta aaaccattca actgtagctc attctccgcg aaactgatac tttgcgggga    2880
gcaatcttat ctgttctctg tatttccctt tccctgaaaa gagagagatc agcagcgaaa    2940
cagttttagc ttcaagtgag tagctctttg catcaacttt agacataagg agggaggaaa    3000
gtgaacctat tccttggcta ttttggttca ccacaaatct actttccact gattcatagt    3060
gcattcttac atgtacaagt gaggtttgtt cgggatgttt gattataact tacaactgta    3120
ctttctgaaa aaaaaagatc aatgaatctc cgaaagccgg aaaaaatctg ctcccagaat    3180
agaccaattt atcatttcaa agagtcccaa cattcagagt acatccatat gctgctacag    3240
ggtgtgctac tccattacag ctgcgattgc aagatctgaa atacagtcat acatattttg    3300
tgctaggtac tccttcagtt cagctatagt gcaaaactga atggaattat gagatgcaaa    3360
tagtactata tgattagaca attatgccca ggcaccagcc aacttatgga atacaagaat    3420
gggttctctt tcagaaaaat agtactggta tgatttcagg tccaagactt tcactggcca    3480
ctgccaagga tgtttaggac gatattgaat tccttctata gcttacacct acatgaccca    3540
ggaaaacagt ttataacatt cttacgatcg cgaaaacaca ctagcgttct ttcgtacgta    3600
ctacaaacca tgttgcttta caaaattcaa aaatcaaaa cccttatttc gggaagaaga    3660
aaaagcatca tacgtataaa aaatgctacc aaaaatattta ctaaattctt tttcaaaaaa    3720
tagtattcat gcatagacat atctaccaaa tgtgcaatgt ttcttgggga tctttccatg    3780
```

```
catgagtcac acctgtttgt tcagagacaa tatgattcag acccaagaca aaccatttt    3840 ggagtgtttc tcgaagaatg gttctactaa attagtacaa gaatttcagg tccaagacct   3900
gtactactca gtgagtaaat gaaaaattac gcggaaggaa caagataaaa taaaatgctg   3960
aacttctgag ctctcgtaag aaaataaatt agacaatgaa ttaatgaaat aaacaggttt   4020
tgttgttcta taacgtacag ccaaaagaaa aaaagcgcac accaattgtt ctatagtaac   4080
aaaatgtacc aaggacgggc gaagctcacc gaaatcccata tgagatgaat gaaccgatct  4140
ataattttat ggaacactat tgctggataa aatagataat aaaaaggacc ctgtttcact   4200
aacaaaatag taccacatat cagtttatta ctgcctgctt tctgttcata ctaccaaagc   4260
caacaagaat agaaatttat cagctttatc ccaagaaaca gagaagctca aaatgcacca   4320
gccgtatatc cttattatag tcataccgcc gtgatataca gagtactaaa taaaaaagga   4380
acatgctgac agtcgatgaa aattacgggc agaaccatat tacctctgga cattgatctg   4440
cgtcagtttg tgcaacaaca gagagtattg atattgtgat tcctagagat aacaccagca   4500
tgatctagtt aagccaagtt acagggttaa actcaacatg gcgctgtatc gatcaaaaca   4560
gaaaaattgc agaccagccc tcatattaaa tgccagcaca tacagactac aactgcatcc   4620
ataaaacatg tacatggcaa agagagagcc ccaaaaataa ctagacaagc atgtatgatt   4680
cagacttctg catgcttcac aagtcaccct aatcatcaat gccagcatat acaaaacact   4740
aacagttaca gattgctaca actagatcca tgtagccatc tacaaggcaa aaggtctaga   4800
agctgcacaa ataataacac aattacataa gcatatgtga ttcagacttt tgcatgctgc   4860
ctcttcacag atcaccgtaa tcatcaagag gatggcatat aacatattac acatcaacag   4920
tcaataaaac acctctctag taccctgtta tgattaacta acctcaaact ggttccagct   4980
gggacaagct cagctcttca aattctttct cgaaccagac agaaggggca cactcgctga   5040
ttaatctgac catgcgtatc tggccgctga aaacaattgc atcttcaagg gagccaccca   5100
aaaccgacgg gaattggttg actcgattcc gtgtgaggct aagccatgga tggtggaaga   5160
agcaaaggcg cttagacgcc agccactaca tgccccgcct gacagtctcc tgtagttgtt   5220
tggctagcag actgtccagc ttcaaaaaaa aaagtttgct gctccttctg tttgagtttt   5280
gattcagtgt tgttttggca gccctagttc tgccttttta ttggtggtgc aactgaattg   5340
tactctttgc gtcatcctga tggcttgttc taaactgact tcctatttac aaatagaaaa   5400
tgcatttctt gtacaagcag acggacccat ggcaagcgat gcaaattaaa tttcagatat   5460
catgtaccaa ctattcaact gtggctgctt cttccagaaa ctgatactt gtaggaagca    5520 atttgatgtg ttctctatat ttcccttttcc ttgaaaacag agagatcagc agcgaaacag   5580
ttttagcttc aagtgagtag ctcttttgcat caactttaga catataattt ccagccttga   5640
ctatctctcc tttttccagt aaccttctga tgatatgatt taacaggcaa gagttggcag   5700
tacagccgct cttctccatg gataagaaaa gattgtcagc ttcttccact gaaccttctt   5760
ttataagatt tgtcatcatt acggtgtagg taacagcatt aggaaccaag ccattggctg   5820
gcatagcagc aaacaaatcc ttagcctctt ggtttctctc gaccctgtat aaggcaccaa   5880
taatgatatt gacaattgta atatcaaatt tcacattcat tgcgcttaat ttccggaaaa   5940
gggtgatcgc ttcgctactg cagctatttc tacaaagtcc accaagaatt atagagtatg   6000
tatcaatgca cacacttact ccagattcaa ccatctcatc aaacttctct tttgcagcaa   6060
cagtttgtcc agccagaaat aatccatcca gtatgacgtt ataattaaaa gttgtaggtt   6120
```

```
taagtccctt gtgcagcatc tctttgaaca gaataagccc gtcatcaatc cttctatttt    6180
tgcaatagcc attaataagt ataccatacg taaagttaca aggttctaaa ccatatgaca    6240
ccatatcatc aaatactttc aatgcatctg ccatcttgcg gactaggcag tatccaccga    6300
tcagcaaatt aaatatgata acattaggcc tcataccaat gtgcactatc aagtcaagga    6360
tatcccgtgc ttctgttacc cttccttctg tgcataggtt ctgcatgatt gaactgaaga    6420
acataatatc aggaggaggc ataccttct tcatcatttc agtaacatat tcctttgctt    6480
tcaccaaatc gccatgtgta caaaaaccct ggattagggg acgataaaca gatgcgtccg    6540
gtcgtactcc tgtatcaatc atctgattaa actttatcac agcatcatcc aacctaccct    6600
tcttgcaaaa tgcatgtatt acggttgaat atgtgactgc atttggactc actccttgtt    6660
tctgcatttc attgaagata agcatagcct tatcaagctt cccagattta gcatatgcat    6720
taatcagtat gttgaatata tgacagttag gtagaatgca gtgtgttgcc atggaattga    6780
agagattgat catgtcaact aggcatcctt cggtggcata cccatgaagg cgaatagcat    6840
atgaaacgtt gtcaggtttc aggcccttga tagccatggc atcaaaaatt cctgcagctt    6900
ctttgcttct tccatgtttg caagaaaagg tcataaacat gttgtaagta tgcacatctg    6960
ctgtaaccct ccgacttgtc atctctttga atacccctaac tgcctccttc cagtggcctg    7020
aagaggaata tccatggatg aggctactat acgtcacatt atcaggtcca acaccatcat    7080
caatcatctg acgaaggacc acctctgcct tgtccatggc tctggccttg cacagcgcat    7140
caataactga gttatatgtc accacattag gcttaacgcc ctgctgcgcc atttcatgga    7200
acagattgca ggccttgctt acatggcctt ccttaaagaa gccatggata acggtgttat    7260
acgccaccac attaggagtg cagcccagct caggcatcct gtgaagcagc acgtccagag    7320
cctcatccgc ccgctttgtg tggcaaaggc ccttgaggag ggtgttgaag acgacttggt    7380
ttgcctccag gcccgtcttg aggagacggc caaagaaggc gagcaccaga tctgtgcggc    7440
aagcgcggca gcagcagtcc atgaggacgc cataggtgaa gacatttggc tgcgccaccc    7500
gtcgtccgac gtctcgggac aaacggccga agagggtgac tgccagggcg gggccatcgc    7560
agcaggatgc ggacgcgggc gcgcgggcga gggcagccag aaatttattc aagggacgct    7620
cctggacagg attgccccgc cgcagcaatt cgtcaaacag gtggtgtgcg tcctccgtag    7680
tgagcgtgcc agagctcgcc cgctgtgccg cggcggcgaa ggcggcgtgg ggatcccaga    7740
tgcgtgaggg atgagaggtg gaggaggagt ggcgggcgca gagtcggagg cggaggcgga    7800
ggcggggtgg cgacattggc gtggtggagg agaagcgggg catggccggt gtgtaggtcg    7860
cgaactcaac tgggagcagg acgacggggc tgtgcttttc caagttgtac caatgtgaat    7920
gtgctaggtg gcaaccttca gttatctttt tttttagggt agttatctta ctccctccgt    7980
tcctaaataa ttgtctctct agagatttca acaaatgact acatacggaa caaaatgagt    8040
gaatctacac tctaaaacat gtctacatac atccgtatgt tgtagtttat ttgagatagc    8100
tagaaagaca attatttagg aacggaggga gtattatcta gtactccctc cgctcggaaa    8160
tacttgtcag ggagattgat gtatctagat gtattcttgt tctagatgca tccattttca    8220
tcaaattctt cgacaagtat ttccggacgg agggagtatg tagtactact actactatta    8280
cttacttttt gcaggtaaaa ttaaattatg gtctcatatg gctatattca tatcacataa    8340
tttatcagat tataatttta tttagaccaa gaatataaat ttagttgtaa gcccctagaaa    8400 tatactagga agccatcaaa ttatactagt attttttaagt attcccatag aaaaatgtat    8460
ttttaagcat ttagtttttt tagcatcttt atttttttgaa agagttaaat gcactcaagg    8520
```

```
tcctaaaaaa ttcgtcaggg tgtcactttα gtcttatttc gtccaaaatg cacctttagg    8580
tcctaattct ttagtaagtg gtttacccta ggtccttttt ctcacgagcg ctcgttgacc    8640
tgctcgtgtg gtgcgttgac ccatgccaaa tcgacagaag ggctgcgtag gttgctcttt    8700 cttttttacag aaaaccctta taaacattat cttctcattc cccagtccct ggctttattt    8760
cttccccaaa tctgctctct ctctcggcgc gcgcgtccct aaacctatcc atggccggaa    8820
cttcaagctc ctcggcaagg aaacaactaa gatgaggagc atggcaacat cctcagcacc    8880
gccgccggcg cggcgaagca agctccaact tcggcgggta tgttgccgct ggtggtgtgt    8940
cctttttgcc gtgtccgtat caccgttatg caaatcaaag taaatcaagg actacaacta    9000
ttgattatga caaagttatg acatattaga agagctacag gagaagatca tcgacaagat    9060
tagggttctt acggtaacat ggaggaggat tgctcactgg ccgtcataga aggggcatct    9120
tcacgggcac ccacacaaat tacctccaga tcacctccgg ttgcctctgt cgctcgcctc    9180
caatgtcgcc aaagtaccgt gaaagaggag agagggtgcc actaagaggg gggggggtctc   9240 tttgcgaagc ttctcgcctg gcggttagac cctctatcga tgtggcatgg gtcaatgcgg    9300
cacgtgtgct ggtcagcgag cgctcgtgga aaaggacctc gggtgaacca attaataaag    9360
aattaggacc taaaggtgca ttttggaaga aataggacta aagtgacacc ccgacgaaac    9420
ctttaggacc tccagtgcat ttaactcttt ttgaaacgag gtaaaagact tgccattttc    9480
actgattaag aagaagagag ttgcccggtt aattaaaaca cgcccatcga ataggcact    9540 ccagccgacc tggcactgac aagatcacac acatactgct gacgagagga caccgtcgag    9600
gctgcaatgt catcgtcatc gcctctccac gagcaggcaa ctccgatttc ctcgctgacg    9660
acccatcaag acccctccga acaaacggca cccgaggacc tcgacagcca agccaaatga    9720
tcggccgcag gcgtcgagga ccgacatctc cgattttgtt gatgagcatc acaggagaaa    9780
gttgcaagcc tcacaccaag ctagtccagt gcaacctgcg gagagcatcg tccgccgaaa    9840
ccaccctcat ggagtcatca ttgccgcagg gcccccgccg catgtagctt caacttctct    9900
gtcacagtga gaaacaagca cagacgcacc caaaggggaa ccgaaccgcc gatatcagaa    9960
ggacaagccg cgacccagct tcgcgcatca ccatcttcgt caccgcacga gtcgcaacgc   10020
caaccactcg tatcaccggt tgagcaccag ccaaccatga caccatgcac gaccagccca   10080
aaggtagcac gggaaaggat aaccggtctt caaagcaacg ccccaaaggg ggaaaacacc   10140
gtacggacga catcgttgcc cgacctagat gggcgaggtt ttcgcctgaa gaaccagatt   10200
cgagattgta gtaggtcgaa gaactctaca acaacgcctt caacaaggga aacgacgccc   10260
ataggcgccg ccagcaccgg ccggccatag ccgggcaagc ttgcgcttgg agcagactca   10320
accaacaccc tcacgcagcc gacacaagct ggcccgcgca atcgctggca tgcacacccc   10380
tgcgcagcaa ccgcgccatc gcctcacaag gcccacggcc caccatagag cacacacacc   10440
ccttgctgcc agaggcaagg tcaccggat gaccgaccct gagtaagatg agagacgagc    10500
tggatccgaa tgaagaaccg ccggatctgg cgccccttg cagcagcact acaacaacca     10560
ccaagggccg gccagagcag tcgacctgcg cggagacgaa tgaccaaagg aaggaaaggg    10620
gggccgccac cccgcccata tcgccgagc aagagccgcc ggaccgaagc ccaggagttt     10680
gccgacgaca ccaccgcgac tgccacccgc tggagacgca acttcggaga atcttcgtgc   10740
cgtagccgcc gcgccgcact gcgaggaggc gtgcctccct caccatgaga cccggacgct   10800
gcagagaggc cccgccgccg tcgtccaccg cacaggctta gcccggcggc ctcctccggc   10860
```

```
gacggcgagg tagggaggcg agggggggcgc ccgtgtcttc aaggaggatg tgtgggggat    10920
gggggggggg gggtatcttt ttagcatcta ggtggtgaat tttgtgccgt gaaatcccgc    10980
ccatgttgtc ccaactaaaa gttggaagtc tattactagt ggtggccgag gttctcaacg    11040
ccttcccttc ttcagatgtg cctaacatgc gtaacatgac caaatggtgt tttgtgatgc    11100
gaaccatgtc ttctgatgtc gttcgttgtg ctccgggatc agatgctttt gggtaatcaa    11160
ctcatggacg gggagaatgg caagatgcca cacgggatgc ctggaaaatg aactcggcat    11220
gatgactttc tcatgacagg atggtgtcac gttgattacc ccgtcgcgtc gaaagccaaa    11280
tagtgctacg tcaaaatggg cagatagaga tggtgaatca agccattggt ggtgtcagtc    11340
ctgattgacc atttggattc cgcgatgatg tttaaggcat tttctcacta caaaaattcc    11400
cccaagatca gacatcatca tcacatctcg gtatcctctt acttaagttt gcttggagct    11460
ccatcttggg ttgtggtgac ccaagtatta aattttgttg ttgggtataa cactggatct    11520
acaaaatttt catagaaaat gcatgcatct gatagctgca caaattatta ttttttgcaa    11580
acatacagtg atccataata tctgcaaaca gaccctaatg tctgctattc tagatcacgc    11640
cattttcttt tctgtaccgc tcatggtcca aacgagtttc ttctgaattt tgtgaactta    11700
gtagatttct tcttacactt agggtgcgtt tggaagccga agtattttg tggttttctg     11760 gaatactgtg gttttgaaa aaactttgg tatttaatac tttgagtcgt ttggataaaa       11820 aaatactgc agttcaacaa accatgatat ctctaaaact gtggtatttt tgttgtatat     11880 aaaaagagg ccctgacctc ttttttttaa aaccgagaaa gcgctggctg ctggtctctc      11940
ttgtgtccaa cttctggcca tcaacgactg tgatgcataa a                         11981
```

<210> SEQ ID NO 22
<211> LENGTH: 18
<212> TYPE: RNA
<213> ORGANISM: Artificial Sequence
<220> FEATURE:
<223> OTHER INFORMATION: predicted RNA target
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u

<400> SEQUENCE: 22
accuguncgu aynygcau                                                        18

<210> SEQ ID NO 23
<211> LENGTH: 895
<212> TYPE: DNA
<213> ORGANISM: Triticum aestivum x Triticum timopheevi

<400> SEQUENCE: 23

```
tcttccagcg tttagtattc aagttcttct cttccagccc cccggcccct ctttgataag    60
gaaagtttgc atttctcaaa taaaaaatga caaatatggt tcgatggctc ttctccacta    120
gcaggtttac tgctttctat ttgcactttt gtattaagtt tccttatata tacgattttt    180
tattattttc tatttgtcta ttttctttt tagtgcgttt tatttcgatt attcttctcc     240
caatttgcaa tcttttcgga gcctccttca ttattactct tcctccagag attcaggatc    300
cccaagctct agctcattta gcagggctaa acttctatct gagcctttac gagcaggatc    360
ctggatgggt tacgttcatt cagaacgagc ttaatcacaa taccccctctg gaggacatac    420
```

```
ctggacggct taagctcttc ctaatggaag aaaagctgtc tagtatgcga caagatgtca      480
ttcaggaatt tgtggcgctt tatcaaagaa tagggcctta tctaccgatc gagccctact      540
tggtcgatga agcgcttcgt tcctatctgg accatattca cgcaactgat tctttcactg      600
ttctccaagc gtcttatcaa gatctgcggg agaatgaggg aggatctgtt ttctttagag      660
atgctgtttc ccacaaccgg gatctccttg aggcggaaag ctccgcaagg aggtgcctgg      720
aagtggaaca gaggatccga tgggaagaaa tccccaagag caaggcaagt ctcgaaagag      780
ctgagcacga gcatgctctc gacttgttta agtcggagga tcttagaagg gaattagaaa      840
aaaaaagagc ggggtagctc agtaattctg attctttct cttccagccc ccggg            895
```

```
<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
tgatggtgtt ggacctgata atgt                                              24

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
ccagtggcct gaagaggaat at                                                22

<210> SEQ ID NO 26
<211> LENGTH: 21
<212> TYPE: DNA
<213> ORGANISM: Artificial Sequence
<220> FEATURE:
<223> OTHER INFORMATION: probe

<400> SEQUENCE: 26
acgtatagta gcctcatcca t                                                 21

<210> SEQ ID NO 27
<211> LENGTH: 56
<212> TYPE: DNA
<213> ORGANISM: Artificial Sequence
<220> FEATURE:
<223> OTHER INFORMATION: nucleotides 119 to 174 of ORF256 sequence of
      SEQ ID NO: 23

<400> SEQUENCE: 27
tagcaggttt actgctttct atttgcactt ttgtattaag tttccttata tatacg           56

<210> SEQ ID NO 28
<211> LENGTH: 18
<212> TYPE: DNA
<213> ORGANISM: Artificial Sequence
<220> FEATURE:
<223> OTHER INFORMATION: DNA sequence for the predicted target RNA of
      SEQ ID NO: 22
<220> FEATURE:
<221> NAME/KEY: misc_feature
<222> LOCATION: (7)..(7)
<223> OTHER INFORMATION: n is a, c, g, or t
<220> FEATURE:
```

```
<221> NAME/KEY: misc_feature
<222> LOCATION: (12)..(12)
<223> OTHER INFORMATION: y is c or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (14)..(14)
<223> OTHER INFORMATION: y is c or t

<400> SEQUENCE: 28
acctgtncgt aynygcat                                               18
```